(12) United States Patent  (10) Patent No.: US 8,158,612 B2
Agoston et al.  (45) Date of Patent: Apr. 17, 2012

(54) METHODS OF TREATING DISEASE STATES USING ANTIANGIOGENIC AGENTS

(75) Inventors: Gregory E. Agoston, Germantown, MD (US); Jamshed H. Shah, Brookeville, MD (US); Lita Suwandi, Alexandria, VA (US); Theresa M. LaVallee, Rockville, MD (US); Anthony M. Treston, Rockville, MD (US)

(73) Assignee: EntreMed, Inc., Rockville, MA (US)

( * ) Notice: Subject to any disclaimer, the term of this patent is extended or adjusted under 35 U.S.C. 154(b) by 630 days.

(21) Appl. No.: 12/341,068

(22) Filed: Dec. 22, 2008

(65) Prior Publication Data

US 2009/0105205 A1  Apr. 23, 2009

Related U.S. Application Data

(62) Division of application No. 11/077,977, filed on Mar. 11, 2005, now Pat. No. 7,498,322.

(60) Provisional application No. 60/562,793, filed on Apr. 16, 2004, provisional application No. 60/552,692, filed on Mar. 12, 2004.

(51) Int. Cl.
*A61K 31/56* (2006.01)
(52) U.S. Cl. ........................................ 514/169; 514/182
(58) Field of Classification Search .................. 514/169, 514/182
See application file for complete search history.

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,117,140 A | 1/1964 | Hecker |
| 3,166,577 A | 1/1965 | Ringold et al. |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,562,260 A | 2/1971 | De Ruggieri et al. |
| 3,956,348 A | 5/1976 | Hilscher |
| 4,172,132 A | 10/1979 | Draper et al. |
| 4,212,864 A | 7/1980 | Tax |
| 4,307,086 A | 12/1981 | Tax |
| 4,444,767 A | 4/1984 | Torelli et al. |
| 4,522,758 A | 6/1985 | Ward et al. |
| 4,552,758 A | 11/1985 | Murphy et al. |
| 4,634,705 A | 1/1987 | DeBernardis et al. |
| 4,743,597 A | 5/1988 | Javitt et al. |
| 4,808,402 A | 2/1989 | Leibovich et al. |
| 4,994,443 A | 2/1991 | Folkman et al. |
| 5,001,116 A | 3/1991 | Folkman et al. |
| 5,135,919 A | 8/1992 | Folkman et al. |
| 5,166,149 A | 11/1992 | Loev |
| 5,504,074 A | 4/1996 | D'Amato et al. |
| 5,521,168 A | 5/1996 | Clark |
| 5,621,124 A | 4/1997 | Seilz et al. |
| 5,629,340 A | 5/1997 | Kuwano et al. |
| 5,639,725 A | 6/1997 | O'Reilly et al. |
| 5,643,900 A | 7/1997 | Fotsis et al. |
| 5,646,136 A | 7/1997 | Petrow |
| 5,661,143 A | 8/1997 | D'Amato et al. |
| 5,716,981 A | 2/1998 | Hunter et al. |
| 5,733,876 A | 3/1998 | O'Reilly et al. |
| 5,763,432 A | 6/1998 | Tanabe et al. |
| 5,776,704 A | 7/1998 | O'Reilly et al. |
| 5,792,845 A | 8/1998 | O'Reilly et al. |
| 5,837,682 A | 11/1998 | O'Reilly |
| 5,854,205 A | 12/1998 | O'Reilly et al. |
| 5,854,221 A | 12/1998 | Cao et al. |
| 5,861,372 A | 1/1999 | Folkman et al. |
| 5,885,795 A | 3/1999 | O'Reilly et al. |

(Continued)

FOREIGN PATENT DOCUMENTS

DE  1907330  10/1969

(Continued)

OTHER PUBLICATIONS

Office Action in U.S. Appl. No. 10/789,471 mailed Aug. 12, 2009. *USPTO Office Action*, pp. 1-11.

(Continued)

*Primary Examiner* — Barbara P Badio
(74) *Attorney, Agent, or Firm* — Johnson, Marcou & Isaacs, LLC; Robert E. Richards

(57) ABSTRACT

Compositions and methods for treating mammalian diseases or conditions characterized by undesirable angiogenesis by administering an effective amount of a compound of the formulae:

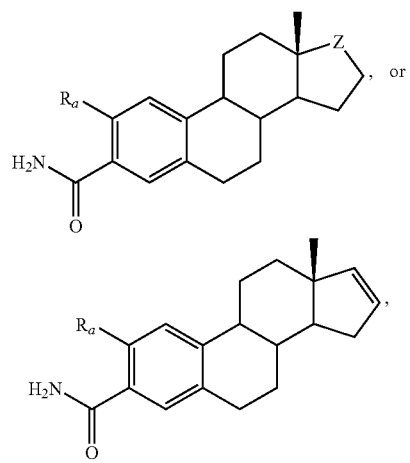

wherein $R_a$ is selected from —$OCH_3$, —$OCH_2CH_3$ or —$CCCH_3$; and Z is selected from >C(H)—OH, >C(H)—O-alkyl, >C(H)—O-sulfamate, where alkyl is a linear, branched and/or cyclic hydrocarbon chain comprising 1 to 10 carbons.

18 Claims, No Drawings

U.S. PATENT DOCUMENTS

| | | | |
|---|---|---|---|
| 5,892,069 | A | 4/1999 | D'Amato et al. |
| 5,919,459 | A | 7/1999 | Nacy et al. |
| 5,958,892 | A | 9/1999 | Mukhopadhyay et al. |
| 5,962,445 | A | 10/1999 | Stewart |
| 6,011,023 | A | 1/2000 | Clark et al. |
| 6,011,024 | A | 1/2000 | Reed |
| 6,046,186 | A | 4/2000 | Tanabe et al. |
| 6,051,726 | A | 4/2000 | Sachdeva et al. |
| 6,054,598 | A | 4/2000 | Sachdeva et al. |
| 6,136,992 | A | 10/2000 | Ram et al. |
| 6,200,966 | B1 | 3/2001 | Stewart |
| 6,239,123 | B1 | 5/2001 | Green et al. |
| 6,284,789 | B1 | 9/2001 | LaLonde et al. |
| 6,358,940 | B1 | 3/2002 | Conney |
| 6,399,773 | B1 | 6/2002 | Liu et al. |
| 6,407,086 | B2 | 6/2002 | Faarup et al. |
| 6,410,029 | B1 | 6/2002 | Mukhopadhyay et al. |
| 6,448,419 | B1 | 9/2002 | Paaren et al. |
| 6,514,971 | B1 | 2/2003 | Thomas et al. |
| 6,528,676 | B1 | 3/2003 | D'Amato et al. |
| 6,593,321 | B2 | 7/2003 | Rao et al. |
| 6,605,622 | B2 | 8/2003 | Green et al. |
| 6,723,858 | B2 | 4/2004 | D'Amato et al. |
| 6,730,665 | B1 | 5/2004 | Maran et al. |
| 6,759,386 | B2 | 7/2004 | Franco |
| 6,852,710 | B2 | 2/2005 | Rao et al. |
| 6,908,910 | B2 | 6/2005 | D'Amato et al. |
| 6,930,128 | B2 | 8/2005 | D'Amato et al. |
| 6,953,785 | B2 | 10/2005 | Ino et al. |
| 6,995,278 | B2 | 2/2006 | Agoston et al. |
| 6,998,395 | B2 | 2/2006 | Jackson et al. |
| 7,012,070 | B2 | 3/2006 | D'Amato et al. |
| 7,081,477 | B2 | 7/2006 | D'Amato et al. |
| 7,087,592 | B1 | 8/2006 | Agoston |
| 7,109,187 | B2 | 9/2006 | D'Amato et al. |
| 7,135,581 | B2 | 11/2006 | Agoston |
| 7,235,540 | B2 | 6/2007 | Agoston et al. |
| 7,291,610 | B2 | 11/2007 | D'Amato et al. |
| 7,351,729 | B2 | 4/2008 | Stein et al. |
| 7,371,741 | B2 | 5/2008 | Agoston et al. |
| 7,381,848 | B2 | 6/2008 | D'Amato et al. |
| 2002/0002294 | A1 | 1/2002 | D'Amato et al. |
| 2002/0035098 | A1 | 3/2002 | Slaga et al. |
| 2002/0068724 | A1 | 6/2002 | Slaga et al. |
| 2003/0027803 | A1 | 2/2003 | Slaga et al. |
| 2003/0036539 | A1 | 2/2003 | Slaga et al. |
| 2003/0073674 | A1 | 4/2003 | Slaga et al. |
| 2003/0096799 | A1 | 5/2003 | Rao et al. |
| 2003/0175961 | A1 | 9/2003 | Herron |
| 2004/0033267 | A1 | 2/2004 | Merisko-Liversidge et al. |
| 2004/0053906 | A1 | 3/2004 | Slaga et al. |
| 2004/0082558 | A1 | 4/2004 | Tofovic et al. |
| 2004/0116397 | A1 | 6/2004 | Slaga et al. |
| 2004/0121769 | A1 | 6/2004 | Ljubimov |
| 2004/0156854 | A1 | 8/2004 | Mulligan et al. |
| 2004/0186086 | A1 | 9/2004 | Bunschoten et al. |
| 2004/0198671 | A1 | 10/2004 | Bunschoten et al. |
| 2004/0209855 | A1 | 10/2004 | Tofovic et al. |
| 2004/0214807 | A1 | 10/2004 | D'Amato et al. |
| 2005/0032766 | A1 | 2/2005 | Green et al. |
| 2005/0070488 | A1 | 3/2005 | Coelingh Bennik et al. |
| 2005/0101573 | A1 | 5/2005 | Faarup et al. |
| 2005/0148496 | A1 | 7/2005 | Defranoux et al. |
| 2005/0148565 | A1 | 7/2005 | Cooperwood |
| 2005/0182038 | A1 | 8/2005 | Cooperwood |
| 2005/0192258 | A1 | 9/2005 | Agoston et al. |
| 2005/0203075 | A1 | 9/2005 | Agoston |
| 2005/0250751 | A1 | 11/2005 | Lee et al. |
| 2005/0266067 | A1 | 12/2005 | Sengupta et al. |
| 2006/0025393 | A1 | 2/2006 | Liao et al. |
| 2006/0025619 | A1 | 2/2006 | Agoston |
| 2006/0116360 | A1 | 6/2006 | Fogler |
| 2006/0135796 | A1 | 6/2006 | Agoston |
| 2006/0199776 | A1 | 9/2006 | Blagg et al. |
| 2006/0205787 | A1 | 9/2006 | Muller et al. |
| 2007/0004689 | A1 | 1/2007 | Agoston et al. |
| 2007/0135400 | A1 | 6/2007 | Agoston et al. |

FOREIGN PATENT DOCUMENTS

| | | | |
|---|---|---|---|
| DE | 3625315 | | 1/1988 |
| EP | 0166937 | A2 | 8/1986 |
| GB | 857080 | | 12/1960 |
| GB | 857081 | | 12/1960 |
| GB | 1570597 | | 7/1980 |
| GB | 2252498 | A | 8/1992 |
| JP | 39-5480 | B | 4/1939 |
| JP | 41 000100 | A | 1/1966 |
| JP | 42000928 | B | 1/1967 |
| JP | 62-135472 | | 6/1987 |
| JP | 63090763 | A | 4/1988 |
| JP | 63-119500 | | 5/1988 |
| JP | 04-046120 | | 2/1992 |
| WO | WO 87/02367 | A3 | 4/1987 |
| WO | WO 88/03151 | A2 | 5/1988 |
| WO | WO 88/08002 | A1 | 10/1988 |
| WO | WO 90/15816 | A1 | 12/1990 |
| WO | WO 93/03729 | A1 | 3/1993 |
| WO | WO 93/10805 | A1 | 6/1993 |
| WO | WO 93/19746 | A1 | 10/1993 |
| WO | WO 95/04535 | A1 | 2/1995 |
| WO | WO 98/32763 | A1 | 7/1998 |
| WO | WO 98/40398 | | 9/1998 |
| WO | WO 99/01142 | A1 | 1/1999 |
| WO | WO 99/22728 | A1 | 5/1999 |
| WO | WO 99/33858 | A3 | 7/1999 |
| WO | WO 99/33859 | A2 | 7/1999 |
| WO | WO 99/35150 | A3 | 7/1999 |
| WO | WO 00/07576 | A2 | 2/2000 |
| WO | WO 00/10552 | A2 | 3/2000 |
| WO | WO 00/66095 | A2 | 11/2000 |
| WO | WO 00/68246 | A1 | 11/2000 |
| WO | WO 01/27132 | A1 | 4/2001 |
| WO | WO 01/85755 | A1 | 11/2001 |
| WO | WO 02/15910 | A1 | 2/2002 |
| WO | WO 2004/074307 | A1 | 9/2004 |
| WO | WO 2004/101595 | A1 | 11/2004 |
| WO | WO 2005/089256 | A2 | 9/2005 |

OTHER PUBLICATIONS

Bruno et al., New drugs for treatment of multiple myeloma, *The Lancet*, vol./Iss: 5, pp. 430-442, Jul. 1, 2004.

Chamaon et al., Micromolar Concentrations of 2-Methoxyestradiol Kill Glioma Cells by an Apoptotic Mechanism, without Destroying their Microtubule Cytoskeleton, *Journal of Neuro-Oncology* vol./Iss: 72, pp. 11-16, Jan. 1, 2005.

Office Action in U.S. Appl. No. 11/599,997 mailed Dec. 8, 2008, *USPTO Office Action*, pp. 1-9.

Cruysberg et al., Effective Transscleral Delivery of Two Retinal Anti-Angiogenic Molecules—Carboxyamido-triazole (CAI) and 2-Methoxyestradiol ($2ME_2$), *Retina*, vol./Iss: 25, pp. 1022-1032, Jan. 1, 2005.

EPO Search, Supplementary European Search Report—EP 05736385, *EPO Search Report*, pp. 1-4, Jun. 30, 2009.

Furukawa et al., Effects of Indole-3-Acetic Acid Derivatives on Neuroepithelium in Rat Embryos, *The Journal of Toxicological Sciences*, vol./Iss: 30 (3), pp. 165-174, Jan. 1, 2005.

Gao et al., 2-Methoxyestradiol-Induced Apoptosis in Human Leukemia Cells Proceeds Through a Reactive Oxygen Species and Akt-Dependent Process *Oncogene*, pp. 1-13, Jan. 1, 2005.

Han et al., Synergism between the Anticancer Actions of 2-Methoxyestradiol and Microtubule—Disrupting Agents in Human Breast Cancer, *Cancer Research*, vol./Iss: 65 (2), pp. 387-393, Jan. 15, 2005.

Hou et al., 2-Methoxyestradiol at Low Dose Induces Differentiation of Myeloma Cells *Leukemia Research*, vol./Iss: 29, pp. 1059-1067, Jan. 1, 2005.

Jeung et al., Thymidine Phosphorylase Suppresses Apoptosis Induced by Microtubule-Interfering Agents, *Biochemical Pharmacology*, vol./Iss: 70, pp. 13-21, Jan. 1, 2005.

Joubert et al., Influence of Prostaglandin $A_2$ and 2-Methoxyestradiol on Bax and Bcl-2 Expression Levels in Cervical Carcinoma Cells, *Biomedical Research*, vo./Iss: 26 (2), pp. 87-90, Jan. 1, 2005.

Joubert et al., Bax/Bcl2 Expression Levels of 2-Methoxyestradiol-Exposed Esophageal Cancer Cells, *Biomedical Research*, vol./Iss: 26 (3), pp. 131-134, Jan. 1, 2005.
Kim et al., Mitogenic Estrogen Metabolites Alter the Expression of 17β-Estradiol-Regulated Proteins including Heat Shock Proteins in Human MCF-7 Breast Cancer Cells, *Molecules and Cells*, vol./Iss; 20 (3), pp. 378-384, Jan. 1, 2005.
Office Action in U.S. Appl. No. 11/519,570 mailed Dec. 9, 2008, *USPTO Office Action*, pp. 1-12.
Lakhani et al., Determination of 2-Methoxyestradiol in Human Plasma, Using Liquid Chromatography/Tandem Mass Spectrometry, *Rapid Commun Mass Spectrom*, vol./Iss; 19, pp. 1176-1182, Dec. 1, 2005.
Leese et al., Anti-Cancer Activities of Novel D-ring Modified 2-Substituted Estrogen-3-*O*-Sulfamates, *Juornal of Steroid Biochemistry and Molecular Biology*, vol./Iss: 94, pp. 239-251, Jan. 1, 2005.
Lewis et al., Differential Effects of 16α-Hydroxyestrone and 2-Methoxyestradiol on Cyclin D1 Involving the Transcription Factor ATF-2 in MCF-7 Breast Cancer Cells, *Journal of Molecular Endocrinology*, vol./Iss: 34, pp. 91-105, Jan. 1, 2005.
Li et al., Antiproliferative Activity and Toxicity of 2-Methoxyestradiol in Cervical Cancer Xenograft Mice, *Int. J. Gynecol. Cancer*, vol./Iss: 15, pp. 301-307, Jan. 1, 2005.
Liehr et al., Carcinogenicity of Catechol Estrogens in Syrian Hamsters, *Journal of Steroid Biochemistry*, vol./Iss: 24 (1), pp. 353-356, Jan. 1, 1986.
Liu et al., Suppressive Effects of 17b-Estradiol on Hepatic Fibrosis in CCI4-Inclueed Rat Model, *World Journal of Gastroenterology*, vol./Iss: 10 (9), pp. 1-11, May 1, 2004.
Montgomery et al., Estrogen Effects on Tubulin Expression and Taxane Mediated Cytotoxicity in Prostate Cancer Cells, *The Prostate*, vol./Iss: 9999, pp. 1-10, Jan. 1, 2005.
Nguyen et al., A Common Pharmacophore for a Diverse Set of Colchicine Site Inhibitors Using a Structure-Based Approach, *J. Med. Chem.*, vol./Iss: 48, pp. 6107-6116, Jan. 1, 2005.
Pellegrini et al., Review: Tubulin Function, Action of Antitubulin Drugs, and New Drug Development *Cancer Investigation*, vol./Iss: 23, pp. 264-273, Jan. 1, 2005.
Seeger et al., Different Effects of Estradiol and Various Antiestrogens on TNF-α-induced Changes of Biochemical Markers for Growth and Invasion of Human Breast Cancer Cells, *Life Sciences*, vol./Iss: XX, pp. 1-5, Jan. 1, 2005.
Shah et al., Monocrotaline pyrrole-induced endothelial cell megalocytosis involves a Goigi blockage mechanism, *Am. J. Physiol. Cell Physiol*. vol./Iss: 288, pp. C850-C862, Nov. 23, 2004.
Stafford et al., Colchicine and 2-methoxyestradiol Inhibit Human Angiogenesis, *Journal of Surgical Research*, vol./Iss: 125, pp. 104-108, Jan. 1, 2005.
Sutherland et al., 2-Methoxyestradiol Is an Estrogen Receptor Agonist That Supports Tumor Growth in Murine Xenograft Models of Breast Cancer, *Clinical Cancer Research*, vol./Iss: 11, pp. 1722-1732, Mar. 1, 2005.
Viggiano et al., Trigeminal Pain Transmission Requires Reactive Oxygen Species Production, *Brain Research*, vol./Iss: 1050, pp. 72-78, Jan. 1, 2005.
Yang et al., Constitutively Active FOX04 inhibits Akt Activity, Regulates p27 Kip1 Stability, and Suppresses HER2-Medicated Tumorigenicity, *Oncogene*, vol./Iss: 24, pp. 1924-1935, Jan. 1, 2005.
Zhou et al., 2-Methoxyestradiol induces cell cycle arrest and apoptosis of nasopharyngeal carcinoma cells, *Acta Pharmacologica Sinica*, vol./Iss: 25 (11), pp. 1515-1520, Nov. 1, 2004.
Zhu et al., NADPH-Dependent Metabolism of 17β-Estradiol and Estrone to Polar Nonpolar Metabolites by Human Tissues and Cytochrome P450 Isoforms *Steroids*, vol./Iss: 70, pp. 225-244, Jan. 1, 2005.
Office Action in U.S. Appl. No. 11/489,263, *USPTO Office Action*, pp. 1-10, May 2, 2008.
Office Action in U.S. Appl. No. 11/701,809, *USPTO Office Action*, pp. 1-12, Aug. 21, 2008.
Office Action in U.S. Appl. No. 11/077,977, *USPTO Office Action*, pp. 1-16, Sep. 30, 2008.
EPO Search, EPO Supplementary Search EP 07753617.5, *EPO Search Report*, pp. 1-7, Apr. 14, 2010.
EPO Search, EPO Search Report filed in 05016659.4 dated Dec. 20, 2005, *EPO Search Report*, pp. 1-7.
Office Action in U.S. Appl. No. 11/519,570, *USPTO Office Action*, pp. 1-6, May 23, 2008.
Riedel et al., XP009057873; Abstract No. 952-132: Acute Vascular Responses to 17β-Estradiol in Postmenopausal Women with and without Atherosclerosis, *Journal of the American College of Cardiology*, pp. 380A, Mar. 13, 1994.
Office Action in U.S. Appl. No. 12/262,318, *USPTO Office Action*, pp. 1-8, Sep. 15, 2010.
Office Action in U.S. Appl. No. 11/288,989, *USPTO Office Action*, pp. 1-14, Oct. 14, 2008.
Lilopristone/(I-[4-(Dimethlylamino)phenyl]-17-hydroxy-17-(3-hydroxy-I-propenyl)estra-4,9-diene-3-one; AK 98734, *Dictionary of Drugs* (1990), *Dict. of Steroids* (1991), *Dict. of Org. Cmpds* (6th Ed) (1996).*Dist of Pharm Agents* (2007), 1990.
(Paragraphs 583-584), *The Merck Index 11th Edition*, pp. 88, 1989.
*Research Plus Catalog*, pp. 50-58, 1993.
News Article: Hoffman-La Roche Signs $70 Million Deal with Millenium on Genomics Technology, *Genetic Engineering News*, Apr. 15, 1994.
News Article: Advanced Drug Delivery Systems Peak Interest of Pharmaceutical & Biotech Firms, *Genetic Engineering News*, Apr. 15, 1994.
News Article: Nasal Spray for Treating Bleeding Disorders, *Genetic Engineering News*, Apr. 15, 1994.
2-Methoxyestradiol—An Orally Active Endogenous Inhibitor of Angiogenesis, *EntreMed Website Article*, pp. 1-10, Jul. 11, 2000.
Peripheral Ulcerative Keratitis (Marginal Keratolysis; Peripheral Rheumatoid Ulceration) (Abstract only), *Merck Manual of Diagnosis and Therapy*, vol./Iss: Sec. 8, pp. Chapter 8 & 96, Jan. 1, 1995.
Aboulwafa et al., Synthesis and evaluation for uterotrophic and antiimplantation activities of 2-substituted estradiol derivatives, *Steroids*, vol./Iss: 57, pp. 199-204, Apr. 1992.
Adams, E.F. et al., Steroidal regulation of oestradiol-17β dehydrogenase activity of the human breast cancer cell line MCF-7 (Chemical Abstracts Doc. No. 109:32325, 1988), *Journal of Endocrinology*, vol./Iss: 118 (1), pp. 149-154, Jul. 1988.
Aguayo et al., Angiogenesis in Acute and Chronic Leukemias and Myelodysplastic Syndrome, *Blood*, vol./Iss: 96 (6), pp. 2240-2245, Sep. 15, 2000.
Aizu-Yokota et al., Natural Estrogens Induce Modulation of Microtubules in Chinese Hamster V79 Cells in Culture, *Cancer Research*, vol./Iss: 55, pp. 1863-1868, May 1, 1995.
Akova et al., Optic Disk Neovascularization in a Patient with Cytomegalovirus Retinitis Associated with Renal Transplantation (Abstract only), *Ocular Immunology and Inflammation*, vol./Iss: 8 (1), pp. 63-65, Mar. 1, 2000.
Algire, G.H. et al., Vascular reactions of normal and malignant tumors in vivo. I. Vascular reactions of mice to wounds and to normal and neoplastic transplants, *Journal of the National Cancer Institute*, vol./Iss: 6, pp. 73-85, Aug. 1945.
Aliev et al., 54929q Synthesis of cycloalkyl derivatives of dihydric phenols and their ethers, *Chemical Abstracts*, vol./Iss: 72, pp. 370, 1970.
Amant et al., 2-Methoxyestradiol strongly inhibits human uterine sarcomatous cell growth, *Gynecologic Oncology*, vol./Iss: 91, pp. 299-308, Jan. 2003.
Amorino et al., Enhancement of Radiation Effects In Vitro by the Estrogen Metabolite 2-Methoxyestradiol, *Radiation Research*, vol./Iss: 153, pp. 384-391, Jan. 1, 2000.
Anderson et al., Mutliple Myeloma: New Insights and Therapeutic Approaches (Abstract only), *Hematology*, pp. 147-165, Jan. 1, 2000.
Anstead et al., The Estradiol Pharmacophore: Ligand Structure-Estrogen Receptor Binding Affinity Relationships and a Model for the Receptor Binding Site, *Steroids*, vol./Iss: 62, pp. 268-303, 1997.
Arbiser et al. The Antiangiogenic Agents TNP-470 and 2-Methoxyestradiol Inhibit the Growth of Angiosarcoma in Mice, *Journal of the American Academy of Dermatology*, vol./Iss: June, Part 1, pp. 925-929, Jun. 1999.
Armstrong et al., Detection of Vascular Endothelial Growth Factor and Tumor Necrosis Factor Alpha in Epiretinal Membranes of Proliferative Diabetic Retinopathy, Proliferative Vitroretinopathy and Macular Pucker, *Ophthalmologica*, vol./Iss: 212 (6), pp. 410-414, Nov. 1, 1998.

Arnoldi et al., Sweet Isovanillyl Derivatives: Synthesis and Structure-Taste Relationships of Conformationally Restricted Analogs (Abstract only), *Journal of Agric. Food Chem.* vol./Iss; 46(10), pp. 4002-4010, 1998.

Attalla et al., 2-Methoxyestradiol Arrests Cells in Mitosis without Depolymerizing Tubulin *Biochemical and Biophysical Research Communications*, vol./Iss: 228, pp. 467-473, 1996.

Attalla et al., 2-Methoxyestradiol-Induced Phosphorylation of Bcl-2: Uncoupling from JNK/SAPK Activation (Abstract only) *Biochemical and Biophysical Research Communications*, vol./Iss: 247 (3), pp. 616-619, Jun. 29, 1998.

Audier et al., Orientation de la fragmentation en spectrometrie de masse par introduction de groupements fonctionnels. VII—Etheylenecetals de ceto-2 steroides, *Bulletin De La Societe Chimique De France*, vol./Iss: 10, pp. 3088-3090, 1965.

Avvakumov et al., Crystal Structure of Human Sex Hormone-binding Globulin in Complex with 2-Methoxyestradiol Reveals the Molecular Basis for High Affinity Interactions with C-2 Derivatives of Estradiol, *The Journal of Biological Chemistry*, vol./Iss: 277 (47), pp. 45219-45225, Nov. 22, 2002.

Ayala et al., The Induction of Accelerated Thymic Programmed Cell Death During Polymicrobial Sepsis: Control by Corticosteroids but not Tumor Necrosis Factor (Abstract only), *Shock*, vol./Iss: 3 (4), pp. 259-267, Apr. 1995.

Azuma, H., Genetic and Molecular Pathogenesis of Hereditary Hemorrhagic Telangiectasia *Journal of Medical Investigation*, vol./Iss: 47 (3-4), pp. 81-90, Aug. 1, 2000.

Bacharach et al., In vivo Patterns of Expression of Urokinase and Its Inhibitor PA1-I Suggest a Concerted Role in Regulating Physiological Angiogenesis, *Procedings of the National Academy of Science USA*, vol./Iss: 89 (22), pp. 10686-10690, Nov. 15, 1992.

Baer et al., Corneal Laser Photocoagulation for Treatment of Neovascularization. Efficacy of 577 nm Yellow Dye Laser (Abstract only), *Ophthalmology*, vol./Iss: 99 (2), pp. 173-179, Feb. 1, 1992.

Banerjee et al., 2-Methoxyestradiol Blocks Estrogen-Induced Rat Pituitary Tumor Growth and Tumor Angiogenesis: Possible Role of Vascular Endothelial Growth Factor, *Anticancer Research*, vol./Iss: 20, pp. 2641-2646, Jan. 1, 2000.

Banik et al., Orally Active Long-Acting Estrogen (AY-20,121) (3-(2-propynyloxy)-estra-1,3,5,(10)-triene-17. beta.-ol trimethylacetate) (Identifier only), *Steroids*, vol./Iss: 16 (3), pp. 289-296, 1970.

Barczyk et al., Mast Cells in the Gastrointestinal Tract (Abstract only), *Roczniki Akademii Medycznej W Bialymstoku (Bialystok)*, vol./Iss: 40 (1), pp. 36-57, Jan. 1, 1995.

Bardon et al., Steroid Receptor-Mediated Cytotoxicity of an Antiestrogen and an Antiprogestin in Breast Cancer Cells (Abstract only), *Cancer Research*, vol./Iss: 47 (5), pp. 1441-1448, Mar. 1, 1987.

Barnes et al., Tumor Necrosis Factor Production in Patients with Leprosy, *Infection and Immunity*, vol./Iss: 60 (4), pp. 1441-1446, Apr. 1992.

Bhat et al., Estradiol-induced Mitotic Inhibition in the Bursa of Fabricius of Male Domestic Duckling (Chemical Abstracts Doc. No: 98:31837, 1982), *Mikroskopie*, vol./Iss: 39, pp. 113-117, May 1982.

Bhattacharyya et al., Tubulin aggregation and disaggregation: Mediation by two distinct vinblastine-binding sites, *National Academy of Sciences*, vol./Iss: 73 (7), pp. 2375-2378, Jul. 1976.

Bhooma et al., Eales' Disease: Accumulation of Reactive Oxygen Intermediates and Lipid Peroxides and Decrease of Antioxidants Causing Inflammation, Neovascularization and Retinal Damage (Abstract only), *Current Eye Research*, vol./Iss: 16 (2), pp. 91-95, Feb. 1, 1997.

Bindra et al., Studies in Antifertility Agents.8.Seco Steroids. 2. 5,6-Secoestradiol and Some Related Compounds, *Journal of Medicinal Chemistry*, vol./Iss: 18 (9), pp. 921-925, 1975.

Bissell et al., Putting Tumours in Context, *Nature Reviews Cancer*, vol./Iss: 1 (1), pp. 46-54, Oct. 1, 2001.

Blagosklonny et al., Raf-l/bcl-2 Phosphorylation: A Step from Microtubule Damage to Cell Death, *Cancer Research*, vol./Iss: 57, pp. 130-135, Jan. 1, 1997.

Blickenstaff et al., Estrogen-Catharanthus (Vinca) Alkaloid Conjugates (Chemical Abstracts Doc. No. 94:114277, 1981), *Cytotoxic Estrogens in Hormone Receptive Tumors*, pp. 89-105, 1980.

Blickenstaff et al., Synthesis of Some Analogs of Estradiol, *Steroids* vol./Iss: 46 (4,5), pp. 889-902, Oct. 1985.

Boehme et al., Juxtapapillary Choroidal Neovascular Membrane in a Patient with Paget's Disease and Lattice Corneal Dystrophy (Abstract only), *Journal of the American Optometric Association* vol./Iss: 60 (8), pp. 612-616, Aug. 1, 1989.

Boyce et al., Some Preliminary Synthetical Studies with 5,6,7,8-Tetra-hydro-8-methylindane-1,5-dione, Unknown, pp. 4547-4553, 1960.

Boye et al., 185,Deaminocolchinyl Methyl Ether: Synthesis from 2,3,4,4'- Tetramethoxybiphenyl- 2-carbaldehyde. Comparison of Antitubulin Effects of Deaminocolchinyl Methyl Ether and Dehydro Analogs, *Helvetica Chimica Acta*, vol./Iss: 72, pp. 1690-1696, 1989.

Brandi et al., Bone endothelial cells as estrogen targets (Abstract only) *Calcif. Tissue Int.*, vol./Iss: 53 (5), pp. 312-317, 1993.

Brem, H. et al., Interstitial chemotherapy with drug polymer implants for the treatment of recurrent gliomas *Journal of Neurosurgery*, vol./Iss: 74, pp. 441-446, Mar. 1, 1991.

Brodie, A.M., Aromatase Inhibitors in the Treatment of Breast Cancer (Abstract only) *Journal of Steroid Biochemistry and Molecular Biology*, vol./Iss: 49 (4-6), pp. 281-287, Jun. 1994.

Brosens et al., Comparative Study of the Estrogenic Effect of Ethinylestradiol and Mestranol on the Endometrium, *Contraception (Laboratory for Gynecological Physiopathology)*, vol./Iss: 14 (6), pp. 679-685, Dec. 1, 1976.

Brueggemeier et al., 2-Methoxymethylestradiol: A New 2-Methoxy Estrogen Analog that Exhibits Antiproliferative Activity and Alters Tubulin Dynamics, *Journal of Steroid Biochemistry & Molecular Biology*, vol./Iss: 78, pp. 145-156, 2001.

Bu et al., Mechanisms for 2-methoxyestradiol-induced apoptosis of prostrate cancer cells, *FEBS Letters*, vol./Iss: 531, pp. 141-151, Jan. 2002.

Burrows, N.P., Thalidomide Modifies Disease, *British Medical Journal*, vol./Iss: 307 (6909), pp. 939-940, Oct. 9, 1993.

Cambie et al., Aromatic Steroids. Part II. Chromium Trioxide Oxidation of Some Oestra-1,3-5(10)-trienes, *Journal of the Chemical Society*, vol./Iss: 9, pp. 1234-1240, 1969.

Cambie et al., Aromatic Steroids. Part I. Oxidation Products of 3-Methoxyestra-1,3,5(10)-triene- 17β-yl Acetate, *J. Chem. Soc.*, pp. 2603-2608, 1968.

Campochiaro et al., Retinal and Choroidal Neovascularization *Journal of Cellular Physiology*, vol./Iss: 184, pp. 301-310, Jan. 1, 2000.

Cao et al., Update on Therapeutic Neovascularization, *Cardiovascular Research*, vol./Iss: 65, pp. 639-648, Jan. 1, 2005.

Carmeliet et al., Angiogenesis in Health and Disease, *Nature Medicine*, vol./Iss: 9 (6), pp. 653-660, Jun. 1, 2003.

Carothers et al., 2-Methoxyestradiol induces p53-associated apoptosis of colorectal cancer cells, *Cancer Letters*, vol./Iss: 187, pp. 77-86, Jan. 2002.

Castagnetta, L. et al., Simple Approach to Measure Metabolic Pathways of Steroids in Living Cells, *Journal of Chromatography*, vol./Iss: 572, pp. 25-39, Dec. 6, 1991.

Chang et al., Corneal Neovascularization, *Current Opinions in Optholmology*, vol./Iss: 12, pp. 242-249, Jan. 1, 2001.

Chasserot-Golaz et al., Biotransformation of 17.beta.-hydroxy-11. beta.-(4-dimethylaminophenyl) 17.alpha.1- propynyl-estra-4,9-diene-3-one (RU486) in Rat Hepatoma Variants (Identifier only), *Biochemical Pharmacology*, vol./Iss: 46 (11), pp. 2100-2103, 1993.

Chauhan et al. 2-Methoxyestradiol and bortezomib/proteasome-inhibitor overcome dexamethasone- resistance in multiple myeloma cells by modulating Heat Shock Protein-27, *Apoptosis*, vol./Iss: 9, pp. 149-155, Jan. 1, 2004.

Chauhan et al., Mechanisms of cell death and survival in multiple myeloma (MM):Therapeutic implications, *Apoptosis*, vol./Iss: 8 (4), pp. 337-343, Jan. 2003.

Chauhan et al., Superoxide-dependent and -independent mitochondrial signaling during apoptosis in multiple myeloma cells, *Oncogene*, vol./Iss: 22, pp. 6296-6300, Jan. 2003.

Chauhan et al., 2-Methoxyestradiol overcomes drug resistance in multiple myeloma cells, *Blood*, vol./Iss: 100 (6), pp. 2187-2194, Sep. 15, 2002.

Chen et al., A New Synthetic Route to 2- and 4-Methoxyestradiols by Nucleophilic Substitution, *Steroids*, vol./Iss: 47 (1), pp. 63-66, Jan. 1986.

Chen et al., Synthesis of 11.beta.-(4-dimethylaminophenyl)-17.beta-hydroxy-17.alpha.-(1-propynyl) estra-4, 9-dien-3-one (RU486) (Identifier only), Nanjing Yaoxueyuan Xuebao, vol./Iss: 17 (4), pp. 282-285, 1986.

Cleveland et al., A Radical Approach to Treatment, *Nature*, vol./Iss: 407, pp. 309-311, Sep. 21, 2000.

Cohen et al., Novel Total Synthesis of (+)-Estrone 3-Methyl Ether, (+)-13β-Ethyl-3- methoxygona-1,3,5(10)-trien-17-one, and (+)-Equilenin 3-Methyl Ether, *The Journal of Organic Chemistry*, vol./Iss: 40 (6), pp. 681-685, Mar. 21, 1975.

Collins et al., The Structure and Function of Estrogens. XI. Synthesis of (+/−)-7(8-11α) *abeo*-Estradiol and its 9,11-Didehydro Derivative, *Aust. Journal of Chemistry*, vol./Iss: 45 (1), pp. 71-97, 1992.

Corey et al., Applications of N,N-Dimethylhydrazones to Synthesis. Use in Efficient, Positionally and Stereochemically Selective C-C Bond Formation; Oxidative Hydrolysis to Carbonyl Compounds, *Tetrahedron Letters*, vol./Iss: 1, pp. 3-6, 1976.

Corey et al., Facile Conversion of N,N-Dimethylhydrazones to Cabonyl Compounds by Cupric Ion-Catalyzed Hydrolysis, *Tetrahedron Letters*, vol./Iss: 41, pp. 3667-3668, 1976.

Crabbe, P. Cotton Effect of the Styrene Chromophore (Abstract only), *Chem. Ind*, vol./Iss: 27, pp. 917-918, 1969.

Crum, R. et al., A New Class of Steroids Inhibits Angiogenesis in the Presence of Heparin or a Heparin Fragment, *Science*, vol./Iss: 230, pp. 1375-1378, Dec. 20, 1985.

Cummings et al., Apoptosis, *The American Journal of Surgical Pathology*, vol./Iss: 21 (1), pp. 88-101, 1997.

Cursiefen et al., Angiogenesis in Corneal Disease: Histopathologic Evaluation of 254 Human Corneal Buttons with Neovascularization, *Cornea*, vol./Iss: 17 (6), pp. 611-613, Nov. 1, 1998.

Cushman et al., Synthesis, Antitubulin and Antimitotic Activity, and Cytotoxicity of Analogs of 2-Methoxyestradiol, an Endogenous Mammalian Metabolite of Estradiol that Inhibits Tubulin Polymerization by Binding to the Colchicine Binding Site, *Journal of Medicinal Chemistry*, vol./Iss: 38 (12), pp. 2041-2049, Jun. 9, 1995.

Cushman et al., Synthesis of Analogs of 2-Methoxyestradiol with Enhanced Inhibitory Effects on Tubulin Polymerization and Cancer Cell Growth, *Journal of Medicinal Chemistry*, vol./Iss: 40 (15), pp. 2323-2334, 1997.

D'Amato et al., 2-Methoxyestradiol, an Endogenous Mammalian Metabolite, Inhibits Tubulin Polymerization by Interacting at the Colchicine Site, *Proceedings of the National Academy of Science USA*, vol./Iss: 91, pp. 3964-3968, Apr. 26, 1994.

D'Amato, R.J. et al., Thalidomide is an Inhibitor of Angiogenesis, *Proceedings of the National Academy of Science USA*, vol./Iss: 91, pp. 4082-4085, Apr. 1, 1994.

D'Amore et al., Mechanisms of Angiogenesis, *Annual Review of Physiology*, vol./Iss: 49, pp. 453-464, Jan. 1, 1987.

Danis et al., Anti-Angiogenic Therapy of Proliferative Diabetic Retinopathy, *Expert Opinion in Pharmacotherapy*, vol./Iss: 2 (3), pp. 395-407, Mar. 1, 2001.

Davoodpour et al., Effects of 2-methoxyestradiol on proliferation, apoptosis and PET-tracer uptake in human prostate cancer cell aggregates, *Nuclear Medicine and Biology*, vol./Iss: 31, pp. 867-874, Jan. 1, 2004.

Dawling et al., In Vitro Model Differences of Mammary Estrogen Metabolism: Structural and Kinetic between Catechol Estrogens 2- and 4-Hydroxyestradiol, *Chem. Res. Toxicol.*, vol./Iss: 17, pp. 1258-1264, Jan. 1, 2004.

Dawling et al., Methoxyestrogens Exert Feedback Inhibition on Cytochrome P450 and I A1 and IB1, *Cancer Research*, vol./Iss: 63, pp. 3127-3132, Jun. 15, 2003.

Day et al., The effects of 2-substituted oestrogen sulphamates on the growth of prostate and ovarian cancer cells, *Journal of Steroid Biochemistry & Molecular Biology*, vol./Iss: 84, pp. 317-325, Jan. 2003.

De Bono et al., The Future of Cytotoxic Therapy: Selective Cytotoxicity Based on Biology is the Key, *Breast Cancer Research*, vol./Iss: 5 (3), pp. 154-159, Mar. 27, 2003.

De Laey et al., Hyperlipofuscinosis and Subretinal Fibrosis in Stargardt's Disease, *Retina*, vol./Iss: 15 (5), pp. 399-406, Jan. 1, 1995.

Ding et al., Sex Hormone-Binding Globulin Mediates Prostate Androgen Receptor Action via a Novel Signaling Pathway, *Endocrinology*, vol./Iss: 139 (1), pp. 213-218, 1998.

Dingli et al., Promising Preclinical Activity of 2-Methoxyestradiol in Multiple Myeloma, *Clinical Cancer Research*, vol./Iss: 8, pp. 3948-3954, Dec. 1, 2002.

Djavaberi-Mergny et al., TNFα Potentiates 2-Methoxyestradiol-Induced Mitochondrial Death Pathway, *Annals New York Academy of Sciences*, vol./Iss: 1010, pp. 159-162, Jan. 2003.

Dobos et al., In Vitro and In Vivo Antitumor Effect of 2-Methoxyestradiol on Human Melanoma, *International Journal of Cancer*, vol./Iss: 112, pp. 771-776, Jan. 1, 2004.

Dubey et al., Methoxyestradiols Mediate the Antimitogenic Effects of Estradiol on Vascular Smooth Muscle Cells via Estrogen Receptor-Independent Mechanisms, *Biochemical and Biophysical Research Communications*, vol./Iss: 278, pp. 27-33, 2000.

Dubey et al., Cardiovascular Pharmacology of Estradiol Metabolites, *The Journal of Pharmacology and Experimental Therapeutics*, vol./Iss: 308 (2), pp. 403-409, Jan. 1, 2004.

Dubey et al., Catecholamines Block the Antimitogenic Effect of Estradiol on Human Glomerular Mesangial Cells, *Hypertension*, vol./Iss: 42, pp. 349-355, Jan. 2003.

Dubey et al., Mexthoxyestradiols Mediate the Antimitogenic Effects of Locally Applied Estradiol on Cardiac Fibroblast Growth, *Hypertension*, vol./Iss: 39 (Part 2), pp. 412-417, Feb. 2002.

Dubey et al., Role of Methoxyestradiols in the Growth Inhibitory Effects of Estradiol on Human Glomerular Mesangial Cells, *Hypertension*, vol./Iss: 39 (Part 2), pp. 418-424, Feb. 2002.

Dubey et al., Estradiol Metabolites Inhibit Endothelin Synthesis by an Estrogen Receptor-Independent Mechanism, *Hypertension*, vol./Iss: 37 Part 2, pp. 640-644, Feb. 1, 2001.

Durani et al., Seco-Oestradiols and Some Non-Steroidal Oestsrogens: Structural Correlates of Oestrogenic Action, *Journal of Steroid Biochemistry*, vol./Iss: 11, pp. 67-77, 1979.

Dvir et al., Thin-layer Chromatography of DANSYL-oestrogens, *Journal of Chromatography*, vol./Iss: 52, pp. 505-506, Nov. 4, 1970.

Edsall et al., Effects of Altering the Electronics of 2-Methoxyestradiol on Cell Proliferation, on Cytotoxicity in Human Cancer Cell Cultures, and on Tubulin Polymerization, *Journal of Medicinal Chemistry*, vol./Iss: 47, pp. 5126-5139, Jan. 1, 2004.

El-Tombary, Synthesis, Uterotropic, and Antiuterotrophic Activities of Some Estradiol Derivatives Containing Thiadiazole, Thiazoline, aNd Thiazolidinone Moieties, *Arch. Pharm. Pharm. Med. Chem.*, vol./Iss: 330 (9-10), pp. 295-302, 1997.

Emons et al., Modulation der hypophysaren Sekretion von Luteinisierendem Hormon (LH) durch Ostrogene, *FOCUS MHI*, vol./Iss: 3, pp. 221-228, 1986.

Epe et al., Microtubular Proteins as Cellular Targets for Carcinogenic Estrogens and Other Carcinogens, *Mechanisms of Chromosome Distribution and Aneuploidy*, pp. 345-351, 1989.

Evans et al., A Convergent Total Synthesis of +/− Colchicine and +/− Desacetamidoisocolchicine, *Journal of the American Chemical Society*, vol./Iss: 103, pp. 5813-5821, Sep. 23, 1981.

Fajardo et al., Effects of Genistein and 2-Methoxyestradiol on Matrix Matalloproteinases and their Inhibitors Secreted by Ehrlich Ascites Tumor Cells, *Anticancer Research*, vol./Iss: 20, pp. 1691-1694, Jan. 1, 2000.

Fanchenko et al., Characterisitics of the guinea pig uterus estrogen receptor system (Abstract only), *Byull. Eksp. Biol. Med.*, vol./Iss: 85 (4), pp. 467-470, 1978.

Farmer et al., Retinal Vasculitis Associated with Autoantibodies to Sjogren's Syndrome A Antigen (Abstract only), *American Journal of Ophthalmology*, vol./Iss: 100 (6), pp. 814-821, Dec. 1, 1985.

Feher et al., Multiple Flexible Alignment with SEAL: A Study of Molecules Acting on the Colchicine Binding Site, *Journal of Chemical Information and Computer Sciences*, vol./Iss: 40, pp. 495-502, Jan. 1, 2000.

Fetizon et al., Synthesis of 2-keto steroids (Abstract only), *Bull. Soc. Chim. FR.*, vol./Iss: 8, pp. 3301-3306, 1968.

Fevig et al., A Short, Stereoselective Route to 16α-(Substituted-alkyl)estradiol Derivatives, *Journal of Organic Chemistry*, vol./Iss: 52, pp. 247-251, 1987.

Field et al., Effect of Thalidomide on the Graft versus Host Reaction, *Nature*, vol./Iss: 211 (5055), pp. 1308-1310, Sep. 17, 1966.

Fieser et al., N-Methylformanilide, *Organic Synthesis Collective* vol. 3, vol./Iss: 3, pp. 590-591, 1955.

Figg et al., Inhibition of angiogenesis: treatment options for patients with metastatic prostate cancer, *Investigational New Drugs*, vol./Iss: 20, pp. 183-194, Jan. 2002.

Fishman, J. Synthesis of 2-Methoxyestrogens, *Journal of the American Chemical Society*, vol./Iss: 80, pp. 1213-1216, Mar. 5, 1958.

Fitzgerald, Molecular Features of Colchicine Associated with Antimitotic Activity and Inhibition of Tubulin Polymerization, *Biochemical Pharmacology*, vol./Iss: 25 (12), pp. 1383-1387, Jun. 15, 1976.

Flohe et al., Studies on the Hypothetical Relationship of Thalidomide-induced Embryopathy and Collagen Biosynthesis, *Arzneimitte/Forschung* (Germany West), vol./Iss: 31 (2), pp. 315-320, Jan. 1, 1981.

Folkman et al., Angiogenesis Inhibition and Tumor Regression Caused by Heparin or a Heparin Fragment in the Presence of Cortisone, *Science*, vol./Iss: 221, pp. 719-725, Aug. 19, 1983.

Folkman, J., Tumor Angiogenesis: Therapeutic Implications, *New England Journal of Medicine*, vol./Iss: 285 (21), pp. 1182-1186, Nov. 18, 1971.

Folkman, J. et al., Induction of Angiogenesis During the Transition from Hyperplasia to Neoplasia, *Nature*, vol./Iss: 339, pp. 58-61, May 4, 1989.

Folkman, J. et al., Tumor Behavior in Isolated Perfused Organs in vitro Growth and Metastases of Biopsy Material in Rabbit Thyroid and Canine Intestinal Segment, *Annals of Surgery*, vol./Iss: 164(3), pp. 491-502, Sep. 1, 1966.

Fotsis et al., The Endogenous Oestrogen Metabolite 2-Methoxyoestradiol Inhibits Angiogenesis and Suppresses Tumour Growth, *Nature*, vol./Iss: 368, pp. 237-239, Mar. 17, 1994.

Fraser et al., Angiogenesis and Its Control in the Female Reproductive System (Abstract only), *British Medical Bulletin*, vol./Iss: 56 (3), pp. 787-797, 2000.

Friedlander et al., Involvement of Integrins αvβ3 and αvβ5 in Ocular Neovascular Diseases, *Proceedings of the National Academy of Science (USA)*, vol./Iss: 93, pp. 9764-9769, Sep. 1, 1996.

Gadosy et al., Generation, Characterization, and Deprotonation of Phenol Radical Cations, *Journal of Physical Chemistry*, vol./Iss: 103, pp. 8834-8839, 1999.

Gandhi et al., Mannich Reaction of Estrone, *Journal of Indian Chem. Soc.*, vol./Iss: 39, pp. 306-308, 1962.

Gaslini et al., Reaction of Eugenol with Synthesis Gas. Synthesis of 5,6,7,8-Tetrahydro-3-methoxy-2-napthol, *Journal of Organic Chemistry*, vol./Iss: 29 (5), pp. 1177-1180, May 1964.

Genentech USA, VEGF may be main cause of diabetic retinopathy (Abstract only), *Biotechnology Newswatch*, pp. 13-14, Oct. 17, 1994.

Getahun et al., Synthesis of Alkoxy-Substituted Diaryl Compounds and Correlation of Ring Separation with Inhibition of Tubulin Polymeriztation: Differential Enhancement of Inhibitory Effects Under Suboptimal Polymerization Reaction Conditions, *Journal of MedicinalChemistry*, vol./Iss: 35 (6), pp. 1058-1067, Mar. 20, 1992.

Gian Tondury et al., Zur Wirkung Der Sexualhormone Auf Wachstum und Differenzierung (See English Summary p. 55), *Cambridge Philosophical Society*, pp. 28-58, Dec. 17, 1955.

Gimbrone, M.A. et al., Tumor Growth and Neovascularization: An Experimental Model Using the Rabbit Cornea, *Journal of the National Cancer Institute*, vol./Iss: 52(2), pp. 413-419, Feb. 1, 1974.

Gimbrone, M.A. et al., Tumor dormancy in vivo by Prevention of Neovascularization, *Journal of Experimental Medicine*, vol./Iss: 136, pp. 261-276, Jan. 1, 1972.

Gleichmann et al., Immunoblastic Lymphadenopathy, Systemic Lupus Erythematosus, and Related Disorders. Possible Pathogenetic Pathways. (Abstract only), *American Journal of Pathology*, vol./Iss: 72 (4), pp. 708-723, Oct. 1, 1979.

Gonzalez et al., Synthesis and Pharmacological Evaluation of 8α-Estradiol Derivatives, *Steroids*, vol./Iss: 40 (2), pp. 171-187, Aug. 1, 1982.

Gross et al., Inhibition of Tumor Growth, Vascularization, and Collagenolysis in the Rabbit Cornea by Medroxyprogesterone, *Procedings of the National Academy of Science USA*, vol./Iss; 78 (2), pp. 1176-1180, Feb. 1981.

Gros, J.L. et al., Modulation of Solid Tumor Growth in vivo by bFGF (Abstract only), *Proceedings of the American Association of Cancer Research*, vol./Iss: 31, pp. 79, Mar. 1, 1990.

Gujjar et al., The Effect of Estradiol on *Candida albicans*, Growth, *Annals of Clinical and Laboratory Science*, vol./Iss: 27 (2), pp. 151-156, 1997.

Gunzler, V., Thalidomide-A Therapy for the Immunological Consequences of HIV Infection?, *Medical Hypothesis*, vol./Iss: 30 (2), pp. 105-109, Oct. 1989.

Gupta et al., Antifertility Agents. XIV. Secosteroids. VII. Synthesis of 2α- and 2β, 6β-dimethyl- 3β-(p-hyroxyphenyl)-trans-bicyclo[4.3.0]nonan-7-ones and some related compounds (Abstract only), *Indian Journal of Chemistry*, vol./Iss: 13 (7), pp. 759-760, 1975.

Gupta et al., Studies in Antifertility Agents. Part XVIII. 2α,6β-Diethyl-3β-(p-hydroxyphenyl)-trans-bicyclo[4.3.0]nonan-7β-ol and 6β-methyl-3β-(p-hydroxphenyl)-2α-propyl- trans-bicyclo[4.3.0]nonan-7β-ol (Abstract only), *Indian Journal of Chemistry*, vol./Iss: 19B (10), pp. 886-890, 1980.

Gutierrez-Rodriguez et al., Treatment of Refractory Rheumatoid Arthritis—The Thalidomide Experience, *The Journal of Rheumatology*, vol./Iss: 16 (2), pp. 158-163, Feb. 1989.

Gutierrez-Rodriguez, O., Thalidomide—A Promising New Treatment for Rheumatoid Arthritis, *Arthritis and Rheumatism*, vol./Iss: 27 (10), pp. 1118-1121, Oct. 1984.

Hagen et al., Inhibition of mitochondrial respiration by the anticancer agent 2-methoxyestradiol, *Biochemical and Biophysical Research Communications*, vol./Iss: 322, pp. 923-929, Jan. 1, 2004.

Hahnel et al., The Specificity of the Estrogen Receptor of Human Uterus, *Journal of Steroid Biochemistry*, vol./Iss: 4, pp. 21-31, 1973.

Hajjar et al., New Concepts in Fibrinolysis and Angiogenesis (Abstract only), *Current Atherosclerosis Reports*, vol./Iss: 2 (5), pp. 417-421, Sep. 1, 2000.

Haldar et al., Bc12 is the Guardian of Microtubule Integrity, *Cancer Research*, vol./Iss: 57, pp. 229-233, Jan. 15, 1997.

Hamanaka et al., Retinal Ischemia and Angle Neovascularization in Proliferative Diabetic Retinopathy (Abstract only), *American Journal of Ophthalmology*, vol./Iss: 132 (5), pp. 648-658, Nov. 1, 2001.

Hamel et al., Interactions of 2-Methoxyestradiol, an Endogenous Mammalian Metabolite, with Unpolymerized Tubulin and with Tubulin Polymers, *Biochemistry*, vol./Iss: 35 (4), pp. 1304-1310, 1996.

Hammers et al., Introduction of a novel proliferation assay for pharmacological studies allowing the combination of BrdU detection and phenotyping, *Journal of Immunological Methods*, vol./Iss: 264, pp. 89-93, Jan. 2002.

Hammond et al., Structure/function analyses of human sex hormone-binding globulin: effects of zinc on steroid-binding specificity, *Steroid Biochemistry & Molecular Biology*, vol./Iss: 85, pp. 195-200, Jan. 2003.

Han et al., Dehydroepiandrosterone and Dihydrotestosterone Recognition by Human Estrogenic 17β-Hydroxysteroid Dehydrogenase, *Journal of Biological Chemistry*, vol./Iss: 275, Iss. 2, pp. 1105-1111, Jan. 14, 2000.

Handley et al., Chronic bullous disease of childhood and ulcerative colitis, *British Journal of Dermatology*, vol./Iss: 127 (40), pp. 67-68, Jul. 1, 1992.

Hartley-ASP et al., Diethylstilbestrol Induces Metaphase Arrest and Inhibits Microtubule Assembly, *Mutation Research*, vol./Iss: 143 (4), pp. 231-235, Aug. 1985.

He et al., A Versatile Synthesis of 2-Methoxyestradiol, an Endogenous Metabolite of Estradiol which Inhibits Tubulin Polymerization by Binding to the Colchicine Biding Site, *Bioorganic & Medicinal Chemistry Letters*, vol./Iss: 4 (14), pp. 1724-1728, 1994.

He et al., Novel Cytokine Release Inhibitors, Part II: Steroids, *Bioorganic & Medicinal Chemistry Letters*, vol./Iss: 8, pp. 2825-2828, 1998.

Hejaz et al., Synthesis and Biological Activity of the Superestrogen (E)-17-Oximino-3-O-sulfamoyl-1,3,5(10)-estratriene: X-ray Crystal Structure of (E)-17-Oximino-3-hydroxy-1,3,5(10)-estratriene, *Journal of Medicinal Chemistry*, vol./Iss: 42 (16), pp. 3188-3192, 1999.

Heney et al., Thalidomide treatment for chronic graft-versus-host disease, *British Journal of Haematology*, vol./Iss: 78 (1), pp. 23-27, May 1991.

Hill et al., Pathogenesis of Ptergium (Abstract only), *Eve*, vol./Iss: 3 (Pt 2), pp. 218-226, Jan. 1, 1990.

Himes et al., Action of the Vinca Alkaloids Vincristine, Vinblastine, and Desacetyl Vinblastine Amide on Microtubules in Vitro, *Cancer Research*, vol./Iss: 36, pp. 3798-3802, Oct. 1976.

Ho, Shuk-Mei, Estrogens and Anti-Estrogens: Key Mediators of Prostate Carcinogenesis and New Therapeutic Candidates, *Journal of Cellular Biochemistry*, vol./Iss: 91, pp. 491-503, Jan. 1, 2004.

Holden et al., Mitotic Arrest by Benzimidazole Analogs in Human Lymphocyte Cultures, *Environmental Mutagenesis*, vol./Iss: 2, pp. 67-73, 1980.

Holker et al., The Reactions of Estrogens with Benzeneseleninic Anhydride and Hexamethyldisilazane, *J. Chem. Soc. Perkin Trans.*, vol./Iss: I, pp. 1915-1918, 1982.

Hori, A. et al., Suppression of Solid Tumor Growth by Immunoneutralizing Monoclonal Antibody Against Human Basic Fibroblasts Growth Factor, *Cancer Research*, vol./Iss: 51, pp. 6180-6184, Nov. 15, 1991.

Hu et al., Interleukin-8 Stimulates Angiogenesis in Rats, *Inflammation*, vol./Iss: 17 (2), pp. 135-143, Apr. 1, 1993.

Hu, G., Neomycin Inhibits Angiogenin-induced Angiogenesis (Abstract only), *Proceedings of the National Academy of Sciences. USA*, vol./Iss: 95 (17), pp. 9791-9795, 1998.

Huang et al., Superoxide Dismutase as a Target for the Selective Killing of Cancer Cells, *Nature*, vol/Iss: 407 (6802), pp. 390-395, Sep. 21, 2000.

Huber et al., Tubulin Binding of Conformationally Restricted Bis-Aryl Compounds, *Bioorganic & Medicinal Chemistry Letters*, vol./Iss: 1 (5), pp. 243-246, 1991.

Hughes et al., 2-Methoxyestradiol and Analogs as Novel Antiproliferative Agents: Analysis of Three Dimensional Quantitative Structure-Activity Relationships for DNA Synthesis Inhibition and Estrogen Receptor Binding, *Molecular Pharmacology*, vol./Iss: 61 (5), pp. 1053-1069, Jan. 1, 2002.

Huober et al., Oral Administration of an Estrogen Metabolite-Induced Potentiation of Radiation Antitumor Effects in Presence of Wild-Type p53 in Non-Small-Cell Lung Cancer, *International Journal of Radiation Oncology Biology, Physics*, vol./Iss: 48 (4), pp. 1127-1137, Jan. 1, 2000.

Ikegawa et al., Immunoaffinity Extraction for Liquid Chromatographic Determination of Equilin and Its Metabolitesin Plasma (Abstract only), *Biomed. Chromatogr.*, vol./Iss: 10 (2), pp. 73-77, 1996.

Imamura et al., Method for Manufacture of Dihydrc Phenols (Abstract only), USPATFULL 76:20259 US 3,950,437, Apr. 13, 1976.

Ingber, D. et al., Synthetic analogues of fumagillin that inhibit angiogenesis and suppress tumor growth, *Nature*, vol./Iss: 348, pp. 555-557, Dec. 6, 1990.

Inoue et al., Molecular Mechanism of Diclofenac-Induced Apoptosis of Promyelocytic Leukemia: Dependency on Reactive Oxygen Species, AKT, BID, Cytochrome c, and Caspase Pathway, *Free Radical Biology & Medicine*, vol./Iss: 37 (8), pp. 1290-1299, Jan. 1, 2004.

Ireson et al., Pharmacokinetics and efficacy of 2-methoxyestradiol and 2-methoxyestradiol- bis-sulphamate in vivo in rodents, *British Journal of Cancer*, vol./Iss: 90, pp. 932-937, Jan. 1, 2004.

Iriarte et al., Steroids (XCIV). Synthesis of 2-methyl and 1,2-dimethyl estrogens (Abstract only), *Tetrahedron*, vol./Iss: 3, pp. 28-36, 1958.

Jackson et al., The Codependence of Angiogenesis and Chronic Inflammation, *The FASEB Journal*, Abstract only, vol./Iss: 11, pp. 457-465, Jan. 1, 1997.

Jaggers et al., Potent Inhibitory Effects of Steroids in an in vitro Model of Angiogenesis (Abstract only), *Journal of Endocrinology*, vol./Iss: 150 (3), pp. 457-464, 1996.

Jampol et al., Peripheral Proliferation Retinopathies: An Update on Angiogenesis, Etiologies and Management (Abstract only), *Survey of Ophthalmology*, vol./Iss: 38 (6), pp. 519-540, May 1, 1994.

Jhingran et al., Studies in Antifertility Agents—Part XLI: Secosteroids-x: Syntheses of Various Stereoisomers of (+−)-2,6β-diethyl-7α-ethynyl-3-(p-hydroxyphenyl)-trans-bicyclo [4.3.0)nonan-7β-ol, *Steroids*, vol./Iss: 42 (6), pp. 627-634, 1983.

Josefsson et al., Suppression of Type II Collagen-Induced Arthritis by the Endogenous Estrogen Metabolite 2-Methoxyestradiol, *Arthritis & Rheumatism*, vol./Iss: 40 (1), pp. 154-163, Jan. 1997.

Jozsef, Timar, Beszamolo a Nemzeti Onkologiai Kutatas-fejlesztesi Konzorcium 2003. evitevekenysegerol (Abstract in English)(Abstract only), *Magyaa Onkologusok Tarsasaga*, vol./Iss: 48, pp. 75-79, Jan. 1, 2004.

Kabarity et al., Further Investigations on the cytological effects of some contraceptives, *Mutation Research*, vol./Iss: 135, pp. 181-188, 1984.

Kachadourian et al., 2-Methoxyestradiol Does Not Inhibit Superoxide Dismutase, *Archives of Biochemistry and Biophysics*, vol./Iss: 392 (2), pp. 349-353, Aug. 15, 2001.

Kahlon et al., Angiogenesis in Atherosclerosis (Abstract only), *Canadian Journal of Cardiology*, vol./Iss: 8 (1), pp. 60-64, Jan. 1, 1992.

Kalina et al., Neovascularization of the Disc in Pars Planitis (Abstract only), *Retina*, vol./Iss: 10 (4), pp. 269-273, Jan. 1, 1990.

Karbowski et al., Opposite Effects of Microtubule-Stabilizing and Microtubule-Destabilizing Drugs on Biogenesis of Mitochondria in Mammalian Cells, *Journal of Cell Science*, vol./Iss: 114 (2), pp. 281-291, Oct. 27, 2000.

Karwat, Separation and Recovery of Hydrogen Sulfide from Hydrocarbon Mixture, Caplus DE 1103310, Sep. 2, 1959.

Kataoka et al., An Agent that Increases Tumor Suppressor Transgene Product Coupled with Systemic Transgene Delivery Inhibits Growth of Metastatic Lung Cancer in Vivo (Abstract only), *Cancer Research*, vol./Iss: 58 (21), pp. 4761-4765, Nov. 1998.

Kelly et al., The Stimulation of Prostaglandin Production by Two Antiprogesterone Steroids in Human Endometrial Cells (Abstract only), *Journal of Clinical Endocrinology Metabolism*, vol./Iss: 62 (6), pp. 1116-1123, Jun. 1986.

Kim et al., Mass Spectrometric Measurement of Differential Reactivity of Cysteine to Localize Protein-Ligand Binding Sites. Application to Tubulin-Binding Drugs, *Analytical Biochemistry*, vol./Iss: 332, pp. 376-383, Jan. 1, 2004.

Kim, K.J. et al., Inhibition of Vascular Endothelial Growth Factor-induced Angiogenesis Suppresses Tumor Growth in Vivo, *Nature*, vol./Iss: 362, pp. 841-844, Apr. 29, 1993.

Kinuya et al., Improved Survival of Mice Bearing Liver Metastases of Colon Cancer Cells Treated with a Combination of Radioimmunotherapy and Antiangiogenic Therapy, *European Journal of Nuclear Medicine and Molecular Imaging*, pp. 1-11, Jan. 1, 2004.

Kiuru et al., Short synthesis of 2-methoxyestradiol and 2-hydroxyestradiol, *Steroids*, vol./Iss: 68, pp. 373-375, Jan. 2003.

Klauber et al., Inhibition of Angiogenesis and Breast Cancer in Mice by the Microtubule Inhibitors 2-Methoxyestradiol and Taxol, *Cancer Research*, vol./Iss: 57, pp. 81-86, Jan. 1, 1997.

Knighton, D. et al., Avascular and Vascular Phases of Tumour Growth in the Chick Embyo, *British Journal of Cancer*, vol./Iss: 35, pp. 347-356, Jan. 1, 1977.

Kole et al., Studies in Antifertility Agents. 11. Secosteroids.5.Synthesis of 9,11-Secoestradiol, *Journal of Medicinal Chemistry*, vol./Iss: 18 (7), pp. 765-766, 1975.

Kornmehl et al., Bilateral Keratitis in Lyme Diseases (Abstract only), *Ophthalmology*, vol./Iss: 96 (8), pp. 1194-1197, Aug. 1, 1989.

Kousteni et al., Reversal of Bone Loss in Mice by Nongenotypic Signaling of Sex Steroids, *Science*, vol./Iss: 298, pp. 843-846, Oct. 25, 2002.

Kovacs et al., Steroids. XXIII. Synthesis of 2- and 4-hydroxy and 2,4-dihydroxy derivatives of estrone and estradiol (Abstract only), *Acta Phys.Chem.*, vol./Iss: 19 (3), pp. 287-290, 1973.

Kumar et al., Title: 2-Methoxyestradiol Blocks Cell-Cycle Progression at $G_2$/M Phase and Inhibits Growth of Human Prostate Cancer Cells, *Molecular Carcinogenesis*, vol./Iss: 31, pp. 111-124, Jan. 1, 2001.

Kurebayashi et al., Paradoxical Hormone Responses KPL-1 Breast Cancer Cells in vivo: a Significant Role of Angiogenesis in Tumor Growth (Abstract only), *Oncology*, vol./Iss: 59 (2), pp. 158-165, 2000.

Lakhani et al., Determination of the Antiangiogenesis Agent 2-Methoxyestradiol in Human Plasma by Liquid Chromatography with Ultraviolet Radiation, *Journal of Chromatography B*, vol./Iss: 806, pp. 289-293, Jan. 1, 2004.

Lambert et al., 2-Methoxyestradiol Induces Caspase-Independent Mitochondria-Centered Apoptosis in DS-Sarcoma Cells, *International Journal of Cancer*, vol./Iss: 108, pp. 493-501, Jan. 1, 2004.

Lavallee et al., 2-Methoxyestradiol Up-Regulates Death Receptor 5 and Induces Apoptosis through Activation of the Extrinsic Pathway, *Cancer Research*, vol./Iss: 63, pp. 468-475, Jan. 15, 2003.

Lavallee et al., 2-Methoxyestradiol Inhibits Proliferation and Induces Apoptosis Independently of Estrogen Receptors α and β, *Cancer Research*, vol./Iss: 62, pp. 3691-3697, Jul. 1, 2002.

Lavigne et al., The Effects of Catechol-*O*-Methyltransferase Inhibition on Estrogen Metabolite and Oxidative DNA Damage Levels in Estradiol-Treated MCF-7 Cells, *Cancer Research*, vol./Iss: 61, pp. 7488-7494, Oct. 15, 2001.

Le Bras, J. et al., Activation and Regioselective Ortho-Functionalization of the A-Ring of B-Estradiol Promoted by "Cp*Ir": An Efficient Organometallic Procedure for the Synthesis of 2-Methoxyestradiol, *Organometallics*, vol./Iss: 16, pp. 1765-1771, 1997.

Lee et al., Inhibition of Growth and Angiogenesis of Human Neurofibrosarcoma by Heparin and Hydrocortisone (Abstract only), *Journal of Neurosurgery*, vol./Iss: 73 (3), pp. 429-435, Sep. 1, 1990.

Lee et al., Ocular Neovascularization: An Epidemiologic Review, *Survey of Ophthalmology*, vol./Iss: 43 (3), pp. 245-269, Nov. 1, 1998.

Leveille et al., Platelet-Induced Retinal Neovascularization in Leukemia (Abstract only), *American Journal of Ophthalmology*, vol./Iss: 91 (5), pp. 640-644, May 1, 1981.

Lewis, Richard J., *Hawley's Condensed Chemical Dictionary*, pp. 577, Jan. 1993.

Lewis, Richard J., *Hawley's Condensed Chemical Dictionary*, pp. 128-129, Jan. 1993.

Li et al., Antitumor Activities of 2-Methoxyestradiol on Cervical and Endometrial Cancers in Vitro and In Vivo, *Dissertations from the Faculty of Medicine-Uppsala*, vol./Iss: 1374, pp. 11-62, Jan. 1, 2004.

Li, J., et al., (DN 103:65176) Catechol Formation of Fluoro- and Bromo-substituted Estradiols by Hamster Liver Microsomes. Evidence for Dehalogenation. (Abstract only), *CAPLUS: Molecular Pharmacology*, vol./Iss: 27 (5), pp. 559-565, 1985.

Lien, W. et al., The blood supply of experimental liver metastases. II. A Microcirculatory study of the normal and tumor vessels of the liver with the use of perfused silicone rubber, *Surgery*, vol./Iss: 68 (2), pp. 334-340, Aug. 1970.

Limantsev et al., Effect of some estrogen structural analogs on the development of the mouse embyo (Abstract only), *Akush Jinekol*, (Chemical Abstracts 97:85606), vol./Iss: 6, pp. 55-56, 1982.

Lin et al., Interactions of Tubulin with Potent Natural and Synthetic Analogs of the Antimitotic Agent Combretastatin: A Structure-Activity Study, *Molecular Pharmacology*, vol./Iss: 34 (2), pp. 200-208, Aug. 1988.

Lin et al., A Comparative Study on the Effects of 2,3,7,8,-Tetrochlorodibenzo-*p*-Dioxin Polychlorinated Biphenyl126 and Estrogen in Human Bronchial Epithelial Cells, *Toxicology and Applied Pharmacology*, vol./Iss: 195, pp. 83-91, Jan. 1, 2004.

Lin et al., 2-Methoxyestradiol-Induced Caspace-3 Activation and Apoptosis Occurs Through $G_2$/M Arrest Dependent and Independent Pathways in Gastric Carcinoma Cells, *Cancer*, vol./Iss: 92, pp. 500-509, Aug. 1, 2001.

Lin et al., Comparison of 2-Methoxyestradiol-Induced, Docetaxel-Induced, and Paclitaxel-Induced Apoptosis in Hepatoma Cells and Its Correlation with Reactive Oxygen Species, *Cancer*, vol./Iss: 89 (5), pp. 983-994, Sep. 1, 2000.

Lincoln et al., Conformation of Thiocolchicine and Two B-Ring-Modified Analogues Bound to Tubulin Studied with Optical Spectroscopy, *Biochemistry*, vol./Iss: 30 (5), pp. 1179-1187, Feb. 5, 1991.

Lippert et al., The effects of A-ring and D-ring metabolites of estradiol on the proliferation of vascular endothelial cells, *Life Sciences*, vol./Iss: 67, pp. 1653-1658, 2000.

Lippert et al., The Impact of Endogenous Estradiol Metabolites on Carcinogenesis, *Steroids*, vol./Iss: 65, pp. 357-369, Jan. 1, 2000.

Lis et al., 2-Methoxyestradiol Inhibits Proliferation of Normal and Neoplastic Glial Cells, and Induces Cell Death, In vitro, *Cancer Letters*, vol./Iss: 213, pp. 57-65, Jan. 1, 2004.

Liu et al., Total Synthesis of (+−) -$D^{9(12)-}$ Capnellene, *Tetrahedron Letters*, vol./Iss: 26 (40), pp. 4847-4850, 1985.

Liu et al., Concentration-Dependent Mitogenic and Antiproliferative Actions of 2-Methoxyestradiol in Estrogen Receptor-Positive Human Breast Cancer Cells, *Steroid Biochemistry & Molecular Biology*, vol./Iss: 88, pp. 265-275, Jan. 1, 2004.

Liu et al., Inhibitory Action of ICI-182,780, an Estrogen Receptor Antagonist, on $BK_{Ca}$ Channel Activity in Cultured Endothelial Cells of Human Coronary Artery, *Biochemical Pharmacology*, vol./Iss: 66, pp. 2053-2063, Jan. 2003.

Locci et al., Angiogenesis: A New Diagnostic Aspect of Obstetric and Gynecologic Echography, *Journal of Perinatal Medicine*, vol./Iss: 21 (6), pp. 453-473, Jan. 1, 1993.

Loozen et al., An Approach to the Synthesis of 7.beta.-amino Estrogens (Abstract only), Reel.: J.R. *Neth.Chem. Soc.*, vol./Iss: 102 (10), pp. 433-437, 1983.

Lottering et al., Effects of the 17β-Estradiol Metabolites on Cell Cycle Events in MCF-7 Cells (Chemical Abstracts Doc. No: 117:245769, 1992), *Cancer Research*, vol./Iss: 52, pp. 5926-5932, Nov. 1, 1992.

Lottering et al., 17β-Estradiol Metabolites Affect Some Regulators of the MCF-7 Cell Cycle, *Cancer Letters*, vol./Iss: 110, pp. 181-186, 1996.

Lovely et al., 2-(Hydroxyalkyl)estradiols: Synthesis and Biological Evaluation, *Journal of Medicinal Chemistry*, vol./Iss: 39, pp. 1917-1923, 1996.

Lui et al., Male Predominance in Hepatocellular Carcinoma: New Insight and a Possible Therapeutic Alternative, *Medical Hypothesis*, vol./Iss: 55 (4), pp. 348-350, Jan. 1, 2000.

Luo et al., Effect of Components of Crown Ether Copper(I)Iodide Mixed Catalyst on Nucleophilic Substitution of Bromoestrogen (Abstract No. 195225)(Abstract only), *Chemical Abstracts*, vol./Iss: 111 (21), pp. 818, col. 1, Nov. 20, 1989.

Mabjeesh et al., 2ME2 Inhibits Tumor Growth and Angiogenesis by Disrupting Microtubules and Dysregulating HIF, *Cancer Cell*, vol./Iss: 3, pp. 363-375, Apr. 1, 2003.

MacCarthy-Morrogh, Differential Effects of Estrone and Estrone-3-*O*-Sulfamate Derivatives on Mitotic Arrest, Apoptosis, and Microtubule Assembly in Human Breast Cancer Cells, *Cancer Research*, vol./Iss: 60, pp. 5441-5450, Oct. 1, 2000.

MacEwen et al., 2-Methoxyestradiol (2ME2): In Vitro Apoptosis and Cell Cycle Inhibition and In Vivo Antitumor Activity in Canine Spontaneous Tumors, *American Association for Cancer Research—92nd Annual Meeting*, Abstract #20, Mar. 24, 2001.

Mahadevan et al., Metastasis and Angiogenesis, *Acta Oncologica*, vol./Iss: 29 (1), pp. 97-103, Jan. 1, 1990.

Manfredi et al., Taxol: An Antimitotic Agent with a New Mechanism of Action, *Pharmacology & Therapeutics*, vol./Iss: 25 (1), pp. 83-125, 1984.

Mann et al., Choroidal Neovascularization with Granulomatous Inflammation in Ocular Histoplasmosis Syndrome (Abstract only), *American Journal of Ophthalmology*, vol./Iss: 130 (2), pp. 247-250, Aug. 1, 2000.

Maran et al., 2-Methoxyestradiol Induces Interferon Gene Expression and Apoptosis in Osteosarcoma Cells, *Bone*, vol./Iss: 30 (2), pp. 393-398, Feb. 2002.

Maro et al., Mechanism of Polar Body Formation in the Mouse Oocyte: An Interaction Between the Chromosomes, the Cytoskeleton and the Plasma Membrane, *Journal of Embryology and Experimental Morphology*, vol./Iss: 92, pp. 11-32, 1986.

Maro et al., Changes in Actin Distribution During Fertilization of the Mouse Egg, *Journal of Embryology and Experimental Morphology*, vol./Iss: 81, pp. 211-237, 1984.

Marti et al., Hypoxia-Induced Vascular Endothelial Growth Factor Expression Precedes Neovascularization after Cerebral Ischemia (Abstract only), *American Journal of Pathology*, vol./Iss: 156 (3), pp. 965-976, Mar. 1, 2000.

Matsunaga et al., Angiogenesis from the Eighth Cranial Nerve to Vestibular Schwannomas (Abstract only), *Acta Otolaryngology*, vol./Iss: 116 (1), pp. 52-58, Jan. 1, 1996.

Mayol et al., Ethynylestradiol-Induced Cell Proliferation in Rat Liver Involvement of Specific Populations of Hepatocytes (Abstract only), *Carcinogenesis*, vol./Iss: 13 (12), pp. 2381-2388, 1992..

Meikrantz et al., Apoptosis and the Cell Cycle, *Journal of Cellular Biochemistry*, vol./Iss: 58 (2), pp. 160-174, Jun. 1995.

Meza et al., Managing the Gastrointestinal Complications of AIDS, *Drug Therapy*, vol./Iss; 23 (11), pp. 74-83, Nov. 1993.

Michel et al., Inhibition of Synaptosomal High-Affinity Uptake of Dopamine and Serotonin by Estrogen Agonists and Antagonists (Abstract only), *Biochem. Pharmacol.*, vol./Iss: 36 (19), pp. 3175-3180, 1987.

Miller et al., Synthesis and Structure-Activity Profiles of A-Homoestranes, the Estratropones, *Journal of Medicinal Chemistry*, vol./Iss: 40, pp. 3836-3841, 1997.

Miller, Thomas, Tubulin as a Therapeutic Target (Abstract only), *Dissertations Abstracts International*, vol./Iss: 5907B, pp. 3454, 1998.

Mollendorff, W. Von, Wachstumsstorungen durch Geschlechtshormone, nach Untersuchungen an Gewebekulturen, English Abstract only, pp. 187-202, Jun. 12, 1941.

Mooberry, Susan, New insights into 2-methoxyestradiol, a promising antiangiogenic and antitumor agent, *Current Opinions in Oncology*, vol./Iss: 15, pp. 425-430, Nov. 1, 2003.

Morgan et al., Calcium and Oestrogen Interactions upon the Rat Thymic Lymphocyte Plasma Membrane (Chemical Abstracts Doc. No. 85:172052, 1976), *Biochemical and Biophysical Research Communications*, vol./Iss: 72 (2), pp. 663-672, Sep. 20, 1976.

Morisaki et al., Steroids. LI. Aromatization reaction of the cross-conjugated dienone system by Zinc 9. (Abstract only), *Chem. Pharm. Bull.*, vol./Iss: 14 (8), pp. 866-872, 1966.

Mueck et al., Angiogenetic and Anti-Angiogenetic Effects of Estradiol and Its Metabolites (Abstract only), *Journal of Clinical and Basic Cardiology*, vol./Iss: 4 (2), pp. 153-155, 2001.

Mueck et al., Estrogen-dependent Neoplasia—What is the Significance of Estradiol Metabolites (English Abstract only)(Abstract only), *Zentralbl Gynakol*, vol./Iss: 125, pp. 458-466, Jan. 2003.

Mueck et al., Estradiol metabolism and malignant disease, *Maturitas*, vol./Iss: 43, pp. 1-10, Jan. 2002.

Mueck et al., Chemotherapy of breast cancer-additive anticancerogenic effects by 2-methoxyestradiol, *Life Sciences*, vol./Iss: 75, pp. 1205-1210, Jan. 1, 2004.

Mukhopadhyay et al., Induction of Apoptosis in Human Lung Cancer Cells after Wild-Type p53 Activation by Methoxyestradiol, *Oncogene*, vol./Iss: 14, pp. 379-384, 1997.

Mukhopadhyay et al., Two-dimensional gel analysis of apoptosis-specific p53 isoforms induced by 2- methoxyestradiol in human lung cancer cells, *Apoptosis*, vol./Iss: 3, pp. 421-430, Jan. 1998.

Mukundan et al., Liver Regeneration in Oral Contraceptive Treated Female Rats—Effects of Moderate Malnutrition (Chemical Abstracts Doc. No. 102:143342, 1984), *Hormone and Metabolic Research*, vol./Iss: 16 (12), pp. 641-645, Dec. 1984.

Naafs et al., Thalidomide Therapy An Open Trial, *International Journal of Dermatology*, vol./Iss: 24 (2), pp. 131-134, Mar. 1985.

Nakagawa-Yagi et al., The Endogenous Estrogen Metabolite 2-Methoxyestradiol Induces Apoptotic Neuronal Cell Death In Vitro, *Life Sciences*, vol./Iss: 58 (17), pp. 1461-1467, 1996.

Nakamura et al., Studies on the Total Synthesis of *dl*-Colchiceine. 1. Synthesis of 3-Hydroxy-9, 10, 11-trimethoxy-1,2,3,4,6,7-hexahydro-5*H*-dibenzo[a,c] cycloheptatrien-5-one, *Chemical and Pharmaceutical Bulletin*, vol./Iss: 10, pp. 281-290, 1962.

Nambara et al., Studies on Steroid Conjugates. III. New Synthesis of 2-Methoxyestrogens, *Chem. Pharm. Bulletin*, vol./Iss: 18 (3), pp. 474-480, Mar. 1970.

Nambara et al., Microbial Transformation Products Derived from Steriods. 1. Synthesis of 1,2- and 3- Dimethoxy-4-Methylestratrienes (Abstract only), *Chem. Pharm. Bull.*, vol./Iss: 20 (2), pp. 336-342, 1972.

Nambara et al., Synthesis of 16β-Oxygenated Catechol Estrogen Methyl Ethers, New and Potential Metabolites, *Chemical & Pharmaceutical Bulletin*, vol./Iss: 23 (7), pp. 1613-1616, Jul. 1975.

Nambara, T., et al., DN 82:43650; Analytical Chemical Studies on Steroids. LXXIII. Synthesis of Epimeric 2-Hydroxy-16-Chlorestrong Monomethyl Ethers (Abstract only), *HCAPLUS—Chemical and Pharmaceutical Bulletin*, vol./Iss: 22 (10), pp. 2455-2457, 1974.

Napolitano et al., 11 Beta-Substituted Estradiol Derivatives. 2. Potential Carbon-11 and Iodine-Labeled Probes for the Estrogen Receptor (Abstract only), *Journal of Medicinal Chemistry*, vol./Iss: 38 (14), pp. 2774-2779, Jul. 7, 1995.

Nelimarkka et al., Decorin is Produced by Capillary Endothelial Cells in Inflammation-Associated Angiogenesis (Abstract only), *American Journal of Pathology*, vol./Iss: 158 (2), pp. 345-353, Feb. 1, 2001.

Nelson, J.D., Superior Limbic Keratoconjunctivitis (SLK) (Abstract only), *Eve*, vol./Iss: 3 (Pt 2), pp. 180-189, Jan. 1, 1989.

Newkome et al., Synthesis of Simple Hydrazones of Carbonyl Compounds by an Exchange Reaction, *Journal of Organic Chemistry*, vol./Iss: 31, pp. 677-681, Mar. 1966.

Newman et al., Inhibition of In Vitro Angiogenesis by 2-Methoxy- and 2-Ethyl-Estrogen Sulfamates, *International Journal of Cancer*, vol./Iss: 109, pp. 533-540, Jan. 1, 2004.

Nguyen, M. et al., Elevated Levels of the Angiogenic Peptide Basic Fibroblast Growth Factor in Urine of Bladder Cancer Patients, *Journal of the National Cancer Institute*, vol./Iss: 85 (3), pp. 241-242, Feb. 3, 1993.

Nishigaki et al., Anti-Proliferative Effect of 2-Methoxyestradiol on Cultured Smooth Muscle Cells from Rabbit Aorta, *Atherosclerosis*, vol./Iss: 113, pp. 167-170, 1995.

Numazawa et al., Efficient Synthesis of 2-Methoxy- and 4-Methoxy-Estrogens, *Journal of the Chemical Society*, pp. 533-534, Jan. 1, 1983.

Numazawa et al., Novel and Regiospecific Synthesis of 2-Amino Estrogens via Zincke Nitration, *Steroids*, vol./Iss: 41 (5), pp. 675-682, 1983.

Numazawa et al., Synthesis of 2-Methoxy- and 4-Methoxy-Estrogens with Halogen-Methoxy Exchange Reactions, *Journal of Chemical Research*, pp. 348-349, Jan. 1, 1985.

Ochs et al., Effect of Tumor Promoting Contraceptive Steroids on Growth and Drug Metabolizing Enzymes in Rat Liver (Abstract only), *Cancer Research*, vol./Iss: 46 (3), pp. 1224-1232, 1986.

Omar et al., Synthesis,Binding Affinities and Uterotrophic Activity of Some 2-Substituted Estradiol and Ring-A-Fused Pyrone Derivatives, *European Journal of Medicinal Chemistry*, vol./Iss: 29, pp. 25-32, 1994.

Oppolzer et al., 177. The Enantioselective Synthesis of (+)-Estradiol from 1,3-Dihydrobenzo[c] thiophene-2,2-dioxide by Successive Thermal $SO_2$-Extrusion and Cycloaddition Reactions, *Helvetica Chimica Acta*, vol./Iss: 63, pp. 1703-1705, 1980.

Pakala et al., Modulation of Endothelial Cell Proliferation by Retinoid x Receptor Agonists, *European Journal of Pharmacology*, vol./Iss: 385 (2/3), pp. 255-261, Sep. 1999.

Paller et al., Responses Anti-Angiogenic Therapies (Abstract only), *Journal of Investigative Dermatology*, vol./Iss: 5 (1), pp. 83-86, Dec. 1, 2000.

Paquette et al., Activation of matrix metalloproteinase-2 and-9 by 2- and 4-hydroxyestradiol, *The Journal of Steroid Biochemistry & Molecular Biology*, vol./Iss: 87, pp. 65-73, Jan. 2003.

Parthasarathy et al., Antioxidant: A New Role for RU-486 and Related Compounds (Abstract only), *Journal of Clinical Investigation*, vol./Iss: 94 (5), pp. 1990-1995, Nov. 1994.

Patz, A., Clinical and Experimental Studies on Retinal Neovascularization. XXXIX Edward Jackson Memorial Lecture. (Abstract only), *American Journal of Ophthalmology*, vol./Iss: 94 (6), pp. 715-743, Dec. 1, 1982.

Paull et al., Identification of Novel Antimitotic Agents Acting at the Tubulin Level by Computer-assisted Evaluation of Differential Cytotoxicity Data, *Cancer Research*, vol./Iss: 52 (14), pp. 3892-3900, Jul. 15, 1992.

Pelicano et al., Inhibition of Mitochondrial Respiration, *The Journal of Biologicy Chemistry*, vol./Iss: 278 (39), pp. 37832-37839, Sep. 26, 2003.

Penfold et al., Age-Related Macular Degeneration: Ultrastructural Studies of the Relationship of Leucocytes to Angiogenesis (Abstract only), *Graefes Archive for Clinical and Experimental Ophthalmology*, vol./Iss: 225 (1), pp. 70-76, Jan. 1, 1987.

Peng et al., Synthesis and Optical Properties of Novel Unsymmetrical Conjugated Dendrimers, *Journal of the American Chemical Society*, vol./Iss: 122, pp. 6619-6623, 2000.

Penn et al., The Effect of Angiostatic Steroid on Neovascularization in a Rat Model of Retinopathy of Prematurity (Abstract only), *Investigative Ophthalmology & Visual Science*, vol./Iss: 42 (1), pp. 283-290, Jan. 1, 2001.

Penn et al., Variable Oxygen Exposure Causes Preretinal Neovascularization in the Newborn Rat, *Investigative Ophthalmology & Visual Science*, vol./Iss: 34 (3), pp. 576-585, Mar. 1, 1993.

Pert et al., Preparations of 2,4-disubstituted estradiols (Abstract only—Applicants do not have complete copy), *Australian Journal of Chemistry*, vol./Iss: 42 (3), pp. 421-432, 1989.

Peters et al., 17-Desoxy Estrogen Analogues, *Journal of Medicinal Chemistry*, vol./Iss: 32 (7), pp. 1642-1652, 1989.

Pfeiffer et al., Are Catechol Estrogens Obligatory Mediators of Estrogen Action in the Central Nervous System? 1. Characterization of Pharmacological Probes with Different Receptor Binding Affinities and Catechol Estrogen Formation Rates (Abstract only), *Journal of Endocrinology*, vol./Iss: 110 (3), pp. 489-497, 1986.

Poli et al., Tumor Necrosis Factor α Functions in an Autocrine Manner in the Induction of Human Immunodeficiency Virus Expression, *Proceedings of the National Academy of Science USA*, vol./Iss: 87 (2), pp. 782-785, Jan. 1990.

Potvin et al., Mechanisms of Action of Antimalarials in Inflammation: Induction of Apoptosis in Human Endothelial Cells (Abstract only), *Journal of Immunobiology*, vol./Iss: 158 (4), pp. 1872-1879, Feb. 15, 1997.

Powell et al., Investigation and Treatment of Orogenital Ulceration; studies on a Possible Mode of Action of Thalidomide, *British Journal of Dermatology*, vol./Iss: 113 Supp. 28, pp. 141-144, Jul. 1985.

Pribluda et al., 2-Methoxyestradiol—A Novel Endogenous Chemotherapeutic and Antiangiogenic Agent—Chapter 21, *The New Angiotherapy*, pp. 1-21, Nov. 2000.

Pribluda et al., 2-Methoxyestradiol: An endogenous antiangiogenic and antiproliferative drug candidate, *Cancer and Metastasis Reviews*, pp. 173-179, Jan. 1, 2000.

Purohit et al., The Effect of 2-Methoxyestrone-3-*O*-Sulphamate on the Growth of Breast Cancer Cells and Induced Mammary Tumours, *International Journal of Cancer*, vol./Iss: 85, pp. 584-589, Jan. 1, 2000.

Qadan et al. 2-Methoxyestradiol Induces G2/M Arrest and Apoptosis in Prostate Cancer, *Biochemical and Biophysical Research Communications*, vol./Iss: 285 (5), pp. 1259-1266, Jan. 2001.

Qanungo et al., 2-Methoxyestradiol induces mitochondria dependent apoptotic signaling in pancreatic cancer cells, *Oncogene*, vol./Iss: 21, pp. 4149-4157, Jan. 2002.

Rajkumar et al., Prevention of mammary carcinogenesis by short-term estrogen and progestin treatments, *Breast Cancer Research*, vol/Iss: 6 (1), pp. R31-R37, Nov. 11, 2003.

Ramirez et al., Estradiol, in the CNS, Targets Several Physiologically Relevant Membrane-Associated Proteins, *Brain Research Reviews*, vol./Iss: 37, pp. 141-152, Jan. 1, 2001.

Rao et al., Structural Specificity of Estrogens in the Induction of Mitotic Chromatid Non-Disjunction in Hela Cells, *Experimental Cell Research*, vol/Iss: 48, pp. 71-81, 1967.

Rao et al., A Novel, Two-Step Synthesis of 2-Methoxyestradiol, *Synthesis*, pp. 168-169, Mar. 1, 1977.

Rao et al., Synthesis and Antimitotic Activity of Novel 2-Methoxyestradiol Analogs, *Steroids*, vol./Iss: 67, pp. 1079-1089, Jan. 2002.

Rao et al., A new, practical synthesis of 2-methoxyestradiols, *Steroids*, vol./Iss: 67, pp. 1065-1070, Jan. 2002.

Raobaikady et al., Inhibition of MCF-7 breast cancer cell proliferation and in vivo steroid sulphatase activity by 2-methoxyestradiol-bis-sulphamate, *The Journal of Steroid Biochemistry & Molecular Biology*, vol./Iss: 84, pp. 351-358, Jan. 2003.

Ravindra, R., Effect of Estradiol on the in vitro Assembly of Rat Brain Tubulin, *Journal of Indian Institute of Science*, vol./Iss: 64 (3), pp. 27-35, Mar. 1983.

Reddy et al., Ocular Complications of Adult Rheumatoid Arthritis (Abstract only), *Rheumatology International*, vol./Iss: 16 (2), pp. 49-52, Jan. 1, 1996.

Reed et al., Aromatase Regulation and Breast Cancer, *Clinical Endocrinology*, vol./Iss: 54, pp. 563-571, Jan. 1, 2001.

Ribatti et al., Anti-Angiogenesis: A Multipurpose Therapeutic Tool? *International Journal of Clinical & Laboratory Research*, vol./Iss: 23 (3), pp.: 117-120, Jan. 1, 1993.

Riono et al., Scleritis: A Clinicopathologic Study of 55 Cases (Abstract only), *Ophthalmology*, vol./Iss: 106 (7), pp. 1328-1333, Jul. 1, 1999.

Robinson et al., Safety and Pharmacokinetics of Intravitreal 2-Methoxyestradiol Implants in Normal Rabbit and Pharmacodynamics in a Rat Model of Choroidal Neovascularization, *Experimental Eye Research*, vol./Iss: 74, pp. 309-317, Jan. 2002.

Robinson et al., Retinal Vein Occlusion (Abstract only), *American Family Physician*, vol./Iss: 45 (6), pp. 2661-2666, Jun. 1, 1992.

Rodi et al., Identification of Small Molecular Binding Sites within Proteins Using Phage Display Technology, *Combinatorial Chemistry & High Throughput*, vol./Iss: 4, pp. 553-572, Jan. 1, 2001.

Romanelli et al., Ethyl-*p*-Dimethylaminophenylacetate, *Organic Synthesis*, vol./Iss: 5, pp. 552-554, Oct. 24, 1973.

Roth et al., Macular Translocation for Subfoveal Choroidal Neovascularization in Angioid Streaks (Abstract only), *American Journal of Ophthalmology*, vol./Iss: 131 (3), pp. 390-392, Mar. 1, 2001.

Rowsey et al., Radial Keratotomy: Preliminary Report of Complications (Abstract only), *Ophthalmic Surgery*, vol./Iss: 13 (1), pp. 27-35, Jan. 1, 1982.

Roy-Chaudhury et al., Venous Neointimal Hyperplasia in Polytetrafluoroethylene Dialysis Grafts (Abstract only), *Kidney International*, vol./Iss: 59 (6), pp. 2325-2334, Jan. 11, 2001.

Sakaguchi et al., Trehalose 6,6'-Dimycolate (Cord Factor) Enhances Neovascularization through Vascular Endothelial Growth Factor Production by Neutrophils and Macrophages, *Infection and Immunity*, vol./Iss: 68 (4), pp. 2043-2052, Apr. 1, 2000.

Sakakibara et al., Effects of Diethylstilbestrol and its Methl Ethers on Aneuploidy Induction and Microtubule Distribution in Chinese Hamster V79 cells, *Mutation Research*, vol./Iss: 263 (4), pp. 269-276, Aug. 1991.

Sakakibara, Kyoichi, 2-Hydroxy-1,3,5(10)-estratriene derivatives (Abstract only) (Identifier: XP-002186126), *Chemical Abstracts*, vol./Iss: 60(1), Jan. 6, 1964.

Sanislo et al., Optic Nerve Head Neovascularization in a Patient with Inactive Cytomegalovirus Retinitis and Immune Recovery (Abstract only), *American Journal of Ophthalmology*, vol./Iss: 126 (2), pp. 318-320, Aug. 1, 1998.

Sato et al., Effect of Estradiol and Ethynylestradiol on Microtubule Distribution in Chinese Hamster V79 Cells, *Chemical and Pharmaceutical Bulletin*, vol./Iss: 40 (1), pp. 182-184, Jan. 1992.

Sato et al., Disruptive Effect of Diethylstilbestrol on Microtubules, *Gann*, vol./Iss: 75 (12), pp. 1046-1048, Dec. 1984.

Sato et al., Natural Estrogens Induce Modulation of Microtubules in Chinese Hamster V79 Cells in Culture (Abstract only), *Horm. Carcinog. II. Proceedings Int. Symp., 2nd (1996), Meeting Date 1994*, pp. 454-457, 1996.

Sawada et al., Colchicine-Like Effect of Diethylstilbestrol (DES) on Mammalian Cells in Vitro, *Mutation Research*, vol./Iss: 57, pp. 175-182, May 1978.

Schaub et al., Novel Agents that Promote Bone Regeneration (Abstract only), *Current Opinion in Biotechnology*, vol./Iss: 2 (6), pp. 868-871, Dec. 1, 1991

Scherr et al., The Nonsteroidal Effects of Diethylstilbestrol: The Rationale for Androgen Deprivation Therapy without Estrogen Deprivation in the Treatment of Prostate Cancer, *The Journal of Urology*, vol./Iss: 170, pp. 1703-1708, Nov. 1, 2003

Schiff et al., Tubulin: A Target for Chemotherpeutic Agents, *Molecular Actions and Targets for Cancer Chemotheraneutic Agents*, pp. 483-507, Jan. 1, 1981.

Schumacher et al., The Physiological Estrogen Metabolite 2-Methoxyestradiol Reduces Tumor Growth and Induces Apoptosis in Human Solid Tumors, *Cancer Research Clinical Oncology*, vol./Iss: 127, pp. 405-410, 2001.

Schumacher et al., 2-Methoxyestradiol Induces p53 Independent Apoptosis and Inhibits Growth of Lung Metastases of Pancreatic Cancer (English summary p. 52), *Langenbecks Arch Chir 1*, vol./Iss: 1, pp. 49-52, Jan. 1998.

Seegers et al., Cyclic-AMP and Cyclic-GMP Production in MCF-7 Cells Exposed to Estradiol-17 Beta, Catecholstrogens and Methoxy-Estrogens in MCF-7Cells (Meeting Abstract only), *Joint MCI-1st Symposium. Third 1st International Symposium. Biology and Therapy of Breast Cancer*, Sep. 25, 1989.

Seegers et al., The Mammalian Metabolite, 2-methoxyestradiol, Affects P53 Levels and Apoptosis Induction in Transformed Cells but Not in Normal Cells, *Journal of Steroid Biochemistry and Molecular Biology*, vol./Iss: 62 (4), pp. 253-267, Jul. 1997.

Seegers, J.C. et al., The Cytotoxic Effects of Estradiol-17β, Catecholestradiols and Methoxyestradiols on Dividing MCF-7 and HeLa Cells, *Journal of Steroid Biochemistry*, vol/Iss:32 (6), pp. 797-809, Jun. 1989.

Seng et al., Use of a monoclonal antibody specific for activated endothelial cells to quantitate angiogenesis in vivo in zebrafish after drug treatment, *Angiogenesis*, vol./Iss: 7, pp. 243-253, Jan. 1, 2004.

Servold, S.A., Growth Factor Impact on Wound Healing, *Clinics in Podiatric Medicine and Surgery*, vol./Iss: 8 (4), pp. 937-953, Oct. 1, 1991.

Shah et al., (+/−)-(N-alkylamino)benzazepine Analogs: Novel Dopamine D1 Receptor Antagonists (Abstract only), *Journal of Medicinal Chemistry*, vol./Iss: 38 (21), pp. 4284-4293, Oct. 13, 1995.

Shang et al., 2-Methoxyestradiol, an Endogenous Estradiol Metabolite, Differentially Inhibits Granulosa and Endothelial Cell Mitosis: A Potential Follicular Antiangiogenic Regulator, *Biology of Reproduction*, vol/Iss: 65, pp. 622-627, Jan. 1, 2001.

Sharp et al., Diethylstilboestrol: the Binding and Effects of Diethylstilboestrol upon the Polymerisation and Depolymerisation of Purified Microtubule Protein in vitro, *Carcinogenesis*, vol./Iss: 6 (6), pp. 865-871, Jun. 1985.

Sheela et al., Angiogenic and Invasive Properties of Neurofibroma Schwann Cells, *Journal of Cell Biology*, vol./Iss: 111 (2), pp. 645-653, Aug. 1, 1990.

Shim et al., Hydrazinocurcumin, A Novel Synthetic Curcumin Derivative, Is a Potent Inhibitor of Endothelial Cell Proliferation (Abstract only), *Caplus: Bioorganic & Medicinal Chemistry*, vol./Iss: 10 (8), pp. 2439-2444, 2002.

Shimada et al., The Molecular Mechanism of Sensitization to Fas-Mediated Apoptosis by 2-Methoxyestradiol in PC3 Prostate Cancer Cells, *Molecular Carcinogenesis*, vol./Iss: 39, pp. 1-9, Jan. 1, 2004.

Shimada et al., Roles of p38- and c-jun NH2-terminal kinase-mediated pathways in 2-methoxyestradiol-induced p53 induction and apoptosis, *Carcinogenesis*, vol./Iss: 24 (6), pp. 1067-1075, Jan. 2003.

Shishkina et al., Synthesis and Properties of Condensed Heterocyclic Derivatives of Estra-4, 9-dien-17.beta.-ol-3-one (Abstract only), *Khim.-Farm. Zh.*, vol./Iss: 8 (1), pp. 7-11, 1974.

Shweiki et al., Patterns of Expression of Vascular Endothelial Growth Factor (VEGF) and VEGF Receptors in Mice Suggest a Role in Hormonally Regulated Angiogenesis, *Journal of Clinical Investigation*, Abstract only vol./Iss: 91 (5), pp. 2235-2243, May 1, 1993.

Sibonga et al., Evidence that 2-methoxyestradiol suppresses proliferation and accelerates apoptosis in normal rat growth plate chondrocytes, *Journal of Cancer Research and Clinical Oncology*, vol./Iss: 128, pp. 477-483, Jan. 2002.

Sidky et al., Inhibition of Angiogenesis by Interferons: Effects on Tumor- and Lymphocyte-induced Vascular Responses, *Cancer Research*, vol./Iss: 47, pp. 5155-5161, Oct. 1, 1987.

Simons, M., General Concepts of Angiogenesis, pp. 1-6, Apr. 17, 2000.

Singh et al., Inhibition of Deoxyglucose Uptake in MCF-7 Breast Cancer Cells by 2-Methoxyestrone and 2-Methoxyestrone-3-O-sulfamate (Abstract only), *Molecular and Cellular Endocrinology*, vol./Iss: 160 (I-2), pp. 61-66, 2000.

Singhal et al., Novel Therapies in Multiple Myeloma, *International Journal of Hematology*, vol./Iss: 77, pp. 226-231, Jan. 9, 2003.

Siracusa et al., The Effect of Microtubule- and Microfilament-disrupting Drugs on Preimplantation Mouse Embryos (Abstract only, *Jouranl of Embryology and Experimental Morphology*, vol./Iss: 60, pp. 71-82, Dec. 1980.

Sowka et al., Phlyctenulosis, *Handbook of Ocular Disease Management*, Jan. 1, 2000.

Spicer et al., Catecholestrogens Inhibit Proliferation and DNA Synthesis of Porcine Granulosa Cells in Vitro: Comparison with Estradiol, 5α-dihydrotestosterone, Gonadotropins and Catecholamines (Chemical Abstracts Doc. No. 111:50609. 1989), *Molecular and Cellular Endocrinology*, vol./Iss: 64, pp. 119-126, 1989.

Spink et al., SULT1A1 Catalyzes 2-Methoxyestradiol Sulfonation in MCF-7 Breast Cancer Cells, *Carcinogenesis*, vol./Iss: 21 (11), pp. 1947-1957, Jan. 1, 2000.

Spyriounis et al., Copper (II) complex of an estradiol derivative with potent antiinflammatory properties (Abstract only), *Arch. Pharm.*, vol./Iss: 324 (9), pp. 533-536, 1991.

Srivastava, A. et al., The Prognostic Significance of Tumor Vascularity in Intermediate-Thickness (0.76-4.0 mm Thick) Skin Melanoma, *American Journal of Pathology*, vol./Iss: 133 (2), pp. 419-424, Nov. 1, 1988.

Staples et al., Structural Requirements for Steroid Inhibition of Sheep Lymphocyte Mitogenesis in vitro, *Steroids*, vol./Iss: 44 (5), pp. 419-433, Nov. 1984.

Starkov et al., Mono- and Dialkylation of Guaiacol by Olefins on KU-2 Cation Exchanger (Abstract only), *Zhurnal Prikladnoi Khimii*, vol./Iss: 41 (3), pp. 688-690, 1968.

Sternlicht et al., Colchicine Inhibition of Microtubule Assembly via Copolymer Formation, *The Journal of Biological Chemistry*, vol./Iss: 254 (20), pp. 10540-10550, Oct. 25, 1979.

Stiffey-Wilusz et al., An ex vivo Angiogenesis Assay Utilizing Commercial Porcine Carotid Artery: Modification of the Rat Aortic Ring Assay, *Angiogenesis*, vol./Iss: 4, pp. 3-9, Jan. 1, 2001.

Strizzi et al., Vascular Endothelial Growth Factor is an Autocrine Growth Factor in Human Malignant Mesothelioma, *Journal of Pathology*, vol./Iss: 193 (4), pp. 468-475, Apr. 1, 2001.

Subbaramaiah et al., Microtubule-Interfering Agents Stimulate the Transcription or Cyclooxygenase-2, *The Journal of Biological Chemistry*, vol./Iss: 275 (20), pp. 14838-14845. May 19, 2000.

Sudhoff et al., Angiogenesis and Angiogenic Growth Factors in Middle Ear Cholesteatoma, *American Journal of Otology*, Abstract only, vol./Iss: 21 (6), pp. 793-798, Nov. 1, 2000.

Sun et al., Antitumor Agents. 139. Synthesis and Biological Evaluation of Thiocolchicine Analogs 5,6-Dihydro-6($S$)-(acyloxy)-and 5,6-Dihydro-6($S$)-[(aroyloxy) methyl}-1,2,3-trimethoxy-9-(methylthio)-8 $H$-cyclohepta[α]naphthalen-8-ones as Novel Cytotoxic and Antimitotic Agents, *Journal of Medicinal Chemistry*, vol./Iss: 36 (5), pp. 544-551, Mar. 5, 1993.

Sun et al., In Vivo and in Vitro Characteristics of Interleukin 6-Transfeected B16 Melanoma Cells, *Cancer Research*, vol./Iss: 52, pp. 5412-5415, Oct. 1, 1992.

Sunagawa et al., Synthesis of Colchicine Synthesis of *dl*-Demethyoxydeoxy-hexahydrocolchicine, *Chemical & Pharmaceutical Bulletin*, vol./Iss: 9, pp. 81-83, 1961.

Suzuki et al., Growth inhibition of multi-drug-resistant breast cancer cells by 2-methoxyesradiol—bis-sulphamate and 2-ethyloestradiol-bis-sulphamate, *The Journal of Steroid Biochemistry & Molecular Biology*, vol./Iss: 84, pp. 269-278, Jan. 2003.

Sweeney et al., The Antiangiogenic Property of Ooectaxel Is Synergistic with a Recombinant Humanized Monoclonal Antibody Against Vascular Endothelial Growth Factor or 2-Methoxyestradiol but Antagonized by Endothelial Growth Factors, *Cancer Research*, vol./Iss: 61, pp. 3369-3372, Apr. 15, 2001.

Tabbara, K.F., Disruption of the Choroidoretinal Interface by Toxoplasma (Abstract only), *Eve*, vol/Iss: 4 (Part 2), pp. 366-373, Jan. 1, 1990.

Takahashi et al., Effects of estrogens and metabolites on endometrial carcinogenesis in young adult mice initiated with $N$-ethyl-$N'$-nitro-$N$-nitrosoguanidine, *Cancer Letters*, vol./Iss: 211, pp. 1-9, Jan. 1, 2004.

Takanashi et al., Metabolism of [6,7-$^3$H, $^{35}$S] estradiol 17 sulfate in rats, *Steroids*, vol./Iss: 68, pp. 383-392, Jan. 2003.

Takanashi et al., Comparison ex vivo Inhibitory Effect Between 2-Hydroxyestradiol and Its 17-Sulfate on Rat Hepatic Microsomal Lipid Peroxidation, *Lipids*, vol./Iss: 38 (8), pp. 847-854, Jan. 2003.

Takata et al., 2-Methoxyestradiol Enhances p53 Protein Transduction Therapy-Associated Inhibition of the Proliferation of Oral Cancer Cells through the Suppression of NF-B Activity, *Acta Medica Okayama*, vol./Iss: 58 (4), pp. 181-187, Jan. 1, 2004.

Taylor, S. et al., Protamine is an Inhibitor of Angiogenesis, *Nature*, vol./Iss: 297, pp. 307-312, May 27, 1982.

Teranishi, M. et al., Methylation of Catechol Estrogen with Diazomethane, *Chemical and Pharmaceutical Bulletin*, vol./Iss: 31 (9), pp. 3309-3314, Sep. 1983.

Timar et al., Angiogenesis-Dependent Diseases and Angiogenesis Therapy (Abstract only), *Pathology and Oncology Research*, vol./Iss: 7 (2), pp. 85-94, Jan. 1, 2001.

Tishler et al., Microtubule-Active Drugs Taxol, Vinblastine, and Nocodazole Increase the Levels of Transcriptionally Active p53, *Cancer Research*, vol./Iss: 55, pp. 6021-6025, Dec. 15, 1995.

Tremblay et al., A Convenient Synthetic Method for Alpha-Alkylation of Steroidal 17-Ketone: Preparation of 16β-(THPO-Heptyl)-Estradiol, *Synthetic Communications*, vol./Iss: 25 (16), pp. 2483-2495, 1995.

Tremblay et al., Synthesis of 16-(Bromoalkyl)-Estradiols Having Inhibitory Effect on Human Placental Estradiol 17β-Hydroxysteroid Dehydrogenase (17β-HSD Type 1), *Bioorganic & Medicinal Chemistry*, vol./Iss: 3 (5), pp. 505-523, 1995.

Tsutsui et al., Comparison of Human Versus Syrian Hamster Cells in Culture for Induction of Mitotic Inhibition, Binucleation and Multinucleation, Following Treatment with Four Aneuploidogens, *Toxicology in Vitro*, vol./Iss: 4 (1), pp. 75-84, 1990.

Tsutsui et al., et al., Induction of Mammalian Cell Transformation and Genotoxicity by 2-Methoxyestradiol, an Endogenous Metabolite of Estrogen, *Carcinogenesis*, vol./Iss: 21 (4), pp. 735-740, Jan. 1, 2000.

Tuder et al., The Pathobiology of Pulmonary Hypertension Endothelium, *Clinicals in Chest Medicine*, vol./Iss: 22 (3), pp. 405-418, Sep. 1, 2001.

Turner et al., 2-Methoxyestradiol Inhibits Longitudinal Bone Growth in Normal Female Rats, *Calcified Tissue International*, pp. 465-469, Jan. 1, 2000.

Urakawa et al., Examination of a modified cell cycle synchronization method and bovine nuclear transfer using synchronized early G1 phase fibroblast cells, *Theriogenology*, vol./Iss: 62, pp. 714-728, Jan. 1, 2004.

Utne et al., The Synthesis 2- and 4-Fluoroestradiol, *Journal of Organic Chemistry*, vol./Iss: 33 (6), pp. 2469-2473, Jun. 1968.

Van Der Eerden et al., Evidence for genomic and nongenomic actions of estrogen in growth plate regulation in female and male rats at the onset of sexual maturation, *Journal of Endocrinology*, vol./Iss: 175, pp. 277-288, Jan. 2002.

Van Duursen et al., Effects of several dioxin-like compounds on estrogen metabolism in the malignant MCF-7 and nontumorigenic MCF-10A human mammary epithelial cell lines, *Toxicology and Applied Pharmacology*, vol./Iss: 190, pp. 241-250, Jan. 2003.

Van Geerestein et al., Structure of 11.beta-(4-dimethylamino)phenyl)-17.beta.-hydroxy-17.alpha.-(2-propenyl) estra-4,9-dien-3-one (Identifier only), *Acta Crystallogr., Sect. C: Cryst. Struct. Commun.*, vol./Iss: C43 (2), pp. 319-322, 1987.

Van Tamelen et al., The Synthesis of Colchicine, *Tetrahedron*, vol./Iss: 14 (½), pp. 8-34, Sep. 1961.

Verdier-Pinard et al., A Steroid Derivative with Paclitaxel-Like Effects on Tubulin Polymerization, *Molecular Pharmacology*, vol./Iss: 57, pp. 568-575, Jan. 1, 2000.

Vicente et al., In Vitro Activity of Thalidomide Against Mycohacterium avium Complex, *Archives of Internal Medicine*, vol./Iss: 153 (4), pp. 534, Feb. 22, 1993.

Walsh et al., Angiogenesis in the Pathogenesis of Inflammatory Joint and Lung Diseases, *Arthritis Research*, vol./Iss: 3 (3), pp. 147-153, Jan. 1, 2001.

Wang et al., Photoaffinity Labeling oF Human Placental Estradiol 17.beta.-dehydrogenase with 2-and 4-azidoestrone, 2- and 4-azidoestradiol (Abstact only), *Shengwu Huaxue Zazhi*, vol./Iss: 8 (6), pp. 715-718, 1992.

Wang et al., Synthesis of B-Ring Homologated Estradiol Analogues that Modulate Tubulin Polymerization and Microtubule Stability, *Journal of Medicinal Chemistry*, vol./Iss: 43, pp. 2419-2429, 2000.

Wang et al., A Simple Quantitative Method for Evaluation of Angiogenesis Activity, *Assay and Drug Development Technologies*, vol./Iss: 2 (1), pp. 31-38, Jan. 1, 2004.

Wang et al., 2-Methoxyestradiol, an Endogenous Estrogen Metabolite, Induces Thyroid Cell Apoptosis, *Molecular and Cellular Endocrinology*, vol./Iss; 165, pp. 163-172, Jan. 1, 2000.

Wang, Z. et al., An Optimized Synthesis of 2-Methoxyestradiol, a Naturally Occurring Human Metabolite with Anticancer Activity, *Synth.Commun.*, vol./Iss: 28 (23), pp. 4431-4437, 1998.

Watson, P.G., Management of Mooren's Ulceration (Abstract only), *Eve*, vol./Iss: 11 (Pt 3), pp. 349-356, Jan. 1, 1997.

Weidner, N. et al., Tumor angiogenesis: A New Significant and Independent Prognostic Indicator in Early-Stage Breast Carcinoma, *Journal of the National Cancer Institute*, vol./Iss: 84, pp. 1875-1887, Dec. 16, 1992.

Weidner, N. et al., Tumor Angiogenesis Correlates with Metastasis in Invasive Prostate Carcinoma, *American Journal of Pathology*, vol./Iss: 143 (2), pp. 401-409, Aug. 1, 1993.

Weidner, N. et al., Tumor Angiogenesis and Metastasis-Correlation in Invasive Breast Carcinoma, *New England Journal of Medicine*, vol./Iss: 324 (1), pp. 1-8, Jan. 3, 1991.

Welsch et al., Staphylostatic Activity of Some New Diphenols, Napthols, and Chalcones (Abstract only), *Experientia*, vol./Iss: 11, pp. 350-351, 1955.

Wheeler et al., Mitotic Inhibition and Aneuploidy Induction by Naturally Occurring and Synthetic Estrogens in Chinese Hamster Cells in Vitro, *Mutation Research*, vol./Iss: 171, pp. 31-41, Jul. 1986.

Wheeler et al., Mitotic Inhibition and Chromosome Displacement Induced by Estradiol in Chinese Hamster Cells (Chemical Abstracts Doc. No. 105:54822, 1986), *Cell Motility and the Cytoskeleton*, vol./Iss: 7 (3), pp. 235-247, 1987.

White et al., Treatment of Pulmonary Hemangiomatosis with Recombinant Interferon Alfa-2a, *The New England Journal of Medicine*, vol./Iss: 32 (18), pp. 1197-1200, May 4, 1989.

Wiedemann, P., Growth Factors in Retinal Disease: Proliferative Vitreoretinopathy, Proliferative Diabetic Retinopathy, and Retinal Degeneration, *Survey of Ophthalmology*, vol./Iss: 36 (5), pp. 373-384, Mar. 1, 1992, Abstract only.

Wiese et al., Induction of the Estrogen Specific Mitogenic Response of MCF-7 Cells by Selected Analogues of Estradiol-17 β: A 3D QSAR Study, *Journal of Medicinal Chemistry*, vol./Iss: 40, pp. 3659-3669, 1997.

Wood et al., 2-MeOE2bisMATE induces caspase-despendent apoptosis in CAL51 breast cancer cells and overcomes resistance to TRAIL via cooperative activation of caspases, *Apoptosis*, vol./Iss: 9, pp. 323-332, Jan. 1, 2004.

Wurtz et al., Three-Dimensional Models of Estrogen Receptor Ligand Binding Domain Complexes, Based on Related Crystal Structures and Mutational and Structure-Activity Relationship Data, *Journal of Medicinal Chemistry*, vol./Iss: 41, pp. 1803-1814, 1998.

Xiao et al., Effects of Estradiol and Its Metabolites on Glomerular Endothelial Nitric Oxide Synthesis and Mesangial Cell Growth, *Hypertension*, vol./Iss: 37 (part 2), pp. 645-650, Feb. 1, 2001.

Yang, Ning-Sun, Gene Transfer into Mammalian Somatic Cells In Vivo, *Critical Reviews in Biotechnology*, vol./Iss: 12 (4), pp. 335-356, 1992.

Yasuda et al., Accelerated differentiation in seminiferous tubules of fetal mice prenatally exposed to ethinyl estradiol (Abstract only), *Anat. Embryol., (Berl.)*, vol/Iss: 174 (3), pp. 289-299, 1986.

Yazaki et al., Inhibition of Angiogenesis and Growth of Human Non-Malignant and Malignant Meningiomas by TNP-470 (Abstract only), *Journal of Neurooncology*, vol./Iss: 23 (1), pp. 23-29, Jan. 1, 1995.

Yue et al., 2-Methoxyestradiol, an Endogenous Estrogen Metabolite, Induces Apoptosis in Endothelial Cells and Inhibits Angiogenesis: Possible Role for Stress-Activated Protein Kinase Signaling Pathway and Fas Expression, *Molecular Pharmacology*, vol./Iss: 51, pp. 951-962, 1997.

Zacharia et al., 2-Hydroxyestradiol Is a Prodrug of 2-Methoxyestradiol, *Journal for Pharmacology and Experimental Therapeutics*, vol./Iss: 62505, pp. 1-25, Feb. 10, 2004.

Zacharia et al., Methylation of 2-Hydroxyestradiol in Isolated Organs, *Hypertension*, vol./Iss: 42, pp. 82-87, Jan. 2003.

Zacharia et al., Methoxyestradiols Mediate the Antimitogenic Effects of 17β-Estradiol, *Circulation*, vol./Iss: 108, pp. 2974-2978, Dec. 16, 2003.

Zacharia et al., Catecholamines Abrogate Antimitogenic Effects of 2-Hydroxyestradiol on Human Aortic Vascular Smooth Muscle Cells, *Anteriosclerosis, Thrombosis and Vascular Biology*, vol./Iss: 21, pp. 1745-1750, Nov. 1, 2001.

Zacharia et al., Increased 2-Methoxyestradiol Production in Human Coronary Versus Aortic Vascular Cells, *Hypertension*, vol./Iss: 37 (part 2), pp. 658-662, Feb. 1, 2001.

Zhang et al., Detection of 1,2,4-benzenetriol induced aneuploidy and microtubule disruption by flourescence in situ hybridization and immunocytochemistry, *Mutation Research*, vol./Iss: 320, pp. 315-327, 1994.

Zhang et al., Tumor suppressor ARF inhibits HER-2/neu-mediated oncogenic growth, *Oncogene*, vol./Iss: 23, pp. 7132-7143, Jan. 1, 2004.

Zheng et al., Control of Stromal Keratitis by Inhibition of Neovascularization (Abstract only), *American Journal of Pathology*, vol./Iss: 159 (3), pp. 1021-1029, Sep. 1, 2001.

Zoubine et al., 2-Methoxyestradiol-Induced Growth Suppression and Lethality in Estrogen-Responsive MCF-7 Cells May Be Mediated by Down Regulation of p34cdc2 and Cyclin B1 Expression (Abstract only), *International Journal of Oncology*, vol./Iss: 15 (4), pp. 639-646, Oct. 1999.

METHODS OF TREATING DISEASE STATES USING ANTIANGIOGENIC AGENTS

CROSS-REFERENCE TO RELATED APPLICATIONS

This application is a division of application Ser. No. 11/077,977, filed Mar. 11, 2005, now U.S. Pat. No. 7,498,322, which claims the benefit of provisional application Ser. No. 60/562,793, filed Apr. 16, 2004, and provisional application Ser. No. 60/552,692, filed Mar. 12, 2004.

FIELD OF THE INVENTION

The present invention relates to treating disease states characterized by abnormal cell mitosis, to treating disease states characterized by abnormal angiogenesis or to treating disease states characterized by a combination of these events. More particularly, the present invention relates to analogs of 2-methoxyestradiol ($2ME_2$) and their effect on diseases characterized by abnormal cell mitosis and/or abnormal or undesirable angiogenesis.

BACKGROUND OF THE INVENTION

Angiogenesis is the generation of new blood vessels into a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic-associated diseases.

One example of a disease dependent on angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, and pterygium keratitis sicca. Other diseases associated with undesirable angiogenesis include Sjögren's syndrome, acne rosacea, phylectenulosis, syphilis, Mycobacteria infections, lipid degeneration, chemical burns, bacterial ulcers, fungal ulcers, Herpes simplex infection, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Diseases associated with neovascularization include, but are not limited to, retinal/choroidal neovascularization, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, Lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other eye-related diseases include, but are not limited to, diseases associated with rubeosis (neovascularization of the iris and of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the cartilage destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels into inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J. Med.*, 285:1182-86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire, et al., *J. Nat. Cancer Inst.*, 6:73-85 (1945)).

(2) Tumors grown in isolated perfused organs where blood vessels do not proliferate are limited to 1-2 mm$^3$ but expand rapidly to >1000 times this volume when they are transplanted to mice and become neovascularized. (Folkman, et al., *Annals of Surgery*, 164:491-502 (1966)).

(3) Tumor growth in the avascular cornea proceeds slowly and at a linear rate, but switches to exponential growth after neovascularization. (Gimbrone, Jr., et al., *J. Nat. Cancer Inst.*, 52:421-27 (1974)).

(4) Tumors suspended in the aqueous fluid of the anterior chamber of a rabbit eye remain viable, avascular, and limited in size to <1 mm$^3$. Once they are implanted on the iris vascular bed, they become neovascularized and grow rapidly, reaching 16,000 times their original volume within 2 weeks. (Gimbrone, Jr., et. al., *J. Exp. Med.*, 136:261-76).

(5) When tumors are implanted on a chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer*, 35:347-56 (1977)).

(6) Vascular casts of metastases in a rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery*, 68:334-40 (1970)).

(7) In transgenic mice that develop carcinomas in the beta cells of the pancreatic islets, pre-vascular hyperplastic islets are limited in size to <1 mm. At 6-7 weeks of age, 4-10% of the islets become neovascularized, and from these islets arise large vascularized tumors of more than 1000 times the volume of the pre-vascular islets. (Folkman, et al., *Nature*, 339: 58-61 (1989)).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim et al., *Nature*, 362:841-44 (1993)).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.*, 51:6180-84 (1991)).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumor cells in vitro. (Gross, et (al., *Proc. Am. Assoc. Cancer Res.*, 31:79 (1990)).

(11) A specific angiogenesis inhibitor (ACM-1470) inhibits tumor (growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature*, 48:555-57 (1990)). There is also indirect clinical evidence that tumor growth is angiogenesis dependent.

(12) Human retinoblastomas that are metastatic to the vitreous develop into avascular spheroids that are restricted to less than 1 mm$^3$ despite the fact that they are viable and incorporate 3H-thymidine (when removed from an enucleated eye and analyzed in vitro).

(13) Carcinoma of the ovary metastasizes to the peritoneal membrane as tiny avascular white seeds (1-3 mm$^3$). These implants rarely grow larger until one or more of them becomes neovascularized.

(14) Intensity of neovascularization in breast cancer (Weidner, et al., *Nest Eng. J. Med.*, 324:1-8 (1991); Weidner, et al., *J Nat. Cancer Inst.*, 84:1875-87 (1992)) and in prostate cancer (Weidner, et al., *Am. J. Pathol.*, 143(2):401-09 (1993)) correlates highly with risk of future metastasis.

(15) Metastasis from human cutaneous melanoma is rare prior to neovascularization. The onset of neovascularization leads to to increased thickness of the lesion and an increased risk of metastasis. (Srivastava, et al., *Am. J. Pathol.*, 133:419-23 (1988)).

(16) In bladder cancer, the urinary level of an angiogenic protein, bFGF, is a more sensitive indicator of status and extent of disease than is cytology. (Nguyen, et al., *J. Nat. Cancer Inst.*, 85:241-42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with bloodborne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed that angiogenesis plays a role in the abnormalities in the bone marrow that give rise to leukemia tumors and multiple myeloma diseases.

One of the most frequent angiogenic diseases of childhood is the hemangioma. A hemangioma is a tumor composed of newly formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatitic arteriovenous fistula.

What is needed, therefore, is a composition and method that can inhibit angiogenesis. What is also needed is a composition and method that can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogeniesis. Taylor, et al. (*Nature,* 297:307 (1982)) have used protamine to inhibit angiogenesis. The toxicity of protamine limits its practical use as a therapeutic. Folkman, et al. (*Science,* 221:719 (1983), and U.S. Pat. Nos. 5,001,116 and 4,994,443) have disclosed the use of heparin and steroids to control angiogenesis. Steroids, such as tetrahydrocortisol, which lack glucocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogeniesis in mouse dermis stimulated by human neoplastic cells. Interferon beta is also a potent inhibitor of angiogenesis induced by allogeneic spleen cells. (Sidky, et al., *Cancer Res.,* 47:5155-61 (1987)). Human recombinant interferon (alpha/A) was reported to be successfully used in the treatment of pulmonary hemangiomatosis, an angiogenesis-induced disease. (White, et al., *New Eng. J. Med.,* 320:1197-1200 (1989)).

Other agents that have been used to inhibit angiogenesis include ascorbic acid ethers and related compounds. (Japanese Kokai Tokkyo Koho No. 58-13 (1978)). Sulfated polysaccharide DS 4152 also inhibits angiogenesis. (Japanese Kokai Tokkyo Koho No. 63-119500). Additional anti-angiogenic compounds include Angiostatin® (U.S. Pat. Nos. 5,639,725; 5,792,845; 5,885,795; 5,733,876; 5,776,704; 5,837,682; 5,861,372, and 5,854,221) and Endostatin (U.S. Pat. No. 5,854,205).

Another compound which has been shown to inhibit angiogenesis is thalidomide. (D'Amato, et al., *Proc. Natl. Acad. Sci.,* 90:4082-85 (1994)). Thalidomide is a hypnosedative that has been successfully used to treat a number of diseases, such as rheumatoid arthritis (Gutierrez-Rodriguez, *Arthritis Rheum.,* 27 (10):1118-21 (1984); Gutierrez-Rodriguez, et al., *J. Rheumatol.,* 16(2):158-63 (1989)), and Behcet's disease (Handley, et al. *Br. J. Dermatol.,* 127 Suppl, 40:67-8 (1992); Gunzler, *Med. Hypotheses,* 30(2):105-9 (1989)).

Although thalidomide has minimal side effects in adults, it is a potent teratogen. Thus, there are concerns regarding its use in women of child-bearing age. Although minimal, there are a number of side effects that limit the desirability of thalidomide as a treatment. One such side effect is drowsiness. In a number of therapeutic studies, the initial dosage of thalidomide had to be reduced because patients became lethargic and had difficulty functioning normally. Another side effect limiting the use of thalidomide is peripheral neuropathy, in which individuals suffer from numbness and dysfunction in their extremities.

Thus, improved methods and compositions are needed that are easily administered and capable of inhibiting angiogenesis. Additionally, what is needed are safe and effective treatments that cause minimal unwanted side effects.

2-Methoxyestradiol is an endogenous metabolite of estradiol (E2). When administered orally, it exhibits anti-tumor and anti-proliferative activity with little toxicity. In vitro data suggests that 2-dimethoxyestradiol does not engage the estrogen receptor for its anti-proliferative activity and is not estrogenic over a wide range of concentrations, as assayed by estrogen dependent MCF-7 cell proliferation. However, the presence of metabolizing enzymes, such as demethylases, in vivo and in vitro, may metabolize this compound to products, such as 2-hydroxyestradiol, which has been shown to be estrogenic by several approaches. What is needed is a means to improve the bioavailability of estradiol derivatives or 2-methoxyestradiol and to reduce the formation of estrogenic 2-methoxyestradiol metabolites. Other forms of metabolism include conversion of the 17-hydroxy function to the corresponding ketone. Conjugation (either glucuronidation or sulfation) is another major form of metabolism of steroids. What is also needed is a means to modify estradiol derivatives or 2-methoxyestradiol in such a way as to prevent conversion into an estrogenic derivative, metabolic conjugation and/or conversion to estrones.

SUMMARY OF THE INVENTION

The present invention provides certain analogs of 2-methoxyestradiol that are effective in treating diseases characterized by abnormal mitosis and/or abnormal angiogenesis. Specifically the present invention relates to analogs of 2-methoxyestradiol that have been modified at the 2, 3 and 17 positions thereof. Compounds within the general Formulae I and II (shown below) that inhibit cell proliferation are preferred. Compounds within Formulae I and II that inhibit angiogenesis are also preferred. Preferred compositions may also exhibit a change (increase or decrease) in estrogen receptor binding, or improved absorption, transport (e.g., through blood-brain barrier and cellular membranes), biological stability, or decreased toxicity. The invention also provides compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula. Accordingly, the compositions described above can be used to block ovulation and implantation of a blastula or to block menstruation (induce amenorrhea).

It is known that 2-methoxyestradiol (2ME$_2$), an endogenous metabolite of estradiol with no intrinsic estrogenic activity, is a potent antiproliferative agent that induces apoptosis in a wide variety of tumor and non-tumor cell lines. When administered orally, it exhibits antitumor and antiangiogenic activity with little or no toxicity. Currently, 2ME$_2$ is in several clinical trials under the name PANZEM®.

A novel series of compounds has been prepared that retains the biological activities of 2ME$_2$ but is believed to have reduced metabolism. Most of these analogs lack the hydroxyl moiety at position 17 and cannot be metabolized to 2-methoxyestrone or conjugated at that position. These 17-position analogs retain antiproliferative activity in HUVEC and tumor cells. Replacement of the 2-methoxy group by other moieties, such as (n ethoxy or a propynyl group, retain antiproliferative activity, but these functionalities cannot be de-methylated to yield the estrogenic 2-hydroxyl derivatives. Also disclosed are compounds and methods for altering the chemical nature of positions 3 and 17 of 2-methoxyestradiol for preventing conversion to 2-methoxyestrone and/or the conjugation of 2-methoxyestradiol (or metabolites) with other molecules and subsequent loss during excretion of the resulting compounds.

Other features and advantages of the invention will be apparent from the following detailed description of preferred embodiments thereof.

DETAILED DESCRIPTION OF THE INVENTION

As described below, compounds that are useful in accordance with the invention include novel 2-methoxyestradiol derivatives that exhibit anti-mitotic, anti-angiogenic and/or anti-tumor properties. Preferred compounds of the invention are 2-methoxyestradiol derivatives modified at the 2-, 3- or 17-positions or at combinations of the 2-, 3-, and 17-positions. Preferred compounds are those of the general Formulae I or II:

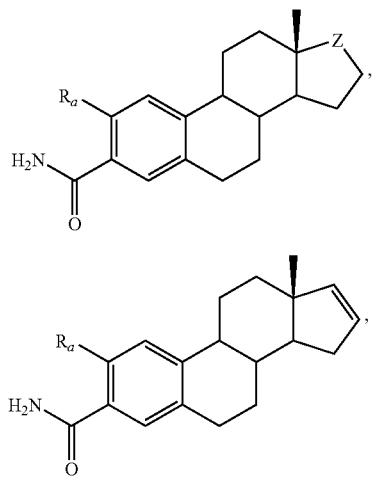

wherein R$_a$ is selected from OCH$_3$, —OCH$_2$CH$_3$ or —CCCH$_3$; and Z is selected from >C(H$_2$), >C(H)—CH$_3$, >C=CH$_2$, >C=CHCH$_3$ (cis or trans), >C=O, >C(H)—OH, >C(H)—O-alkyl or >C(H)—O-sulfamate. Alkyl is defined herein as a linear, branched and/or cyclic hydrocarbon chain containing 1-10 carbons. Preferred species according to the present invention are described below.

In an alternate disclosed embodiment of the present invention, compounds according to the present invention are those of Formula I, wherein R$_a$ is —OCH$_3$; and Z is selected from >C(H$_2$), >C(H)—CH$_3$, >C=CH$_2$, >C=CHCH$_3$ (cis or trans), >C=O, >C(H)—OH, >C(H)—O-alkyl or >C(H)—O-sulfamate.

In another alternate disclosed embodiment of the present invention, compounds according to the present invention are those of Formula I, wherein R$_a$ is —OCH$_2$CH$_3$; and Z is selected from >C(H$_2$), >C(H)—CH$_3$, >C=CH$_2$, >C=CHCH$_3$ (cis or trans), >C=O, >C(H)—OH, >C(H)—O-alkyl or >C(H)—O-sulfamate.

In a further alternate disclosed embodiment of the present invention, compounds according to the present invention are those of Formula I, wherein R$_a$ is —CCCH$_3$; and Z is selected from >C(H$_2$), >C(H)—C$_3$, >C=CH$_2$, >C=CHCH$_3$ (cis or trans), >C=O, >C(H)—OH, >C(H)—O-alkyl or >C(H)—O-sulfamate.

In each of the cases where stereoisomers are possible, both R and S stereoisomers are envisioned as well as any mixture of stereoisomers.

In yet another alternate disclosed embodiment of the present invention, compounds according to the present invention are those of Formula II, wherein R$_a$ is —OCH$_3$.

In another alternate disclosed embodiment of the present invention, compounds according to the present invention are those of Formula II, wherein R$_a$ is —OCH$_2$CH$_3$.

In a further alternate disclosed embodiment of the present invention, compounds according to the present invention are those of Formula II, wherein R$_a$ is —CCCH$_3$.

Those skilled in the art will appreciate that the invention extends to other compounds within the formulae given in the claims below, having the described characteristics. These characteristics can be determined for each test compound using the assays detailed below and elsewhere in the literature.

Although not wishing to be bound by theory, it is believed that 2-methoxyestrone (2ME$_1$) is formed through the same enzymatic pathway as estrone is formed from estradiol. Although not wishing to be bound by theory, it is further believed that the enzymes responsible for this reaction on estradiol are the 17β-hydroxysteroid dehydrogenases (17β-HSD), which utilize NADP+ as a co-factor (Han et al., *J. Biol. Chem.* 275:2, 1105-1111 (2000)). Each of the four members of this enzyme family, types 1, 2, 3, and 4 has distinct activities. It appears that 17β-HSD type 1 catalyzes the reductive reaction (estrone to estradiol), while 17β-HSD type 2 catalyzes the oxidation reaction (estradiol to estrone), and type 3 catalyzes 4-androstenedione to testosterone. It is also believed that an additional metabolic deactivation pathway results in conjugation of 2-methoxyestradiol or 2-methoxyestrone with molecules, such as sulfate or glucuronic acid, and subsequent loss via excretion. In this invention, positions 3 and 17 of 2-methoxyestradiol, and derivatives thereof, may be modified to prevent these metabolic pathways from occurring.

It is well known that orally-delivered steroids, such as estradiol (E$_2$) and ethynyl-E$_2$, are extensively metabolized during passage through the gastrointestinal tract and by first-pass metabolism in the liver. Two major metabolic pathways that lead to rapid deactivation and excretion are well studied viz., oxidation at the D-ring 17-hydroxy group of E) to form estrone and/or conjugation with sulfate and/or glucuronate at the hydroxyls of position 3 on the A-ring and position 17 on the D-ring.

Several studies have been conducted to determine structure activity relationship ("SAR") of 2ME$_2$ analogs (D'Amato, R. J.; Lin, C. M.; Flynn, E.; Folkman, J.; Hamel, E. "Inhibition of Angiogenesis and Breast Cancer in Mice by the Microtubule Inhibitors 2-Methoxyestradiol and Taxol," *Cancer Res.* 1997, 57, 81-86; Cushman, M.; 1-1e, M.-H.; Katzenellenbogen, J. A.; Lin, C. M.; Hamel, E. "Synthesis, Antitubulin and Antimitotic Activity, and Cytotoxicity of Analogs of 2-Methoxyestradiol, an Endogenous Mammalian Metabolite of Estradiol that inhibits Tubulin Polymerization by Binding to the Colchicine Binding Site," *J. Med. Chem.* 1995, 38, 2041-2049; Wang, Z.; Yang, D.; Mohanakrishnan, A. K.; Fanwick, P. E.; Nampoothiri, P.; Hamel, E.; Cushman, M. "Synthesis of B-Ring Homologated Estradiol Analogs that Modulate Tubulin Polymerization and Microtubule Stability," *J. Med. Chem.*, 2000, 43, 2419-2429; Cushman, et. al., *J. Med. Chem.* (1997) 40, 2323-2334.; Wang et al., *Synthetic Comm* 1998, 28, 4431; Cushman et al., *J. Med. Chem.* 2002, 45, 4748; Miller, T. A.; Bulman, A. L.; Thompson, C. D.; Garst, M. E.; Macdonald, T. L., "The Synthesis and Evaluation of Functionalized Estratropinones: Potent Inhibitors of Tubulin Polymerization," *Bioorg & Med. Chem. Letters* 1997, 7, 1851-1856; Miller et al., *J. Med. Chem.* 1997, 7, 1851.), but none to reduce or stop its metabolic pathway.

In the preferred embodiment of the invention, 2-methoxyestradiol, and derivatives thereof, are modified at the 2-, 3- and 17-positions or combinations thereof.

Anti-Proliferative Activity In Vitro

The process or processes by which $2ME_2$ affects cell growth remains unclear, however, a number of studies have implicated various mechanisms of action and cellular targets. $2ME_2$ induced changes in the levels and activities of various proteins involved in the progression of the cell cycle. These include cofactors of DNA replication and repair, e.g., proliferating cell nuclear antigen (PCNA) (Klauber, N., Parangi, S., Flynn, E., Hamel, E. and D'Amato, R. J. (1997), Inhibition of angiogenesis and breast cancer in mice by the microtubule inhibitors 2-methoxyestradiol and Taxol., Cancer Research 57, 81-86; Lottering, M-L., de Kock, M., Viljoen, T. C., Grobler, C. J. S. and Seegers, J. C. (1996) 17β-Estradiol metabolites affect some regulators of the MCF-7 cell cycle. Cancer Letters 110, 181-186); cell division cycle kinases and regulators, e.g., $p34^{cdc2}$ and cyclin B (Lottering et al. (1996); Attalla, H., Mäkelä, T. P., Adlercreutz, H. and Andersson, L. C. (1996) 2-Methoxyestradiol arrests cells in mitosis without depolymerizing tubulin. Biochemical and Biophysical Research Communications 228, 467-473; Zoubine, M. N., Weston, A. P., Johnson, D. C., Campbell, D. R. and Banerjee, S. K. (1999) 2-Methoxyestradiol-induced growth suppression and lethality in estrogen-responsive MCF-7 cells may be mediated by down regulation of p34cdc2 and cyclin B1 expression. Int J Oncol 15, 639-646); transcription factor modulators, e.g., SAPK/JNK (Yue, T-L., Wang, X., Louden, C. S., Gupta, L. S., Pillarisetti, K., Gu, J-L., Hart, T. K., Lysko, P. G. and Feuerstein, G. Z. (1997) 2-Methoxyestradiol, an endogenous estrogen metabolite induces apoptosis in endothelial cells and inhibits angiogenesis: Possible role for stress-activated protein kinase signaling pathway and fas expression. Molecular Pharmacology 51, 951-962; Attalla, H., Westberg, J. A., Andersson, L. C., Aldercreutz, H. and Makela, T. P. (1998) 2-Methoxyestradiol-induced phosphorylation of bcl-2: uncoupling from JNK/SAPK activation. Biochem and Biophys Res Commun 247, 616-619); and regulators of cell arrest and apoptosis, e.g., tubulin (D'Amato, R. J., Lin, C. M., Flynn, E., Folkman, J. and Hamel, E. (1994) 2-Methoxyestradiol, and endogenous mammalian metabolite, inhibits tubulin polymerization by interacting at the colchicine site. Proc. Natl. Acad. Sci. USA 91, 3964-3968; Hamel, E., Lin, C. M., Flynn, E. and D'Amato, R. J. (1996) Interactions of 2-methoxyestradiol, and endogenous mammalian metabolite, with unpolymerized tubulin and with tubulin polymers. Biochemistry 35, 1304-1310), $p21^{WAF1/CIP1}$ (Mukhopadhyay, T. and Roth, J. A. (1997) Induction of apoptosis in human lung cancer cells after wild-type p53 activation by methoxyestradiol. Oncogene 14, 379-384), bcl-2 and FAS (Yue et al. (1997); Attalla et al. (1998)), and p53 (Kataoka, M., Schumacher, G., Cristiano, R. J., Atkinson, E. N., Roth, J. A. and Mukhopadhyay, T. (1998) An agent that increases tumor suppressor transgene product coupled with systemic transgene delivery inhibits growth of metastatic lung cancer in vivo. Cancer Res 58, 4761-4765; Mukhopadhyay et al. (1997); Seegers, J. C., Lottering, M-L., Grobler C. J. S., van Papendorp, D. H., Habbersett, R. C., Shou, Y. and Lehnert B. E. (1997) The mammalian metabolite, 2-methoxyestradiol, affects p53 levels and apoptosis induction in transformed cells but not in normal cells. J. Steroid Biochem. Molec. Biol. 62, 253-267). The effects on the level of cAMP, calmodulin activity and protein phosphorylation may also be related to each other. More recently $2ME_2$ was shown to upregulate Death Receptor 5 and caspase 8 in human endothelial and tumor cell lines (LaVallee T M, Zhan X H, Johnson M S, Herbstritt C J, Swartz G, Williams M S, Hembrough W A, Green S J, Pribluda V S. 2-Methoxyestradiol up-regulates death receptor 5 and induces apoptosis through activation of the extrinsic pathway. Cancer Res. (2003) 63#2:468-75). Additionally, 2ME2 has been shown to interact with superoxide dismutase (SOD) 1 and SOD 2 and to inhibit their enzymatic activities (Huang, P., Feng, L., Oldham, E. A., Keating, M. J., and Plunkett, W. 2000. Superoxide dismutase as a target for the selective killing of cancer cells, Nature. 407:390-5.). All cellular targets described above are not necessarily mutually exclusive to the inhibitory effects of $2ME_2$ in actively dividing cells.

The high affinity binding of $2ME_2$ to sex hormone-binding globulin ("SHBG") has been mechanistically associated to its efficacy in a canine model of prostate cancer, in which signaling by estradiol and 5α-androstan-3α,17β-diol were inhibited by $2ME_2$ (Ding, V. D., Moller, D. E., Feeney, W. P., Didolkar, V., Nakhla, A. M. Rhodes, L., Rosner, W. and Smith, R. G., Sex hormone-binding globulin mediates prostate androgen receptor action via a novel signaling pathway, Endocrinology 139, 213-218 (1998)).

The more relevant mechanisms described above have been extensively discussed in Victor S. Pribluda, Theresa M. LaVallee and Shawn J. Green, 2-*Methoxyestradiol: A novel endogenous chemotherapeutic and antiangiogenic* in The New Angiotherapy, Tai-Ping Fan and Robert Auerbach eds., Human Press Publisher.

Assays relevant to these mechanisms of action and inhibition of cell proliferation are well-known in the art. For example, anti-mitotic activity mediated by effects on tubulin polymerization activity can be evaluated by testing the ability of an estradiol derivative to inhibit tubulin polymerization and microtubule assembly in vitro. Microtubule assembly can be followed in a Gilford recording spectrophotometer (model 250 or 2400S) equipped with electronic temperature controllers. A reaction mixture typically contains 1.0 M monosodium glutamate (pH 6.6), 1.0 mg/ml (10 µM) tubulin, 1.0 mM $MgCl_2$, 4% (v/v) dimethylsulfoxide and 20-75 µM of a composition to be tested. The reaction mixtures are incubated for 15 min. at 37° C. and then chilled on ice. After addition of 10 µl 2.5 mM GTP, the reaction mixture is transferred to a cuvette at 0° C., and a baseline established. At time zero, the temperature controller of the spectrophotometer is set at 37° C. Microtubule assembly is evaluated by increased turbity at 350 nm. Alternatively, inhibition of microtubule assembly can be followed by transmission election microscopy as described in Example 2 of U.S. Pat. Nos. 5,504,074, 5,661, 143, and 5,892,069, the disclosures of which are incorporated herein by reference.

Other such assays include counting of cells in tissue culture plates or assessment of cell number through metabolic assays or incorporation into DNA of labeled (radiochemically, for example $^3$H-thymidine, or fluorescently labeled) or immunoreactive (BrdU) nucleotides. In addition, antiangiogenic activity may be evaluated through endothelial cell migration, endothelial cell tubule formation, or vessel outgrowth in ex-vivo models such as rat aortic rings.

Indications

The invention can be used to treat any disease characterized by abnormal cell mitosis and/or abnormal angiogenesis. Such diseases include, but are not limited to, abnormal stimulation of endothelial cells (e.g., atherosclerosis); solid tumors; blood-borne tumors, such as leukemias; tumor metastasis; benign tumors, for example, hemangiomas, acoustic neuromas, neurofibromas, trachomas, and pyogenic granulomas; vascular malfunctions; abnormal wound healing; inflammatory and immune disorders; Bechet's disease; gout or gouty arthritis; abnormal angiogenesis accompanying: rheumatoid arthritis; skin diseases, such as psoriasis; diabetic retinopathy, and other ocular angiogenic diseases, such as retinopathy of prematurity (retrolental fibroplasia), macular degeneration, corneal graft rejection, neovascular glaucoma; liver diseases and Oster Webber Syndrome (Osler-Weber Rendu disease).

Other undesired angiogenesis involves normal processes including ovulation and implantation of a blastula. The compositions described above can be used as a birth control agent by reducing or preventing uterine vascularization required for embryo implantation. Thus, the present invention provides an effective birth control method when an amount of Formulae I or II sufficient to prevent embryo implantation is administered to a female. In one aspect of the birth control method, an amount of Formulae I or II sufficient to block embryo implantation is administered before or after intercourse and fertilization have occurred, thus providing an effective method of birth control, possibly a "morning after" method. While not wanting to be bound by this theory, it is believed that inhibition of vascularization of the uterine endometrium interferes with implantation of the blastocyte. Similar inhibition of vascularization of the mucosa of the uterine tube interferes with implantation of the blastocyte, preventing the occurrence of a tubal pregnancy. The compositions described above can also be used to block ovulation or to block menstruation (induce amenorrhea).

Diseases associated with neovascularization can be treated according to the present invention. Such diseases include, but are not limited to, ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, and corneal graph rejection.

Other diseases associated with neovascularization can be treated according to the present invention. Such diseases include, but are not limited to, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, and post-laser complications. Other diseases include, but are not limited to, diseases associated with rubeosis (neovascularization of the iris and the angle) and diseases caused by the abnormal proliferation of fibrovascular or fibrous tissue including all forms of proliferative vitreoretinopathy, whether or not associated with diabetes.

The present invention may also be used to treat angiogenesis-dependent cancers including, but not limited to, any one or combination of rhabdomyosarcoma, retinoblastoma, Ewing sarcoma, neuroblastoma, and osteosarcoma. Other angiogenesis-dependent cancers treatable with the present invention include, but are not limited to, breast cancer, prostrate cancer, renal cell cancer, brain cancer, ovarian cancer, colon cancer, bladder cancer, pancreatic cancer, stomach cancer, esophageal cancer, cutaneous melanoma, liver cancer, small cell and non-small cell lung cancer, testicular cancer, kidney cancer, bladder cancer, cervical cancer, lymphoma, parathyroid cancer, penile cancer, rectal cancer, small intestine cancer, thyroid cancer, uterine cancer, Hodgkin's lymphoma, non-Hodgkin's lymphoma, lip cancer, oral cancer, skin cancer, leukemia or multiple myeloma.

As mentioned above, another disease that can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Other diseases that can be treated according to the present invention are hereditary hemorrhagic telangiectasia, osteoarthritis, chronic inflammation, Crohn's disease, ulcerative colitis, Bartonellosis, inflammatory or immune mediated bowel disease and acquired immune deficiency syndrome.

The present invention can be used to treat eye conditions in humans or animals, wherein the eye conditions include, but are not limited to, ocular neovascular disease, diabetic retinopathy, retinopathy of prematurity, macular degeneration, corneal graft rejection, neovascular glaucoma, retrolental fibroplasias, epidemic keratoconjunctivitis, contact lens overwear, atopic keratitis, superior limbic keratitis, pterygium keratitis sicca, myopia, chronic retinal detachment, optic pits, Terrien's marginal degeneration, hyperviscosity syndromes, chronic uveitis, chronic vitritis, presumed ocular histoplasmosis, retinitis, choroiditis, proliferative vitreoretinopathy, scleritis, Eales' disease, Best's disease, trachoma, or post-laser complications.

The present invention can be used to treat inflammatory or immune mediated diseases in humans or animals, wherein the inflammatory or immune mediated diseases include, but are not limited to, rheumatoid arthritis, osteoarthritis, ulcerative colitis, Crohn's disease. Mooren's ulcer, arthritis, sarcoidosis, inflammatory or immune mediated bowel disease, systemic lupus, Wegener's syndrome, Stevens-Johnson disease, Behcet's disease, pemphigoid, Lyme's disease, asthma or acquired immune deficiency syndrome.

The present invention can be used to treat infectious diseases in humans or animals, wherein the infectious diseases include, but are not limited to syphilis, a bacterial infection, a Mycobacterial infection, a bacterial ulcer, a fungal ulcer, a Herpes simplex infection, a Herpes zoster infection, a protozoan infection, a Bartonellosis infection, or toxoplasmosis.

The present invention can be used to treat blood or blood vessel diseases in humans or animals, wherein the blood or blood vessel diseases include, but are not limited to, vein occlusion, artery occlusion, carotid obstructive disease, polyarteritis, atherosclerosis, Osler-Weber-Rendu disease, sickle cell anemia, leukemia, acute or chronic neoplastic disease of the bone marrow, hemangiomas, hereditary hemorrhagic telangiectasia, disease of the bone marrow, anemia, impaired blood clotting or enlargement of the lymph nodes, liver, or spleen. The present invention can also be used to treat chronic neoplastic disease of the bone marrow, wherein those diseases include, but are not limited to, multiple myeloma and myelo dysplastic syndrome.

The present invention can be used to treat skin conditions in a humans or an animals, wherein the skin conditions include, but are not limited to, abnormal wound healing, acne rosacea, chemical burns of the skin, dermatitis or psoriasis.

In addition, the invention can be used to treat a variety of post-menopausal symptoms, osteoporosis, cardiovascular disease, myocardial angiogenesis, plaque neovascularization, hemophiliac joints, angiofibroma, wound granulation, intestinal adhesions, scleroderma, hypertrophic scars; i.e., keloids. They are also useful in the treatment of diseases that have angiogenesis as a pathologic consequence, such as cat scratch disease, and *Helicobacter pylori* ulcers. The invention can also be used to treat Alzheimer's disease, to reduce the incidence of stroke, and as an alternative to prior estrogen replacement therapies. The compounds of the present invention can work by estrogenic and non-estrogenic biochemical pathways.

Additionally, the compounds of the present invention can be used to treat endometriosis. Endometriosis is the abnormal growth of endometrial cells; the same cells that line the uterus that are shed monthly in the menstrual process. Wayward endometrial cells can position themselves in the lower abdomen on areas such as the cul-de-sac, the recto-vaginal septum, the stomach, the fallopian tubes, the ovaries, and the bladder. During menstruation, the normal uterine lining is sloughed off and expelled through the vagina, but transplanted endometrial tissue has no means of exiting the body; instead the endometrial tissue and cells adhere and grow where positioned. The results are internal bleeding, inflammation, and scarring. One of the serious consequences of endometrial scarring is infertility. The endometrial growths are generally not malignant or cancerous. Among other complications, the growths can rupture and can spread the endometriosis to new areas of the lower abdomen. Endometriosis is a progressive disease. The growths or lesions are first seen as clear vesicles, then become red, and finally progress to black lesions over a period of seven to ten years.

Pharmaceutical Preparations

Also contemplated by the present invention are implants or other devices comprised of the compounds or drugs of Formulae I or II or prodrugs thereof where the drug or prodrug is formulated in a biodegradable or non-biodegradable polymer for sustained release. Non-biodegradable polymers release the drug in a controlled fashion through physical or mechanical processes without the polymer itself being degraded. Biodegradable polymers are designed to gradually be hydrolyzed or solubilized by natural processes in the body, allowing gradual release of the admixed drug or prodrug. The drug or prodrug can be chemically linked to the polymer or can be incorporated into the polymer by admixture. Both biodegradable and non-biodegradable polymers and the process by which drugs are incorporated into the polymers for controlled release are well known to those skilled in the art. Examples of such polymers can be found in many references, such as Brem et al., *J. Neurosurg* 74: pp. 441-446 (1991). These implants or devices can be implanted in the vicinity where delivery is desired, for example, at the site of a tumor or a stenosis.

Because anything not formed in the body as a natural component may elicit extreme and unexpected responses, such as blood vessel closure due to thrombus formation or spasm, and because damage to blood vessels by the act of insertion of a vascular stent may be extreme and unduly injurious to the blood vessel surface, it is prudent to protect against such events. Restenosis is a re-narrowing or blockage of an artery at the same site where treatment, such as an angioplasty or stent procedure, has already taken place. If restenosis occurs within a stent that has been placed in an artery, it is technically called "in-stent restenosis," the end result being a narrowing in the artery caused by a build-up of substances that may eventually block the flow of blood. The compounds that are part of the present invention are especially useful to coat vascular stents to prevent restenosis. The coating should preferably be a biodegradable or non-biodegradable polymer that allows for a slow release of a compound of the present invention thereby preventing the restenosis event.

The present invention also relates to conjugated prodrugs and uses thereof. More particularly, the invention relates to conjugates of steroid compounds, such as compounds of Formulae I or II, and the use of such conjugates in the prophylaxis or treatment of conditions associated with enhanced angiogenesis or accelerated cell division, such as cancer, and inflammatory conditions, such as asthma and rheumatoid arthritis and hyperproliferative skin disorders including psoriasis. The invention also relates to compositions including the prodrugs of the present invention and methods of synthesizing the prodrugs.

In one aspect, the present invention provides a conjugated prodrug of an estradiol compound, preferably compounds of Formulae I or II, conjugated to a biological activity modifying agent.

Alternatively, the conjugated prodrug according to the present invention includes the compounds of Formulae I or II conjugated to a peptide moiety.

The incorporation of an estradiol compound such as the compounds of Formulae I or II, into a disease-dependently activated pro-drug enables significant improvement of potency and selectivity of this anti-cancer and anti-inflammatory agent.

In addition to the compounds of the present invention, the pharmaceutical composition of this invention may also contain, or be co-administered (simultaneously or sequentially) with, one or more pharmacological agents of value in treating one or more disease conditions referred to hereinabove.

A person skilled in the art will be able by reference to standard texts, such as Remington's Pharmaceutical Sciences 17th edition, to determine how the formulations are to be made and how these may be administered.

In a further aspect of the present invention there is provided use of compounds of Formulae I or II or prodrugs thereof according to the present invention for the preparation of a medicament for the prophylaxis or treatment of conditions associated with angiogenesis or accelerated cell division or inflammation.

In a further aspect of the present invention there is provided a pharmaceutical composition comprising compounds of Formulae I or II or prodrugs thereof according to the present invention, together with a pharmaceutically acceptable carrier, diluent or excipient.

The pharmaceutical composition may be used for the prophylaxis or treatment of conditions associated with angiogenesis or accelerated cell division or inflammation.

In a still further aspect of the present invention there is provided a method of prophylaxis or treatment of a condition associated with angiogenesis or accelerated or increased amounts of cell division hypertrophic growth or inflammation, said method including administering to a patient in need of such prophylaxis or treatment an effective amount of compounds of Formulae I or II or prodrugs thereof according to the present invention, as described herein. It should be understood that prophylaxis or treatment of said condition includes amelioration of said condition.

By "an effective amount" is meant a therapeutically or prophylactically effective amount. Such amounts can be readily determined by an appropriately skilled person, taking into account the condition to be treated, the route of administration and other relevant factors. Such a person will readily be able to determine a suitable dose, mode and frequency of administration.

Pharmaceutically acceptable salts of the compounds of the Formulae I or II may be prepared in any conventional manner for example from the free base and acid. In vivo hydrolysable esters, amides and carbamates of Formulae I or II may be prepared in any conventional manner.

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into polymers allowing for sustained release, the polymers being implanted in the vicinity of where delivery is desired, for example, at the site of a tumor or within or near the eye. The dosage of the composition will depend on the condition being treated, the particular derivative used, and other clinical factors such as weight and condition of the patient and the route of administration of the compound. However, for oral administration to humans, a dosage of 0.01 to 100 mg/kg/day, especially 0.01-20 mg/kg/day, is generally preferred.

The formulations in accordance with the present invention can be administered in the form of tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, or a transdermal patch.

The formulations include those suitable for oral, rectal, nasal, inhalation, topical (including dermal, transdermal, buccal and sublingual), vaginal, parenteral (including subcutaneous, intramuscular, intravenous, intradermal, intraocular, intratracheal, and epidural) or inhalation administration. The formulations may conveniently be presented in unit dosage form and may be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or Finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken; i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in freeze-dried (lyophilized) conditions requiring only the addition of a sterile liquid carrier, for example, water for injections, immediately prior to use. Extemporaneous injection solutions and suspensions may be prepared from sterile powders, granules and tablets of the kinds previously described.

Preferred unit dosage formulations are those containing a daily (lose or unite daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

The present invention includes compositions and methods for treating mammalian disease characterized by pathogenic angiogenesis by administering compounds of Formulae I or II. The 2-methoxyestradiol, and derivatives thereof, are modified at the 2-, 3- and 17-positions or combinations thereof. Combinations which are physically impossible are not contemplated by this invention, such as a carbon atom containing 5 bonds.

100% pure isomers are contemplated by this invention, however a stereochemical isomer (labeled as α or β, or as R or S) may be a mixture of both in any ratio, where it is chemically possible by one skilled in the art. Also contemplated by this invention are both classical and non-classical bioisosteric atom and substituent replacements, such as are described by Patani and Lavoie ("Bio-isosterism: a rational approach in drug design" Chem. Rev. (1996) p. 3147-3176) and are well known to one skilled in the art. Such bioisosteric replacements include, for example, but are not limited to, substitution of =S or =NH for =O.

Improved Estradiol Derivative Synthesis

Known compounds that are used in accordance with the invention and precursors to novel compounds according to the invention can be purchased, e.g., from Sigma Chemical Co., Steraloids or Research Plus. Other compounds according to the invention can be synthesized according to known methods from publicly available precursors.

The 2-position of estradiol can be modified according to known methods, such as those described in U.S. Pat. No. 6,136,992 (2000) (incorporated herein by reference); Siya Ram et al., 2-Alkoxy estradiols and derivatives thereof (incorporated herein by reference); Cushman et al., *J. Med. Chem.* (1995) 38, 2041-2049; Cushman, et. al., J. Med. Chem. (1997) 40, 2323-2334; U.S. Pat. No. 6,448,419 (2002); Paaren et al., Wang et al, *Synthetic Comm* 1998, 28, 4431, Cushman et al., *J. Med. Chem.* 1995, 38, 2041, Cushman et al., *J. Med. Chem.* 2002, 45, 4748), or other publications, incorporated herein by reference.

The synthetic routes for the series of analogs disclosed by this invention are summarized in Schemes 1-6. Schemes 1-4 show the preparation of singly and doubly substituted templates that are required as precursors for the triply substituted analogs. Schemes 3 and 5 demonstrate how 3-carboxamides can be prepared from the templates. These synthetic routes present one potential way to prepare this series of analogs, and other synthetic routes (including modifying the order of synthetic steps or reagents) are possible to those skilled in the art.

In Scheme 1, the 2-methoxy, 2-ethoxy or 2-propynyl derivatives, which are either commercially available or can be readily prepared by literature methods, are oxidized using the Oppenauer oxidation. The resulting ketone can be deoxygenated using the Wolf-Kishner reduction (Shapiro R. J. et al., *J. Org. Chem.* 1964, 86, 2825-2832.) or olefinated (Schow et al., *J. Org. Chem.* 1979, 44, 22; Krubner et al., *J. Org. Chem.* 1968, 33, 1715.) using the Wittig reaction. Both the 17-methylene and 17-ethylene estrane analogs can be reduced to the alkane using catalytic reduction (Pd on activated carbon, $H_2$).

In specific cases, the nature of protecting groups or the order of reactions may have to be altered to reach the desired products. These changes to the general synthetic schemes would be well understood to one skilled in the art. For instance, in the case where the desired 2-functionality is a propyne and the desired 17-functionality is an alkyl group, catalytic hydrogenation can not be carried out on the 17-olefin since the 2-alkyne would also be reduced. Scheme 2 presents a synthetic route to prepare analog 18. In this example, the 17-methyl is introduced as in Scheme 1 starting with estrone, and subsequently the 2-propyne is incorporated using a literature method (Cushman et al., *J. Med. Chem.* 2002, 45, 4742).

Scheme 3 demonstrates the preparation of compounds 33-38. 2-Methoxyestradiol can be converted selectively to 3-triflate-2-methoxyestradiol using 4-nitrophenyl trifluorosulfonate (*J. Org. Chem.* 1999, 64, 178). The 17-hydroxy can be converted to the sulfamate with sulfamoyl chloride and either sodium hydride (Howarth et al., *J. Med. Chem.* 1994, 37, 219) or 2,6-di-tert-butyl-4-methylpyridine (Coibanu et al., *J. Med. Chem.* 1999, 42, 2280) or alkylated using the Williamson ether synthesis. The ether or sulfamate can then be converted to the carboxamide using the Morera procedure (*Tetrahedron Letters*, 1998, 39, 2835-2838). She triflate is a versatile synthetic intermediate and can be used to incorporate a wide range of functional groups at position 3. Alternate paths to the carboxamide could also utilize a carboxylic acid (Shi et al., *Chem. & Biol.* 2001, 8, 501); then conversion to a carboxamide with thionyl chloride and ammonia gas (Tomas de, Paulis, et. al., *J. Med. Chem.* 1986, 29, 61). Alternatively, an ester can be used which can be transformed to a carboxamide with ammonia. Nitriles (Weissman et al., *J. Org. Chem.* 2005, 70, 1509) can also be converted to amides (hydrolysis: NaOH and $H_2O_2$). Generally speaking, aryl halides and triflates are interchangeable in Pd catalyzed reactions, such as the ones contemplated herein.

Scheme 4 demonstrates one possible route for preparation of 2-methoxy-1,3,5(10)16-estratetraene-3-ol using the Shapiro reaction. See U.S. Pat. No. 5,783,571, incorporated herein by reference.

Scheme 5 demonstrates one possible route using triflic anhydride and pyridine to convert templates 4-12, 16, 17, 23 and 39-41 to the corresponding triflates (Echvarren et al., *J. Am. Chem.* 1987, 109, 5478). These triflates can be converted to the respective carboxamides using Morera's procedure as discussed above. Ketones 54, 55 and 56 can be converted to the 17-hydroxy analogs by mild reduction with sodium borohydride as shown in Scheme 6.

To one skilled in the art, there are multiple alternative synthetic paths that can be used to prepare these compounds. While the synthetic pathways discussed above have been put to practice, these paths are not the only viable routes available to one skilled in the art. All of these compounds can be prepared from either estrone or estradiol, and other reactions, such as the Barton deoxygenation, Clemmensen reduction, Tebbe reaction and alcohol dehydration, among other possible reactions, can be used to incorporate the 17-modification. Carboxamides and esters can be prepared from the corresponding carboxylic acids using known chemical or enzymatic amidation techniques.

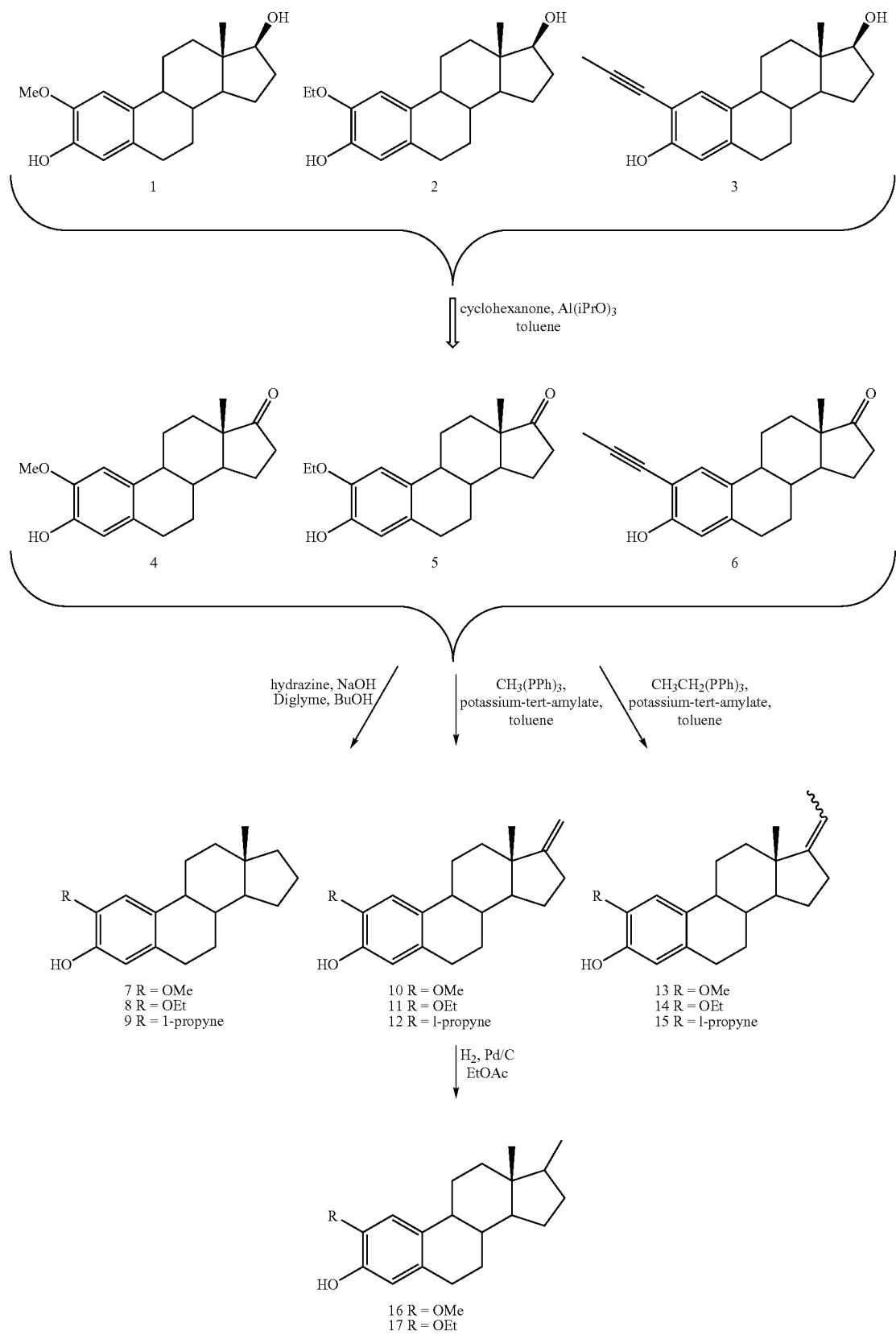

21
22
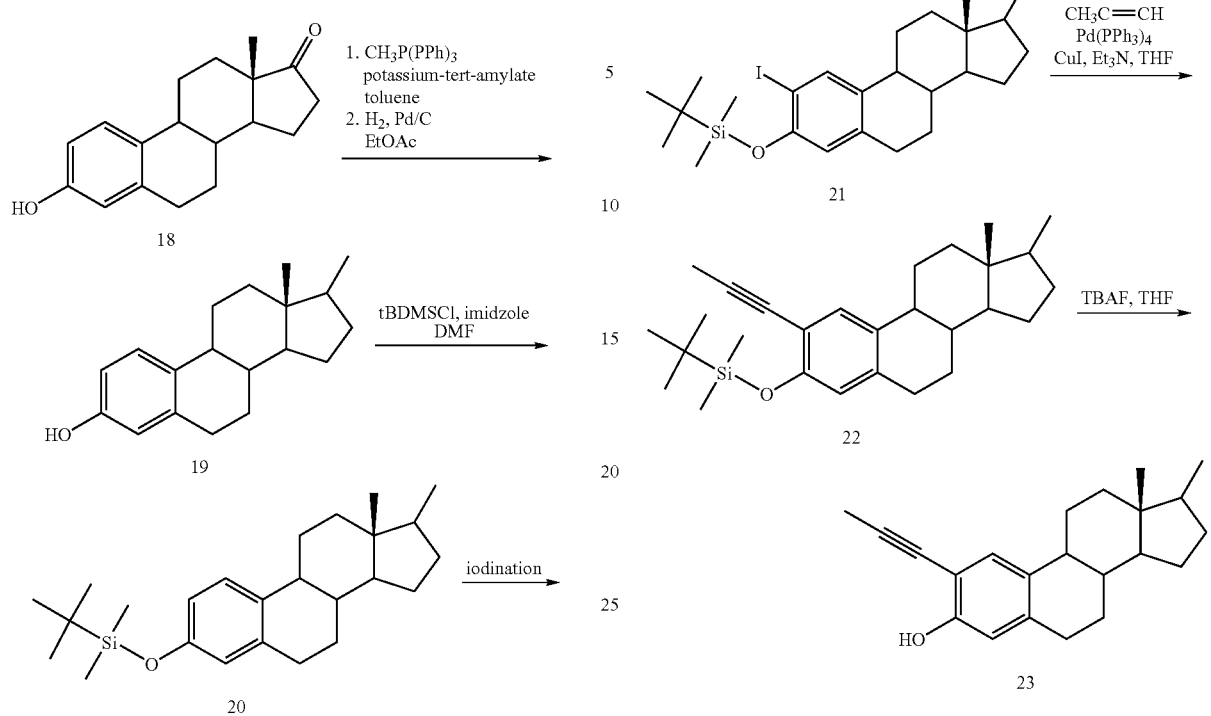
-continued
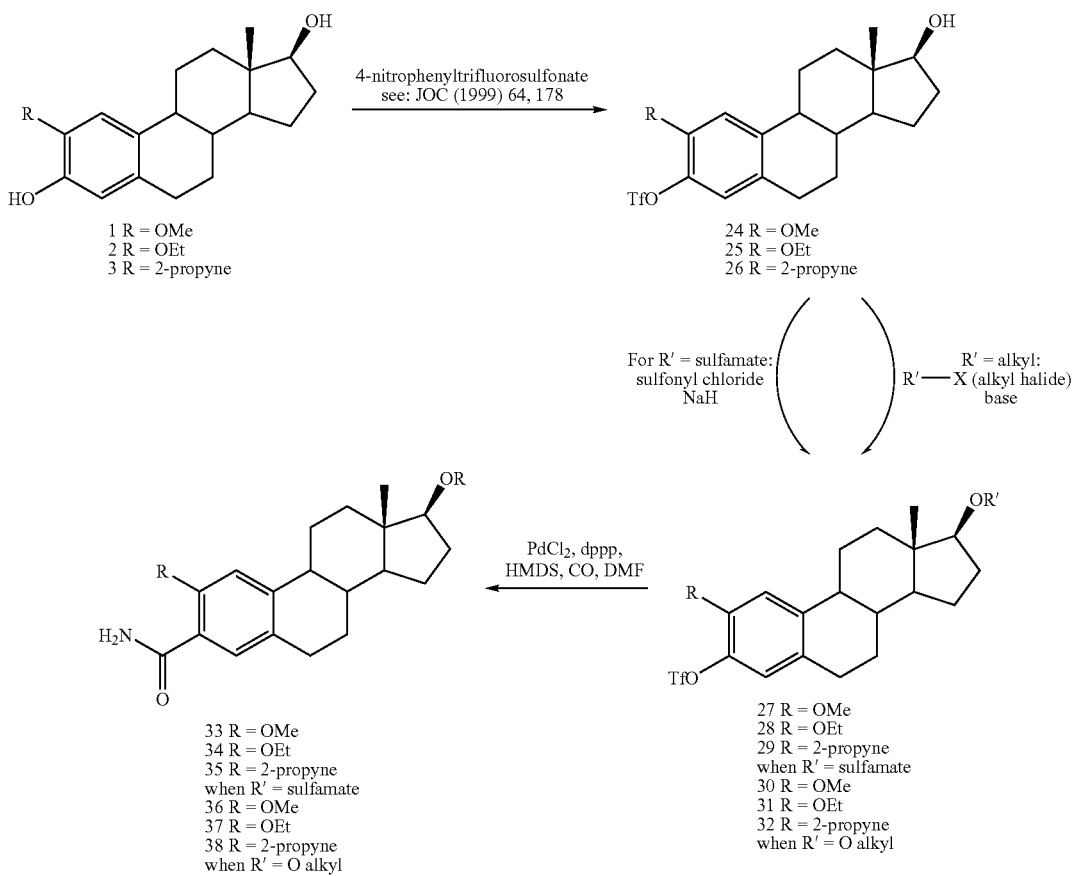

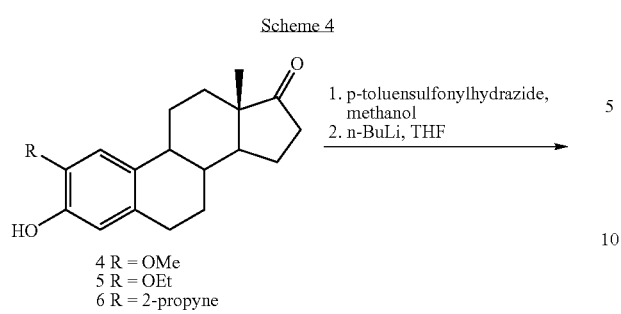
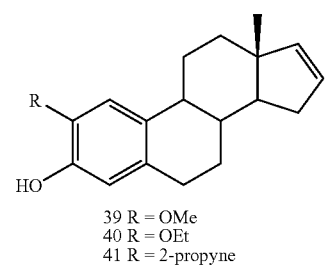
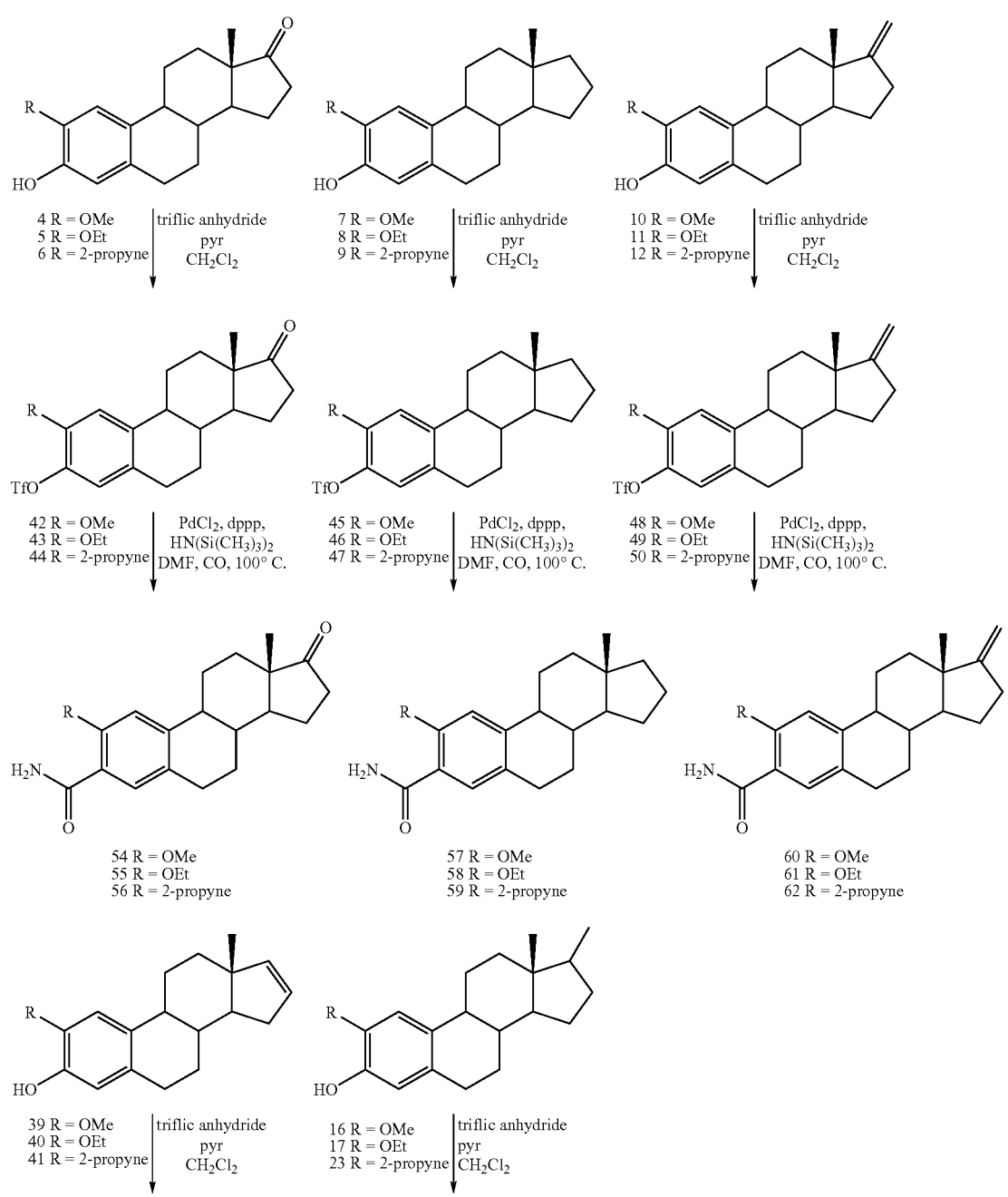

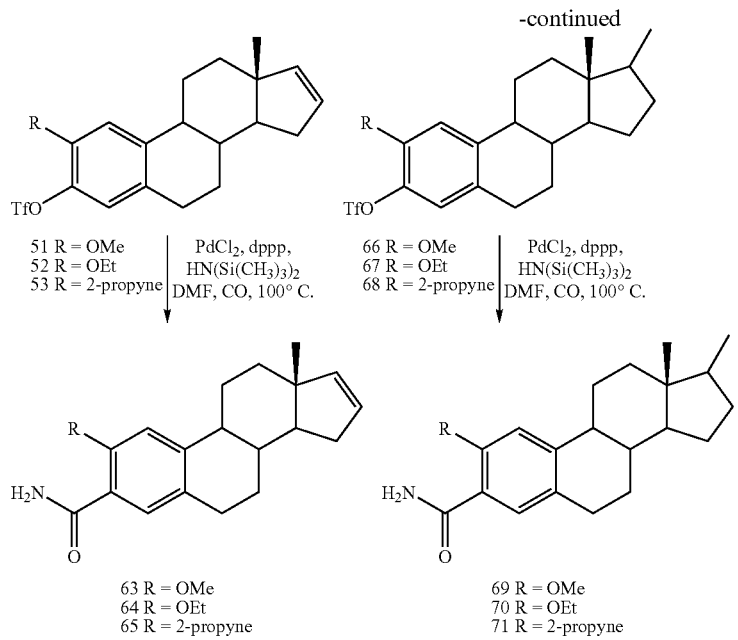

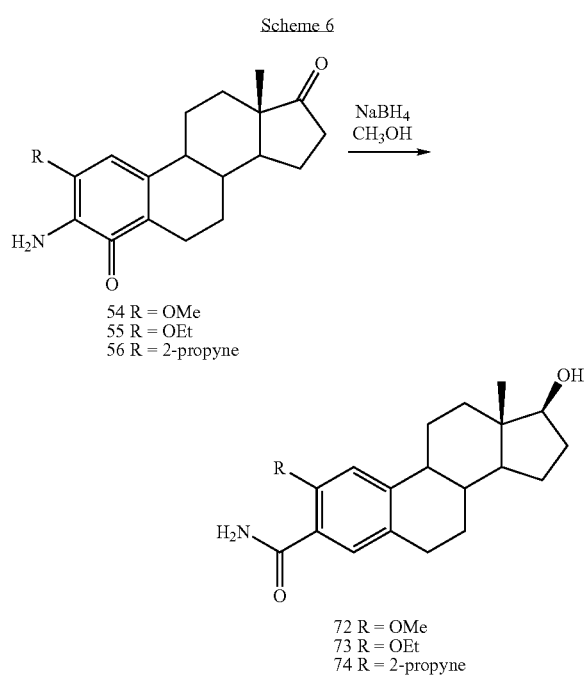

EXPERIMENTAL EXAMPLES

Representative Oppenauer Oxidation

Preparation of 2-methoxyestra-1,3,5(10)-trien-17-one (4)

2-Methoxyestradiol (Scheme 1, Compound 1) (10 g, 33.1 mmol) was placed in a 1 L round bottom flask that was equipped With a 25 mL, Dean-Stark trap and a reflux condenser. The entire apparatus had been flame dried under an argon atmosphere. Toluene (400 mL) was added to dissolve the starting material. Aluminum isopropoxide (34.6 g, 169 mmol) and cyclohexanone (135 mL, 1.3 mol) were added and the entire reaction mixture was heated at reflux (145°-150° C.) for 20 h. Saturated aqueous sodium bicarbonate solution (200 mL) was added after the reaction mixture was allowed to cool to room temperature. The organic material was extracted with dichloromethane (3×300 mL). The aqueous emulsion was acidified with 3 N HCl (~20 mL) until the emulsion separated and the aqueous layer was extracted with ethyl acetate (2×75 mL). The combined organic extracts were dried over magnesium sulfate and condensed using a rotary evaporator. The cyclohexanone and cyclohexanol were removed by vacuum distillation. When the distillation pot was cool enough, hexane was added and 2-methoxyestrone (Scheme 1, Compound 4) precipitated out of solution. 7.72 g (25.7 mmol, 78%) of product was obtained. $^1$H NMR (300 MHz, CDCl$_3$) δ 6.81 (s, 1H), 6.68 (s, 1H), 5.46 (s, 1H), 3.88 (s, 3H), 2.89-2.76 (m, 2H), 2.61-1.24 (m, 13H), 0.94 (s, 3H).

Representative Wolf-Kishner Reduction

Preparation of 2-Methoxyestra-1,3,5(10)-triene-3-ol (7)

2-Methoxyestrone (Scheme 1, Compound 4) (450 mg, 1.5 mmol) was suspended in ethylene glycol (10 mL) and n-butanol (2 mL). Hydrazine hydrate (0.145 mL, 3 mmol) was added and the mixture was heated to 130° C. for 1 h. The reaction was cooled to 70° C., KOH (253 mg, 4.5 mmol) was added, then the reaction vas heated at 200° C. for 1 h. The mixture was cooled to room temperature, poured into ice and HCl (6N, 6 mL) was added. The resulting solid was filtered off. The solid was dissolved in acetone, which was then evaporated to give a product (Scheme 1, Compound 7) (310 mg, 72% yield). $^1$H NMR (300 MHz, CDCl$_3$) δ 6.93 (1H, s, aromatic), 6.75 (1H, s, aromatic), 5.35 (1H, s, phenol), 3.95 (3H, s, methoxy), 2.95 (2H, dd, J=5.0, 3.0 Hz), 2.25 (2H, m,), 1.95 (2H, m), 1.95-1.05 (11H, m), 0.8 (3H, s)

Representative Wittig Olefination

Preparation of 17(20)-methleneestra-1,3,5(10)-trien-3-ol (10)

Potassium-tert-amylate (1.54 M, toluene, 4.35 mL 6.69 mmol), (prepared as in Schow et al., *J. Org. Chem.* 1979, 44, 3760) (potassium-tert-butoxide is an alternate base) was added to a suspension of methyl triphenylphosphonium bromide (2.39 g, 6.69 mmol) in anhydrous benzene and refluxed for 30 min. 2-Methoxyestrone (Scheme 1, Compound 4) (300 mg, 1 mmol) in warm benzene (5 mL) was added and the mixture was refluxed for 3 h. The reaction was cooled to room temperature, poured into 100 mL, water, and washed with ether (2×100 mL). The combined organics were washed with 6 HCl (1×100 mL), NaHCO$_3$ (saturated, 1×100 mL), water (1×100 mL), and brine (1×100 mL). The combined organics were then dried with sodium sulfate, titered and rotoevaporated to give a semi-solid, yellowish oil. This product was purified by silica gel column chromatography using 95:5 chloroform:methanol as an eluent. 220 mg 17(20)-methyleneestra-1,3,5(10)-triene-3-ol (Scheme 1, Compound 10) (0.738 mmol, 73% yield) was obtained. $^1$H NMR (300 MHz, CDCl$_3$) δ 6.83 (s, 1H), 6.67 (s, 1H), 5.44 (br s, 1H), 4.70 (t, J=2.26 Hz, 2H), 3.89 (s, 3H), 2.86-2.74 (m, 2H), 2.64-2.49 (m, 1H), 2.39-2.17 (m, 3H), 2.02-1.78 (m, 3H), 1.65-1.19 (m, 4H), 0.85 (s, 3H). $^{13}$C NMR (75 MHz, CDCl$_3$) δ 162.2, 144.9, 143.8, 132.3, 130.0, 115.0, 108.5, 101.2, 77.6, 56.5, 53.9, 44.7, 39.2, 36.2, 29.9, 29.5, 28.1, 27.3, 24.3, 19.0. Elemental analysis (C$_{20}$H$_{26}$O$_2$) calculated C=80.48, H=8.79. Found C=80.60, H=8.77.

Representative Shapiro Reaction

Scheme 4

Preparation of 2-Methoxyestrone p-toluensulfonylhydrazone

2-Methoxyestrone (Scheme 4, Compound 4) (1.011 g, 2.3 mmol) and p-toluensulfonylhydrazide (775 mg, 4.17 mmol) were dissolved in anhydrous methanol (10 mL) in a flame dried 50 ml round bottomed flask. The mixture was refluxed for 24 h, after which the contents were transferred to a 50 ml Erlenmeyer flask and cooled to room temperature. Solvent was removed under reduced pressure to give an orangish foam, which was used without further purification (1.5757 g. quantitative yield). Selected $^1$H-NMR (300 MHz, CDCl$_3$) δ 7.87 (d, J=8 Hz, 21-1), 7.23 (d, J=8 Hz, 2H), 6.92 (br s, 1H), 6.80 (s, 1H), 6.66 (s, 1H), 5.45 (br s, 1H), 3.88 (s, 3H), 2.85-2.70 (m, 2H), 2.45 (s, 31-1), 2.41-1.2 (m, 13H), 0.85 (s, 3H).

Preparation of 2-methoxy-1,3,5(10)16-estratetraene-3-ol (39)

2-Methoxyestrone p-tosylhydrazone (1.5757 g, 3.3 mmol) was dissolved in anhydrous tetrahydrofuran (50 mL) in a flame dried 250 ml., round bottomed flask and cooled to −10° C. The mixture was stirred and n-butyl lithium (5.3 mL, 2.5 M in hexanes) was added dropwise. The mixture was warmed to room temperature over 3 days. Ice (~5 g) was added, followed by saturated ammonium chloride (~50 mL). The mixture was transferred to a 250 mL separatory funnel, shaken, and separated. The aqueous layer was washed with ether (50 mL) and the organics were combined. The organics were washed with saturated sodium bicarbonate (50 mL) and brine (50 mL). The organics were dried with magnesium sulfate, filtered and solvent was removed under reduced pressure. The resulting solid was dissolved in acetone (~10 mL) and solvent was removed under reduced pressure two times. Crystalline 2-methoxy-1,3,5(10)16-estratetraene-3-ol (Scheme 4, Compound 39) was obtained (845 mg, 90% yield). H-NMR (300 MHz, CDCl$_3$) δ 6.81 (s, 1H), 6.68 (s, 1H), 5.97-5.91 (m, 1H), 5.80-5.74 (m, 1H), 5.43 (s, 1H), 3.88 (s, 3H), 2.90-2.71 (m, 2H), 2.38-1.34 (m, 11H), 0.82 (s, 3H).

Representative Preparation of Triflic Esters

Preparation of 2-Methoxy-17-oxoestra-1,3,5(10)-trien-3-yl(trifluoromethyl)sulfonate (42)

A 2-L 3-neck round-bottomed flask fitted with an overhead stirrer, dropping funnel, and nitrogen inlet was charged with 2-methoxyestrone (Scheme 5, Compound 4) (35 g, 0.116 mol), anhydrous methylene chloride (1300 mL), and anhydrous pyridine (330 mL), and cooled externally with an ice-water bath. Trifluoromethanesulfonic anhydride (32.5 mL, 0.193 mmol) was then added dropwise over 1 hour, while the temperature was maintained below 5° C. The mixture was stirred an additional hour, and poured into 1 N HCl (2 L). The organic layer was removed, the aqueous layer was extracted with additional methylene chloride (300 mL), and the combined organic layers were extracted with 1 N HCl (2 L). The aqueous layer was extracted with methylene chloride (300 mL), and the total combined organic layers were washed with 1 N HCl (1 L) at which point the pal of the aqueous phase was acidic (pH paper). The organic layer was washed with brine (1 L) and dried over sodium sulfate (370 g). Suction-filtration through a plug of silica gel 60 (150 g) and concentration afforded a brown foam (39.7 g) which was purified by flash column chromatography using 550 g of silica gel 60, eluted with 3:1 hexanes/methylene chloride (2 L) then methylene chloride (4 L). Product-containing fractions were concentrated affording 36.05 g (72%) of 2-methoxy-17-oxoestra-1,3,5(10)-trien-3-yl(trifluoromethyl)sulfonate (Scheme 5, Compound 42) as a white solid, which was used without further purification. H NMR (300 MHz, CDCl$_3$) δ 6.96 (s, 1H), 6.95 (s, 1H), 3.90 (s, 3H), 2.87 (dd, J=4.2, 6.4 Hz) 2.61-2.95 (m, 8H), 1.74-1.36 (m, 5H), 0.94 (s, 3H).

Preparation of 2-Methoxyestra-1,3,5(10)-trien-3-yl (trifluoromethyl)sulfonate (45)

A 2-L 3-neck round-bottomed flask, fitted with an overhead stirrer, a Claisen adaptor with a nitrogen inlet and a thermocouple probe, and a septum, was charged with 2-methoxyestra-1,3,5(10)-trien-3-ol (Scheme 5, Compound 7) (18 g, 62.84 mmol, anhydrous dichloromethane (750 mL) and pyridine (170 mL). The resulting solution was stirred under nitrogen, extremely cooled using an ice-water bath, and treated with trifluoromethanesulfonic anhydride (16 mL, 94.26 mmol) over 1.5 hours while maintaining the internal reaction temperature below 2° C. The resulting dark mixture was stirred an additional 1 h at which point TLC analysis (dichloromethane) indicated complete loss of starting material and the formation of a new upper-R$_f$ spot. The reaction mixture was poured into 1 N hydrochloric acid (2000 mL) and the phases were partitioned. The aqueous phase was extracted with dichloromethane (2×300 mL) and the combined organic layers were washed with brine (200 mL), dried over sodium sulfate (500 g), filtered, concentrated to dryness, dissolved in a mixture of 1:1 dichloromethane-hexanes, and suction-filtered through a plug of silica gel 60 (150 g), eluting with an additional 1000 mL of the same solvent system. The colorless filtrate was concentrated to afford 24.3 g (92%) of the desired compound (Scheme 5, Compound 45), after drying to a constant weight under high vacuum (1 torr) at ambient temperature. The compound was used in the next step without further purification. $^1$H NMR (300 MHz, CDCl$_3$) δ 6.98 (s, 1H), 6.90 (s, 1H), 3.88 (s, 3H), 2.85 (m, 2H), 2.32 (m, 2H), 1.95 (m, 2H), 1.80-1.58 (m, 6H), 1.42-1.05 (m, 8H), 0.80 (s, 3H).

Preparation of 2-Methoxy-17-methyleneestra-1,3,5 (10)-trien-3-yl(trifluoromethyl)sulfonate (48)

A 3-L 3-neck round-bottomed flask fitted with an overhead stirrer, dropping funnel, nitrogen inlet and temperature probe, was charged with 17(20)-methyleneestra-1,3,5(10)-triene-3-ol (Scheme 5, Compound 10) (47.0 g, 0.158 mmol), anhydrous methylene chloride (1.75 L), and anhydrous pyridine (450 mL), then cooled externally with an ice-water bath. Trifluoromethanesulfonic anhydride (40.0 mL, 0.238 mmol) was added dropwise over 1 hour while maintaining the temperature below 5° C. After an additional 4 hours, TLC analysis indicated complete conversion of the starting material (new upper $R_f$ spot, methylene chloride). The reaction mixture was poured into 1 N HCl (3 L). The organic layer was removed, the aqueous layer was extracted with methylene chloride (3×500 mL), and the combined organic layers were extracted with 1 N HCl (2 L). The aqueous layer was extracted with methylene chloride (500 mL) and the combined organic layers were washed with 1 N HCl (1 L). The aqueous layer was extracted with methylene chloride (500 mL) at which point the pH of the aqueous phase was acidic (pH paper). The combined organic layer was washed with brine (1 L) and dried over sodium sulfate. Suction-filtration through a plug of silica gel (305 g) and concentration afforded 66.1 g (97%) of triflate (Scheme 5, Compound 48) as a yellow solid. $^1$H NMR (300 MHz, CDCl$_3$) δ 6.98 (s, 1H), 6.92 (s, 1H), 4.71 (s, 2H), 3.91 (s, 3H), 2.91-2.72 (m, 2H), 2.66-1.18 (m, 13H), 0.85 (s, 3H).

Preparation of 2-methoxy-3-triflic-1,3,5(10)16-estratetraene (51)

2-Methoxy-1,3,5(10)16-estratetraene-3-ol (Scheme 5, Compound 39) (2.258 g, 8.89 mmol) was dissolved in anhydrous dichloromethane (80 mL) and anhydrous pyridine (22 mL, 272 mmol) and cooled to 0° C. Triflic anhydride (12.6 mL, 74.6 mmol) was added dropwise and the mixture was stirred for 18 h with warming to rt. The mixture was poured into water (200 mL) and washed with dichloromethane (2×200 mL). The organics were washed with 2 M HCl (2×200 mL) water (200 mL) and brine (200 mL). The organics were dried with Na$_2$SO$_4$, filtered and the solvent was reduced pressure. The crude product was purified with a Biotage FLASH SiO$_2$ column (99:1 hexanes:ethyl acetate). 3.195 g of 2-methoxy-3-triflic-1,3,5(10)16-estratetraene (Scheme 5, Compound 51) was obtained (7.68 mmol, 86% yield). H-NMR (300 MHz, CDCl$_3$ δ 6.96 (s, 1H), 6.93 (s, 1H), 5.93 (ddd, J=4.5, 1.7, 1 Hz, 1H), 5.80-5.75 (m, 1H), 3.90 (s, 1H), 2.90-2.78 (m, 2H), 2.39-1.21 (m, 11H), 0.82 (s, 3H).

Representative Carboxamidations

General Procedure Based on Tetrahedron Lett 1998 39, 2835-2838

Preparation of 2-methoxy-17-oxoestra-1,3,5(10)-triene-3-carboxamide (54)

A 1-L 3 neck round-bottomed flask equipped with an overhead stirrer, reflux condenser, nitrogen inlet and thermocouple, was charged with 2-methoxy-17-oxoestra-1,3,5(10)-triene-3-yl(trifluoromethyl)sulfonate (Scheme 5, Compound 42) (15 g, 34.7 mmol), 1,3-bis(diphenylphosphino)propane (1.54 g, 3.73 mmol), palladium (II) chloride (0.33 g, 1.9 mmol), 1,1,1,3,3,3-hexamethyldisilazane (31 mL, 150 mmol) and anhydrous dimethylformamide (110 mL). Carbon monoxide was bubbled through the yellow solution while stirring for 5 minutes. The reaction was heated to 110° C. under an atmosphere of carbon monoxide (balloon) and allowed to stir for 15 h. During this period the reaction became dark. The reaction was quenched by treating with methanol (25 mL) and stirred for 10 min. The mixture was poured into ethyl acetate (1 L) and washed with 2N sulfuric acid (750 mL). The aqueous layer was extracted with ethyl acetate (2×500 mL) and the combined organic phases were washed with 2N sulfuric acid (250 mL) and saturated aqueous sodium bicarbonate (500 mL) then dried over 500 g of sodium sulfate. This mixture was suction-filtered through a bed of silica gel 60 (67 g) and concentrated to dryness affording crude product (11.2 g, 98% recovery). The crude material was purified by Flash column chromatography (360 g of silica gel 60, eluting with methylene chloride, then 1:5 ethyl acetate: methylene chloride). Concentration of the pure fractions ($R_f$=0.3, 1:5 ethyl acetete:methylene chloride, UV detection) and drying in a vacuum oven at 50° C., and removal of residual solvents afforded pure product (Scheme 5, Compound 54) (4.97 g, 44% yield) as an off-white to pale yellow solid. $^1$H NMR (300 MHz, CDCl$_3$) δ 7.99 (s, 1H), 7.82 (br s, 1H), 7.05 (s, 1H), 5.92 (br s, 1H), 4.02 (s, 3H), 3.05 (dd, 2H, J=5), 2.15 (m 2H,) 2.02-1.65 (m, 6H), 1.55-1.15 (m, 8H), 0.80 (s, 3H). $^{13}$C NMR (125 MHz, CDCl$_3$) δ 220.6, 167.2, 155.9, 145.5, 132.8, 129.4, 118.3, 108.4, 55.9, 50.5, 47.9, 44.9, 37.8, 35.8, 31.6, 28.26, 26.4, 25.8, 21.6, 13.8.

Preparation of (2-methoxyestra-1,3,5(10)-trien-3-yl)-3-carboxamide (57)

A 500 mL, round-bottomed flask fitted with an overhead stirrer, a Claisen adaptor with a thermocouple probe and carbon monoxide inlet, and a vacuum inlet, was charged with 2-methoxyestra-1,3,5(10)-trien-3-yl(trifluoromethyl)sulfonate (Scheme 5, Compound 45) (24 g, 57.35 mmol), anhydrous dimethylformamide (185 mL), palladium (II) chloride (0.500 g, 2.87 mmol), 1,3-bis(diphenylphospino)propane (2.37 g, 5.74 mmol), and 1,1,1,3,3,3-hexamethyldisilazane (48 mL, 229 mmol). The resulting yellow solution was stirred and evacuated, flushed with carbon monoxide (balloon) several times, then heated to 102° C. for 12 h. Additional palladium (II) chloride (0.500 g), 1,3-bis(diphenylphospino)propane (2.40 g), and hexamethyldisilazane (30 mL) were added and the mixture was re-evacuated, charged with carbon monoxide, and heated at 102° C. for an additional 12 h. Methanol (50 mL) was added and, after several minutes, the dark solution was partitioned with ethyl acetate (1000 mL) and 2 N sulfuric acid (1000 mL). The aqueous phase was extracted with ethyl acetate (2×250 mL), the combined organic extracts were washed with additional sulfuric acid (500 mL), and the aqueous phase was back-extracted with ethyl acetate (2×250 mL), and the total combined dark organic layers were washed with saturated aqueous sodium bicarbonate (500 mL) and dried over sodium sulfate (400 g). Suction-filtration through a plug of silica gel 60 (136 g) and concentration afforded 19 g of crude product as a red paste. This was purified by flash chromatography using 430 g of silica gel, and eluting with 10% ethyl acetate-dichloromethane. The product-containing fractions were concentrated, then taken up in acetone and re-concentrated (2×2000 mL). The yellow solid was then slurried in n-heptane (200 mL) overnight and isolated by suction-filtration. Removal of residual solvent, and drying to a constant weight over 3 h in a vacuum oven at 70° C. and 0.5 torr, afforded 5.07 g (28% overall) of (Scheme 5, Compound 57) as an off-white powder. $^1$H NMR (300 MHz, CDCl$_3$) δ 10.82 (br s, 1H), 7.99 (s, 1H), 6.95 (s, 1-1), 4.05 (s, 3H), 2.95 (dd, 2H, J=5), 2.15 (m 2H,) 2.02-1.65 (m, 6H), 1.55-1.15 (m, 8H), 0.80 (s, 3H). C NMR (125 MHz, CDCl$_3$) δ 167.6, 156.1, 147.1, 132.9, 130.0, 116.0, 108.7, 56.2, 54.0, 45.2, 41.2, 40.7, 39.0, 38.6, 28.8, 28.2, 26.7, 25.5, 20.8, 17.8.

Preparation of 2-Methoxy-17-methyleneestra-1,3,5 (10)-triene-3-carboxamide (60)

A 250 mL three-necked flask equipped with an overhead stirrer, thermocouple, and nitrogen inlet, was charged with 2-Methoxy-17-methyleneestra-1,3,5(10)-trien-3-yl(trifluoromethyl)-sulfonate (Scheme 5, Compound 48) (20.0 g, 46.5 mmol), palladium (II) chloride (0.41 g, 2.3 mmol), 1,3-bis (diphenylphosphino) propane (1.9 g, 4.6 mmol), 1,1,1,3,3,3-hexamethyldisilazane (38.8 mL, 186 mmol) and anhydrous dimethylformamide (150 mL). The resulting orange solution was evacuated and back-filled with nitrogen three times, then evacuated and back-filled with carbon monoxide three times. The reaction was warmed to 100° C. and stirred under a carbon monoxide atmosphere (balloon) for 18 hours, during which time the solution became dark red. The heat was removed, methanol (40 mL) was added, and stirred for 10 minutes. The solution was poured into ethyl acetate (1 L) and extracted with 2 N H$_2$SO$_4$ (1 L). The aqueous layer was extracted with ethyl acetate (3×500 mL). Each of the ethyl acetate extracts was washed with 2 N H$_2$SO$_4$ (500 mL). The combined organic phases were washed with saturated aqueous sodium bicarbonate (1 L) and dried over sodium sulfate (500 g). This suspension was suction-filtered through a bed of silica gel 60 (102 g), and the filtrate concentrated to dryness affording 16.02 g (106% recovery) of crude (Scheme 5, Compound 60). The crude product was purified on silica gel 60 (500 g, flash column) eluting with methylene chloride (2 L) then 2% methanol-methylene chloride (4 L) then 4% methanol-methylene chloride (4 L). Chromatography failed to remove all impurities so fractions containing product were combined, concentrated to dryness, and repurified on silica gel 60 (500 g, flash column) eluting with methylene chloride (2 L) then 1:5 ethyl acetate-methylene chloride. Concentration of the pure fractions (TLC, 1:5 ethyl acetate-methylene chloride, R$_f$=0.3, UV detection) and drying in a vacuum oven at 80° C., afforded 12.3 g (81% overall) of (Scheme 5, Compound 60) as a light-yellow solid. Removal of methylene chloride yielded 11.36 g of (Scheme 5, Compound 60) (75% overall yield) as a light-yellow solid. $^1$H NMR (300 MHz, CDCl$_3$) δ 7.94 (s, 1H), 7.63 (br s, 1H), 6.95 (s, 1H), 5.70 (br s, 1H), 4.71 (s, 2H), 3.97 (s, 3H), 2.97-2.82 (m, 2H), 2.65-1.19 (m, 13H), 0.86 (s, 3H). $^{13}$C NMR (CDCl$_3$, 125 MHz) δ 167.2, 161.4, 155.8, 146.3, 132.6, 129.6, 118.0, 108.4, 100.9, 55.9, 53.5, 44.9, 44.2, 38.2, 35.6, 29.4, 28.4, 27.4, 26.4, 23.9, 18.5.

Preparation of 2-methoxy-1,3,5(10)16-estratetraene-3-carboxamide

2-Methoxy-3-triflic-1,3,5(10)16-estratetraene (Scheme 5, Compound 51) (3.195 g, 7.68 mmol) was dissolved in anhydrous N,N-dimethylformamide (25 mL). Palladium (II) chloride (68 mg, 0.384 mmol), 1,3-bis(diphenylphosphino)propane (316 mg, 0.768 mmol) and 1,1,1,3,3,3-hexamethyldisilazane (6.65 mL, 30.72 mmol) were then added and CO gas was bubbled through this solution for 5 min. The reaction flask was fitted with a reflux condenser and a balloon filled with CO was fitted on top. The yellowish mixture was placed in a 100° C. oil bath and stirred for 18 h during which the reaction turned reddish/purple. The reaction flask was cooled to room temperature and methanol (3.5 mL) was added and stirred 10 min. The mixture was poured into ethyl acetate (300 mL) and washed with H$_2$SO$_4$ (2N, 200 mL). The aqueous layer was washed with ethyl acetate (2×150 mL) and the combined organic layers were washed with H$_2$SO$_4$ (2N, 150 mL). The organics were washed with saturated NaHCO$_3$ (2×100 mL), dried with Na$_2$SO$_4$, filtered and solvent was removed under reduced pressure. The crude product was purified using a Biotage FLASH SiO$_2$ column (1:1 hexanes:ethyl acetate). The product obtained from the column was dissolved in acetone and the solvent was removed under reduced pressure to give 1.718 g of 3-carboxamide-2-methoxy-1,3,5(10)16-estratetraene (Scheme 5, Compound 63) (5.52 mmol, 72% yield). $^1$H-NMR (300 MHz, CDCl$_3$) δ 7.94 (s, 1H), 7.76 (br s, 1H), 6.92 (s, 1H), 5.97-5.91 (m, 1H), 5.81-5.75 (m, 1H), 5.68 (br s, 1H), 3.97 (s, 3H), 2.96-2.84 (m, 2H), 2.46-1.20 (m, 11H), 0.83 (s, 3H). $^{13}$C-NMR (75 MHz, CDCl$_3$) δ 172.0, 156.2, 147.1, 144.1, 133.1, 130.1, 129.9, 108.6, 56.3, 55.9, 46.0, 45.9, 37.2, 36.3, 32.2, 28.7, 28.3, 26.8, 17.5. FT-IR (ATR, neat, cm$^{-1}$) 33502, 3378, 2926, 1660, 1609, 1573, 1259, 1184, 1015. Elemental analysis (C$_{20}$H$_{25}$NO$_2$): calculated C, 77.14; H, 8.09; N, 4.50. Found: C, 76.90; H, 8.12; N, 4.64.

Experimental Data

The following Examples refer to compounds of the following general Formulae:

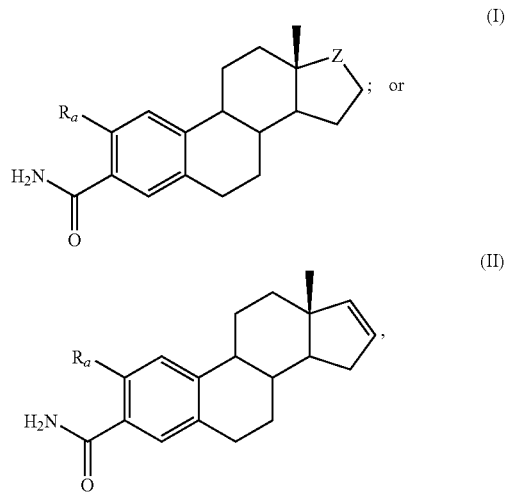

wherein R$_a$ is selected from —OCH$_3$, —OCH$_2$CH$_3$ or —CCCH$_{13}$; and Z is selected from >C(H$_2$), >C(H)—CH$_3$, >C═CH$_2$, >C═CHCH$_3$ (cis or trans), >C═O, >C(H)—OH, >C(H)—O-alkyl, >C(H)—O-sulfamate, wherein alkyl is a linear, branched and/or cyclic hydrocarbon chain comprising 1 to 10 carbons. Preferred species from the foregoing genus that are useful in the present invention include, but are not limited to, the compounds shown in Table I.

TABLE I
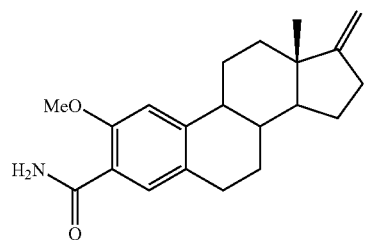
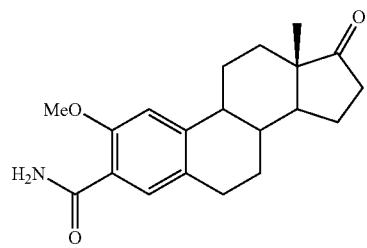
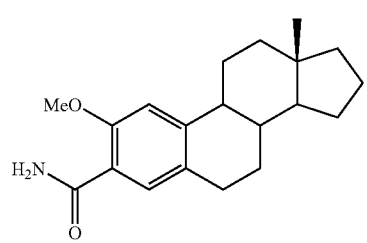
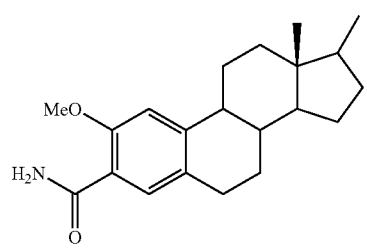
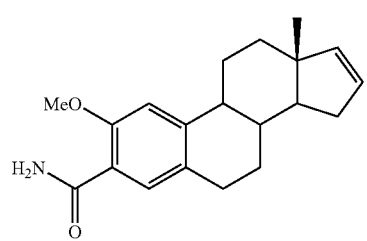
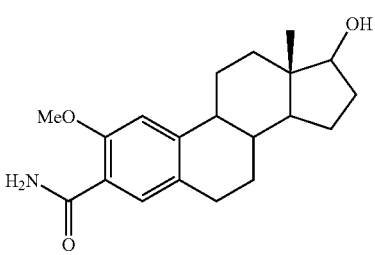
TABLE I-continued
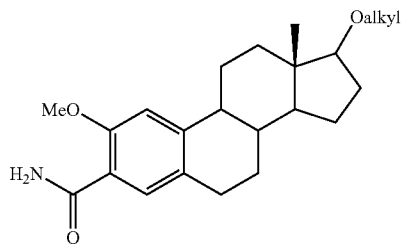
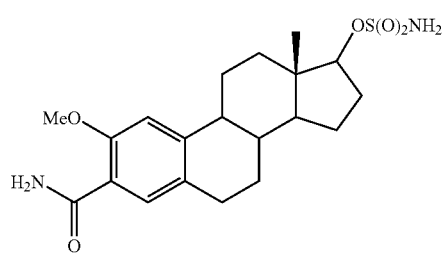
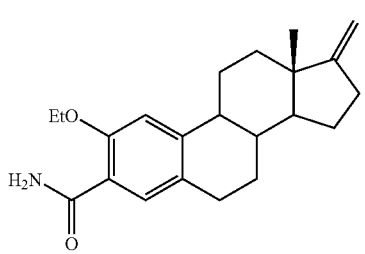
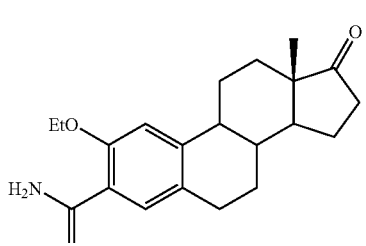
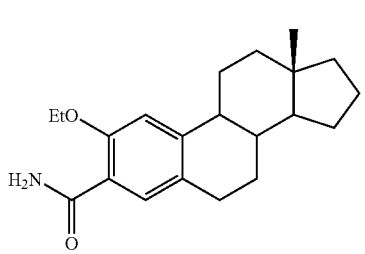
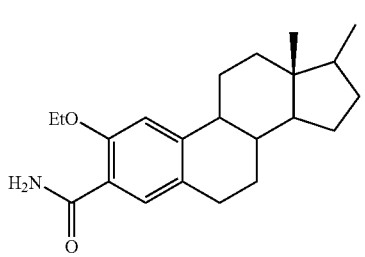

TABLE I-continued
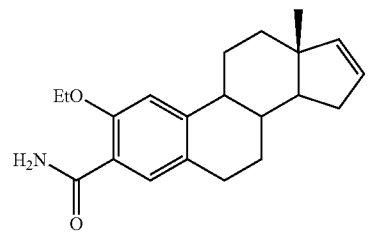
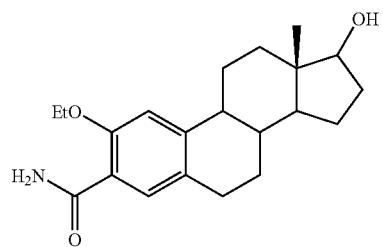
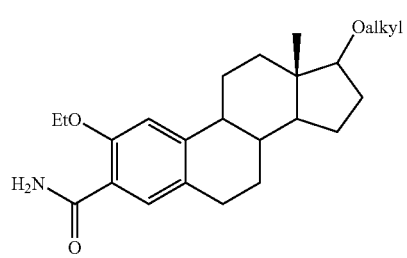
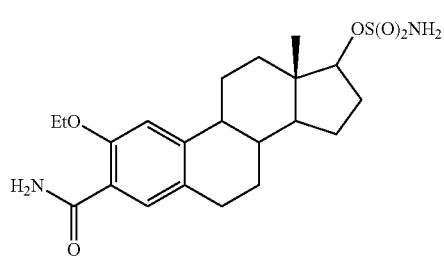
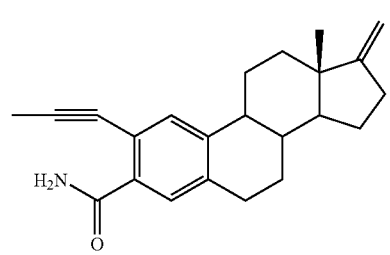
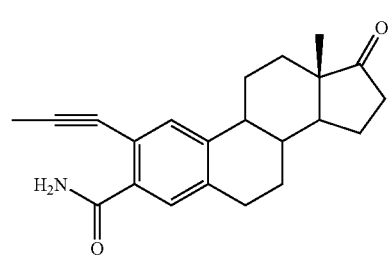
TABLE I-continued
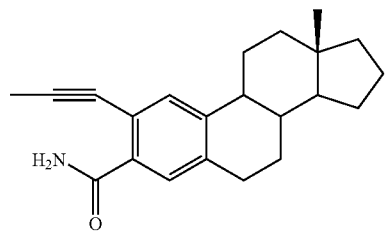
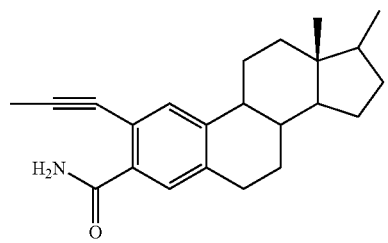
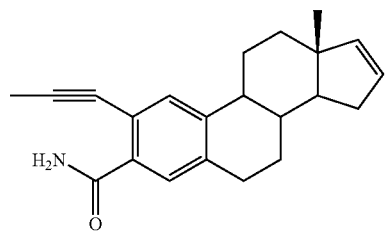
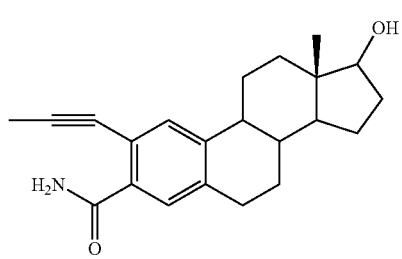
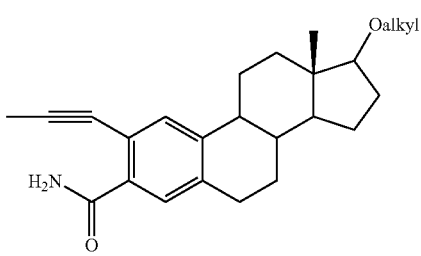
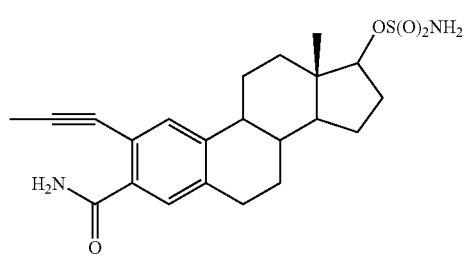

For the compounds shown in Table I above, alkyl is defined as a linear, branched and/or cyclic (or combination thereof) hydrocarbon chain, which can be saturated or unsaturated, comprising 1 to 10 carbons.

Each of the foregoing compounds from Table I is found to have anti-mitotic properties, anti-angiogenic properties, anti-tumor properties or combinations thereof.

Example I

Anti-Tumor and Anti-Angiogenic Activity Measured In Vivo as Inhibition of Proliferation and Measure of Estrogenicity Cell Culture: Human umbilical vein endothelial cells (HUVEC) were obtained from Clonetics (San Diego, Calif.), MCF7 cells were the kind gift of Dr. Dorraya El Ashry (University of Michigan), MDA-MB-231 a human breast carcinoma, PC3 a human prostate carcinoma, and U87-MG a human glioma, cell lines were obtained from ATCC. HUVEC cultures were maintained for up to 5 passages in EGM containing bovine brain extract (Clonetics) and 1× antibiotic-antimycotic (BioWhittaker, Walkersville, Md.). MDA-MB-231, PC3, U87-MG and MCF-7 cells were maintained in DMEM/F12 (1:1) containing 10% (v/v) fetal bovine serum (Hyclone Laboratories, Logan, Utah) and 1× antibiotic-antimycotic. MCF7 cells were used between passage 60 and passage 100.

Proliferation Assays: Proliferation was measured by cell counting using a Coulter Z1 cell counter (Coulter Corporation, Hialeah, Fla.) or by evaluation of DNA synthesis. Each condition was done in triplicate and experiments were repeated at least twice. To determine estrogenicity of the analogs, MCF7 estrogen-dependent proliferation assays were performed. The cells were seeded in complete media at 10,000 cells/well in a 24 well plate after allowing the cells to adhere overnight and the seeding density was determined by cell counts. Cells were washed with PBS (37° C.) and starved by placing them in IMEM-phenol red Free media containing 2% charcoal-dextran fetal bovine-stripped serum (Valley Biomedical, Winchester, Va.) and 1× antibiotic-antimycotic. After 3 days of starvation, cells were treated with or without increasing concentrations of compounds, replacing the media every 2-3 days and counted after 7 days of treatment. In order to ensure that only the added test compounds stimulated growth, experiments were performed only with cell cultures that duplicated less than once during the starvation period. Values are expressed as MCF7 stimulation index (SI) relative to 2ME2 (defined as 1.00). A value less than 1.00 indicates reduced estrogenicity. Estradiol is used as a positive control.

To determine anti-tumor and anti-angiogenic activities of the analogs, proliferation assays were performed by evaluating detection of DNA synthesis by use of the 5-bromo-2'-deoxyuridine (BrdU) cell proliferation calorimetric ELISA kit from Roche (Indianapolis, Ind.) according to the manufacturer's instructions. For BrdU assays, the cells were seeded at 1,000 cells/well (MDA-MB-231, anti-tumor activity) or 3,000 cells/well (HUVEC, anti-angiogenic activity) in a 96 well plate, allowed to attach overnight and then exposed to the compound for 48 h. $IC_{50}$) value is the concentration at which cell proliferation is inhibited by 50%. The results are shown in Table II below.

TABLE II

| Compound number (from schemes 1-6) | MW | MDA-MB-231 (IC50 µM) | U87-MG (IC50 µM) | PC3 (IC50 µM) | HUVEC (IC50 µM) | MCF7 S1 Relative to 2ME$_2$ |
|---|---|---|---|---|---|---|
| 1 | 302.2 | 0.69 ± 0.14 | 1.48 ± 0.62 | 1.08 ± 0.50 | 0.68 ± 0.15 | 1.00 |
| 63 | 311.2 | 0.19 ± 0.04 | 0.23 ± 0.08 | 0.21 ± 0.10 | 0.13 ± 0.05 | 0.28 |
| 60 | 325.2 | 0.19 ± 0.08 | 0.25 ± 0.02 | 0.25 ± 0.01 | 0.12 ± 0.06 | 0.26 |
| 57 | 313.2 | 2.37 ± 0.80 | 10.01 ± 2.49 | 5.70 ± 0.58 | 0.96 ± 0.26 | 0.31 |
| 54 | 327.2 | 2.20 ± 0.43 | 2.23 ± 0.40 | 4.64 ± 0.90 | 5.46 ± 1.57 | 0.26 |

Pharmokinetics (PK): PO Cmax is the maximal concentration of drug achieved after oral administration in rats and AUC is the area under the curve. These parameters are an indication of oral bioavailability. PK parameters were determined using a cassette-dosing approach. A group of new chemical entities (NCEs) (usually 3-6 molecules) was dissolved in DMSO or ethanol and diluted with a solution of a dextrin polymer to the final Working concentration (usually 0.2-2 mg/mL). Groups of three rats with in-dwelling catheters were dosed either orally (5 mg/kg) or i.v. (1 mg/kg) with the cassette of NCEs. Blood was collected at nine time points from 2 minutes to 24 hours. Plasma was separated and aliquots of the replicate samples were pooled for analysis. Plasma proteins were precipitated by addition of organic solvent (most often methanol or acetonitrile). For some analogs, an acid modifier was added to the precipitation mixture to enhance recovery. Precipitated proteins were removed by centrifugation and the supernatant was injected onto a C18 reversed phase column attached to an LC-MS-MS mass spectrometer. Analytes were partly resolved by a rapid (5 minute) gradient of organic modifier. Analytes were measured as either positive or negative ions, depending on ionization characteristics, in the SRM (or MS-MS) mode. Quantification was carried out by correlation of peak heights or areas for each analyte to a set of concentration standards of the same analytes diluted into blank plasma. Concentration vs. time data was analyzed by WinNonLin. The results are shown in liable III below.

TABLE III

| Compound Number (from schemes 1-6) | MW | Rat PO Cmax (nM) | Rat PO AUC (nM) |
|---|---|---|---|
| 63 | 311.2 | 127 | 961 |
| 60 | 325.2 | 185 | 1401 |
| 57 | 313.2 | 130 | 624 |
| 54 | 327.2 | 47 | 185 |

Determination of CYP450 inhibition and $IC_{50}$ value using human microsomes: CYP450 inhibition provides a measure of potential issues with co-medication, since CYP450 enzymes metabolize many drugs. Microsomal incubation mixtures (500 µL) were prepared in HEPES buffer (50 mM HEPES, 15 mM $MgCl_2$, 0.1 mM EDTA, pH 7.6) containing a NADPH regenerating system (1 mM NADPH, 10 mM glucose-6-phosphate 1 IU glucose-6-phosphate dehydrogenase), pooled human liver microsomes (0.5 mg protein), and 5 µL of 7 concentrations of compounds and positive control inhibitors (see Tables IV, V and VI).

TABLE IV

Microsomal incubation conditions

| System | Compounds | Final concentration | Volume added (μL) |
|---|---|---|---|
| HEPES buffer | HEPES | 50 mM | 440 |
| | MgCl₂ | 15 mM | |
| | EDTA | 100 μM | |
| NADPH regenerating system | NADPH | 1 mM | 25 |
| | glucose-6-phosphate | 10 mM | |
| | glucose-6-phosphate dehydrogenase | 1 IU | |
| Microsomes | pooled human liver microsomes | 1 mg/mL | 25 |
| Substrate cocktail* in 50/50 (v/v) acetonitrile/water | Phenacetin | 10 μM | 5 |
| | Tolbutamide | 100 μM | |
| | Omeprazole | 10 μM | |
| | Bufuralol | 10 μM | |
| | Midazolam | 10 μM | |
| Test compound or positive control inhibitor | | | 5 |

*CYP1A2 activity is monitored by phenacetin O-deethylation, CYP2C9 by tolbutamide methyl-hydroxylation, CYP2C19 by omeprazole hydroxylation, CYP2D6 by bufuralol 1'-hydroxylation, and CYP3A by midazolam hydroxylation.

TABLE V

Positive inhibitor controls and test compound concentrations.

| CYP | +/ve control inhibitor | Final concentrations in incubation mixture (μM) |
|---|---|---|
| 1A2 | Furafylline | 0.069-50 |
| 2C9 | Sulfaphenazole | 0.0069-5 |
| 2C19 | Tranylcypromine | 0.069-50 |
| 2D6 | Quinidine | 0.0069-5 |
| 3A4 | Troleandomycin | 0.069-50 |
| | Test compound | 0.034-25 |

After addition of the compounds or positive control inhibitors, the samples were pre-incubated at 37° C. for approximately 5 minutes. Subsequently, the P450 substrate cocktail were added to the reaction mixture and incubated for 20 minutes at 37° C. Reactions were terminated by the addition of 250 μL of methanol containing 5 μM dextrorphan as an internal standard (IS). The samples were vortexed briefly, placed on ice, and then centrifuged at approximately 12000×g for 5 minutes to remove debris. The supernatant from each sample was then transferred to a separate vial for LC-MS/MS analysis. Analysis to determine the amount of substrate specific metabolites (relative to the control samples) was carried out using reverse phase HPLC with tandem mass spectrometric detection (LC-MS/MS). Analysis of the data was carried out using Micromass MetaboLynx and QuanLynx software Versions 3.5 to determine the amount of the specific substrate metabolites produced in each sample (relative to the control samples). The results produced were plotted versus the different concentrations of the test compounds or positive inhibitor control compound, and the IC₅₀ values calculated using Prism non-linear software. The results are shown in Table VI below.

TABLE VI

| Compound Number (from schemes 1-6) | CYP450 inhib. | Hepatocyte Rat 60/120' (1 uM) | Hepatocyte Rat 60/120' (5 uM) | Hepatocyte Human 60/120' (1 uM) | Hepatocyte Human 60/120' (5 uM) |
|---|---|---|---|---|---|
| 1 | CYP1A2 | 0/0 | 39/24 | 0/0 | 20/0 |
| 63 | None | 77/67 | 78/87 | 52/70 | 92/71 |
| 60 | None | 99/87 | 87/NR | NR/91 | 96/93 |
| 57 | None | 91/85 | 95/83 | 111/98 | 117/118 |
| 54 | None | 78/NR | 95/101 | 99/102 | NR/103 |

NR = no reaction

Hepatocyte Incubations: An in vitro measure of metabolism using cells from rat and human liver. Rat and human hepatocyte suspensions (10⁶ cells per mL of serum-free (H)CL15 culture medium) were incubated with 2 concentrations (1 and 5 μM) of each of the compounds. Stock solutions were prepared in DMSO, and were further diluted in culture medium to the final test concentrations. 7-Ethoxycoumarin (7-EC) were included as a positive control substrate for P450. A 0.1 M 7-EC stock solution was prepared in DMSO, and the final assay concentration was 100 μM. The reactions were initiated by the addition of the substrates, incubated at 37° C., and terminated after 0, 60 and 120 minutes by addition of acetonitrile. The positive 7-EC control reactions were stopped with perchloric acid or ZnSO₄ and BaOH after 60-minutes of incubation. The reaction mixture was centrifuged to remove the cell debris, and the supernatant was used for subsequent analysis by HPLC/LC-MS. If necessary, the supernatants were flash frozen in liquid N₂ and stored at −70° C. until further analysis. HPLC was used to analyze product formation from 7-EC. Analyses to determine the concentration of the test compounds were carried Out using reverse phase HPLC with tandem mass spectrometric detection (LC-MS/MS). Samples were analyzed to measure the disappearance of parent compound over time. The rate of metabolism was estimated by fitting a curve to the data for each concentration against time using GraphPad Prism Version 3.02 software. The results are shown in Table VI above.

All of the publications mentioned herein are hereby incorporated by reference in their entireties. The above examples are merely demonstrative of the present invention, and are not intended to limit the scope of the invention or the appended claims.

We claim:

1. A method of treating undesired angiogenesis in a human or animal comprising administering to the human or animal having undesired angiogenesis an effective angiogenesis treating amount of a compound having the formula

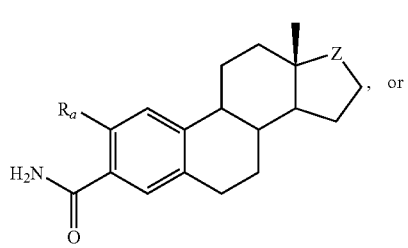

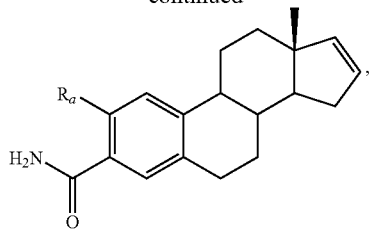

wherein $R_a$ is selected from —OCH$_3$, —OCH$_2$CH$_3$ or —CCCH$_3$; and Z is selected from >C(H)—OH, >C(H)—O-alkyl, >C(H)—O-sulfamate, where alkyl is a linear, branched and/or cyclic hydrocarbon chain comprising 1 to 10 carbons; and
wherein the undesired angiogenesis is associated with atherosclerosis, abnormal would healing, inflammatory disorders, psoriasis, diabetic retinopathy, retinopathy of prematurity (retrolental fibroplastic), macular degeneration, corneal graft rejection, neovascular glaucoma or Osler Weber syndrome (Osler-Weber-Rendu disease).

2. The method of claim 1, wherein the administration of the compound is in a daily dose, a daily sub-dose, or any fraction thereof to the human or animal.

3. The method of claim 1, wherein the amount of the compound administered is approximately 0.1 to approximately 300 mg/kg/day.

4. The method of claim 1, wherein the amount of the compound administered is approximately 0.5 to approximately 50 mg/kg/day.

5. The method of claim 1, wherein the amount of the compound administered is approximately 1 to approximately 10 mg/kg/day.

6. The method of claim 1, wherein the administration of the compound is oral, parenteral, transdermal, topical, intravenous, subcutaneous, intramuscular, intradermal, ophthalmic, epidural, intratracheal, sublingual, buccal, rectal, vaginal, nasal or inhalation.

7. The method of claim 1, wherein the compound is administered in a composition comprising an additive selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

8. The method of claim 1, wherein the compound is administered in the form of a tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, or a transdermal patch.

9. The method of claim 1, wherein the compound is

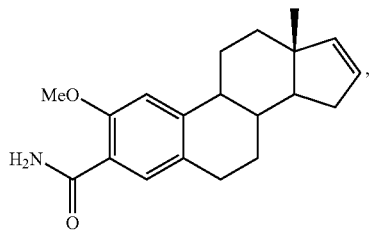

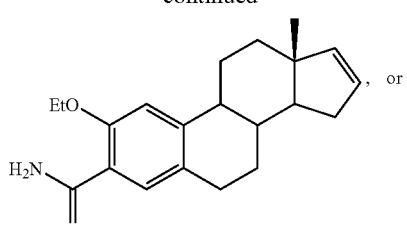

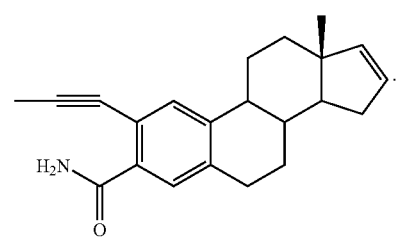

10. A method of treating arthritis in a human or an animal comprising administering to the human or animal having arthritis an effective arthritis treating amount of a compound having the formula

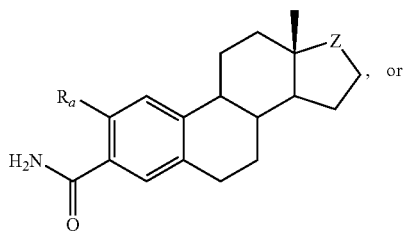

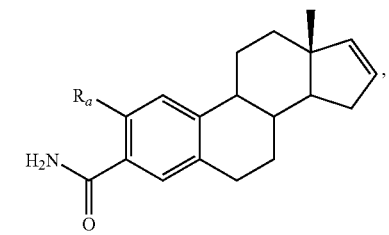

wherein $R_a$ is selected from —OCH$_3$, —OCH$_2$CH$_3$ or —CCCH$_3$; and Z is selected from >C(H)—OH, >C(H)—O-alkyl, >C(H)—O-sulfamate, where alkyl is a linear, branched and/or cyclic hydrocarbon chain comprising 1 to 10 carbons.

11. The method of claim 10, wherein the compound is

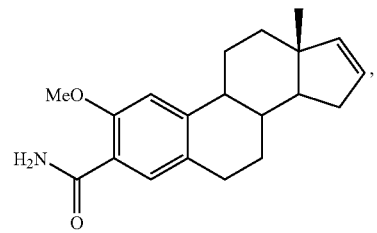

-continued

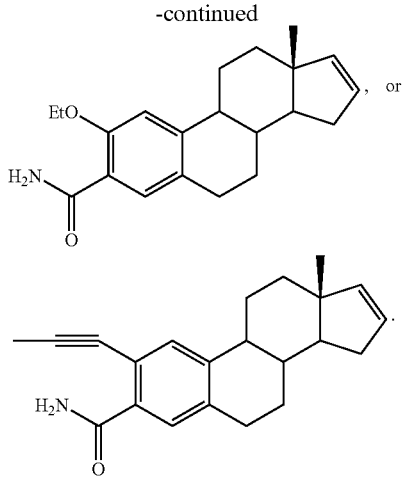

12. The method of claim 10, wherein the arthritis is rheumatoid arthritis.

13. The method of claim 10, wherein the arthritis is osteoarthritis.

14. The method of claim 10, wherein the arthritis is rheumatoid arthritis and the compound is

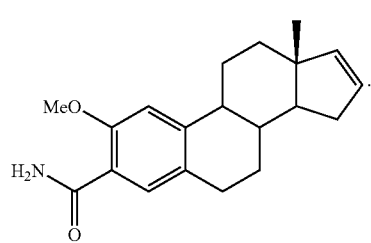

15. A method of treating a tumor in a human or an animal comprising administering to the human or animal an effective tumor treating amount of a compound having the formula

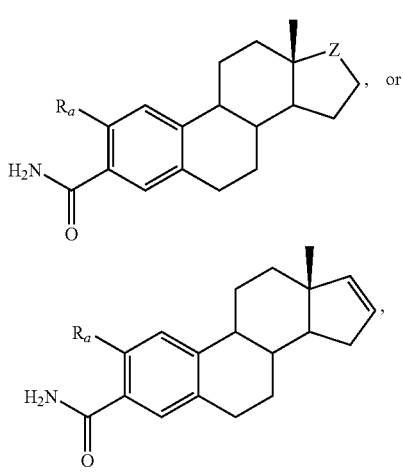

wherein $R_a$ is selected from —OCH$_3$, —OCH$_2$CH$_3$ or —CCCH$_3$; and Z is selected from >C(H)—OH, >C(H)—O-alkyl, >C(H)—O-sulfamate, where alkyl is a linear, branched and/or cyclic hydrocarbon chain comprising 1 to 10 carbons.

16. The method of claim 15, wherein the compound is

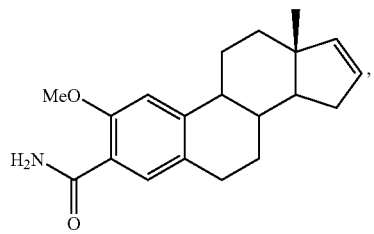

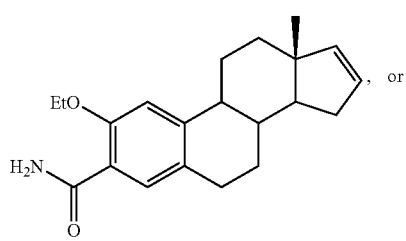

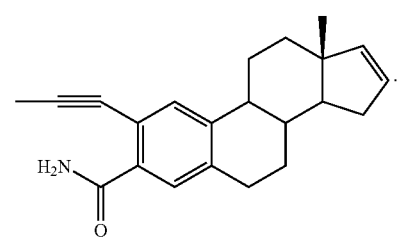

17. The method of claim 15, wherein the tumor is a blood-borne tumor, a solid tumor or a benign tumor.

18. The method of claim 15, wherein the tumor is a solid tumor and the compound is

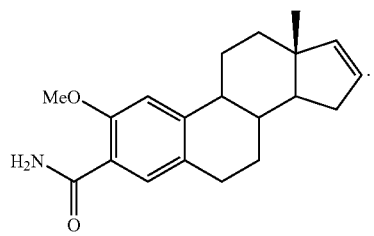

* * * * *